(12) United States Patent
Altal et al.

(10) Patent No.: US 11,487,361 B1
(45) Date of Patent: Nov. 1, 2022

(54) LIGHT FIELD DEVICE AND VISION TESTING SYSTEM USING SAME

(71) Applicant: EVOLUTION OPTIKS LIMITED, Christ Church (BB)

(72) Inventors: Faleh Mohammad Faleh Altal, Montreal (CA); Raul Mihali, Westport, CT (US); Guillaume Lussier, Montreal (CA)

(73) Assignee: EVOLUTION OPTIKS LIMITED, Christ Church (BB)

( * ) Notice: Subject to any disclaimer, the term of this patent is extended or adjusted under 35 U.S.C. 154(b) by 0 days.

(21) Appl. No.: 17/652,368

(22) Filed: Feb. 24, 2022

Related U.S. Application Data

(63) Continuation-in-part of application No. PCT/IB2020/057910, filed on Aug. 24, 2020, which is a continuation of application No. 16/992,583, filed on Aug. 13, 2020, now Pat. No. 11,327,563, which is a continuation-in-part of application No. 16/810,143, filed on Mar. 5, 2020, now Pat. No. 10,761,604, (Continued)

(51) Int. Cl.
| | |
|---|---|
| G06F 3/01 | (2006.01) |
| G06T 3/40 | (2006.01) |
| G02B 27/00 | (2006.01) |
| G06F 3/0484 | (2022.01) |
| G06K 9/00 | (2022.01) |
| G06V 40/19 | (2022.01) |
| G06F 3/04845 | (2022.01) |

(52) U.S. Cl.
CPC ......... *G06F 3/013* (2013.01); *G02B 27/0025* (2013.01); *G06F 3/04845* (2013.01); *G06T 3/40* (2013.01); *G06V 40/19* (2022.01)

(58) Field of Classification Search
CPC . G06F 3/013; G06F 3/04845; G06K 9/00604; G06T 3/40; G02B 27/0025; A61B 3/032
See application file for complete search history.

(56) References Cited

U.S. PATENT DOCUMENTS

| | | |
|---|---|---|
| 5,032,754 A | 7/1991 | Iwao et al. |
| 5,959,664 A | 9/1999 | Woodgate |

(Continued)

FOREIGN PATENT DOCUMENTS

| | | |
|---|---|---|
| AU | 2015100739 | 7/2015 |
| DE | 9410161 U1 | 12/1994 |

(Continued)

OTHER PUBLICATIONS

U.S. Appl. No. 17/302,392, filed Apr. 30, 2021, Guillaume Lussier.

(Continued)

*Primary Examiner* — Jack Dinh

(74) *Attorney, Agent, or Firm* — Knobbe, Martens, Olson & Bear, LLP

(57) ABSTRACT

Described are various embodiments of a light field device and vision-based testing system using same. Different embodiments provide for a vision-based testing device comprising a one or more view zone optimization techniques such as, but not limited to, a predominant view zone isolator, a view zone output realignment solution, and a coarse view zone adjustment transfer solution, as well as other view zone artefact reduction techniques and multi-depth perception adjustment techniques.

26 Claims, 44 Drawing Sheets

Related U.S. Application Data application No. 17/652,368, which is a continuation-in-part of application No. PCT/US2021/070936, filed on Jul. 22, 2021, which is a continuation-in-part of application No. 17/309,133, filed as application No. PCT/IB2020/057887 on Aug. 22, 2020, which is a continuation of application No. 16/810,143, filed on Mar. 5, 2020, now Pat. No. 10,761,604, said application No. PCT/US2021/070936 is a continuation-in-part of application No. 17/302,392, filed on Apr. 30, 2021, now Pat. No. 11,287,883, which is a continuation-in-part of application No. PCT/US2020/058392, filed on Oct. 30, 2020.

(60) Provisional application No. 62/929,639, filed on Nov. 1, 2019, provisional application No. 63/200,433, filed on Mar. 5, 2021, provisional application No. 63/179,057, filed on Apr. 23, 2021, provisional application No. 63/179,021, filed on Apr. 23, 2021.

(56) References Cited

U.S. PATENT DOCUMENTS

| | | |
|---|---|---|
| 6,192,341 B1 | 2/2001 | Becker et al. |
| 6,309,117 B1 | 10/2001 | Bunce et al. |
| 6,386,707 B1 | 5/2002 | Pellicano |
| 6,483,485 B1 | 11/2002 | Huang et al. |
| 6,536,907 B1 | 3/2003 | Towner et al. |
| 6,543,898 B1 | 4/2003 | Griffin et al. |
| 6,784,905 B2 | 8/2004 | Brown et al. |
| 6,809,704 B2 | 10/2004 | Kulas |
| 6,820,979 B1 | 11/2004 | Stark et al. |
| 6,876,758 B1 | 4/2005 | Polat et al. |
| 6,953,249 B1 | 10/2005 | Maguire, Jr. |
| 7,062,547 B2 | 6/2006 | Brown et al. |
| 7,147,605 B2 | 12/2006 | Ragauskas |
| 7,517,086 B1 | 4/2009 | Kürkure |
| 7,819,818 B2 | 10/2010 | Ghajar |
| 7,866,817 B2 | 1/2011 | Polat |
| 7,891,813 B2 | 2/2011 | Ogilvie |
| 7,973,850 B2 | 7/2011 | Ishiga |
| 8,089,512 B2 | 1/2012 | Okabe et al. |
| 8,098,440 B2 | 1/2012 | Jethmalani et al. |
| 8,164,598 B2 | 4/2012 | Kimpe |
| 8,231,220 B2 | 7/2012 | Baranton |
| 8,322,857 B2 | 12/2012 | Barbur et al. |
| 8,540,375 B2 | 9/2013 | Destain |
| 8,717,254 B1 | 5/2014 | Nave et al. |
| 8,783,871 B2 | 7/2014 | Pamplona et al. |
| 8,798,317 B2 | 8/2014 | Wu |
| 8,823,742 B2 | 9/2014 | Kweon |
| 8,857,984 B2 | 10/2014 | Clarke et al. |
| 8,967,809 B2 | 3/2015 | Kirschen et al. |
| 9,010,929 B2 | 4/2015 | Lewis |
| 9,041,833 B2 | 5/2015 | Hatakeyama |
| 9,052,502 B2 | 6/2015 | Caldeira et al. |
| 9,066,683 B2 | 6/2015 | Zhou |
| 9,104,233 B2 | 8/2015 | Alberth |
| 9,159,299 B2 | 10/2015 | Lee |
| 9,177,355 B1 | 11/2015 | Buchheit |
| 9,183,806 B2 | 11/2015 | Felt |
| 9,198,571 B2 | 12/2015 | Kiderman et al. |
| 9,301,680 B2 | 4/2016 | Fassi et al. |
| 9,307,940 B2 | 4/2016 | MacLullich et al. |
| 9,492,074 B1 | 11/2016 | Lee et al. |
| 9,642,522 B2 | 5/2017 | Samadani et al. |
| 9,844,323 B2 | 12/2017 | Pamplona et al. |
| 9,895,057 B2 | 2/2018 | Tumlinson |
| 10,058,241 B2 | 8/2018 | Patella et al. |
| 10,085,631 B2 | 10/2018 | Shimizu et al. |
| 10,182,717 B2 | 1/2019 | Lindig et al. |
| 10,206,566 B2 | 2/2019 | Skolianos et al. |
| 10,247,941 B2 | 4/2019 | Fursich |
| 10,335,027 B2 | 7/2019 | Pamplona et al. |
| 10,345,590 B2 | 7/2019 | Samec et al. |
| 10,394,322 B1 | 8/2019 | Gotsch |
| 10,420,467 B2 | 9/2019 | Krall et al. |
| 10,548,473 B2 | 2/2020 | Escalier et al. |
| 10,761,604 B2 | 9/2020 | Gotsch et al. |
| 2002/0024633 A1 | 2/2002 | Kim et al. |
| 2002/0099305 A1 | 7/2002 | Fukushima et al. |
| 2006/0119705 A1 | 6/2006 | Liao |
| 2007/0247522 A1 | 10/2007 | Holliman |
| 2008/0309764 A1 | 12/2008 | Kubota et al. |
| 2009/0290132 A1 | 11/2009 | Shevlin |
| 2010/0156214 A1 | 6/2010 | Yang |
| 2010/0277693 A1 | 11/2010 | Martinez-Conde et al. |
| 2010/0298735 A1 | 11/2010 | Suffin |
| 2011/0019056 A1 | 1/2011 | Hirsch et al. |
| 2011/0122144 A1 | 5/2011 | Gabay |
| 2011/0157180 A1 | 6/2011 | Burger et al. |
| 2011/0261173 A1 | 10/2011 | Lin et al. |
| 2011/0268868 A1 | 11/2011 | Dowski, Jr. et al. |
| 2012/0010474 A1 | 1/2012 | Olsen et al. |
| 2012/0113389 A1 | 5/2012 | Mukai et al. |
| 2012/0206445 A1 | 8/2012 | Chiba |
| 2012/0249951 A1 | 10/2012 | Hirayama |
| 2012/0254779 A1 | 10/2012 | Ollivierre et al. |
| 2012/0262477 A1 | 10/2012 | Buchheit |
| 2013/0027384 A1 | 1/2013 | Ferris |
| 2013/0096820 A1 | 4/2013 | Agnew |
| 2013/0120390 A1 | 5/2013 | Marchand et al. |
| 2013/0222652 A1 | 8/2013 | Akeley et al. |
| 2014/0028662 A1 | 1/2014 | Liao et al. |
| 2014/0055692 A1 | 2/2014 | Kroll et al. |
| 2014/0063332 A1 | 3/2014 | Miyawaki |
| 2014/0118354 A1 | 5/2014 | Pais et al. |
| 2014/0137054 A1 | 5/2014 | Gandhi et al. |
| 2014/0200079 A1 | 7/2014 | Bathiche et al. |
| 2014/0253876 A1 | 9/2014 | Klin et al. |
| 2014/0267284 A1 | 9/2014 | Blanche et al. |
| 2014/0268060 A1 | 9/2014 | Lee et al. |
| 2014/0282285 A1 | 9/2014 | Sadhvani et al. |
| 2014/0300711 A1 | 10/2014 | Kroon et al. |
| 2014/0327750 A1 | 11/2014 | Malachowsky et al. |
| 2014/0327771 A1 | 11/2014 | Malachowsky et al. |
| 2014/0340390 A1 | 11/2014 | Lanman et al. |
| 2015/0016777 A1 | 1/2015 | Abovitz et al. |
| 2015/0049390 A1 | 2/2015 | Lanman et al. |
| 2015/0177514 A1 | 6/2015 | Maimone et al. |
| 2015/0185501 A1 | 7/2015 | Bakaraju et al. |
| 2015/0234187 A1 | 8/2015 | Lee |
| 2015/0234188 A1 | 8/2015 | Lee |
| 2015/0262424 A1 | 9/2015 | Tabaka et al. |
| 2015/0336511 A1 | 11/2015 | Ukeda |
| 2016/0042501 A1 | 2/2016 | Huang et al. |
| 2016/0103419 A1 | 4/2016 | Callagy et al. |
| 2016/0134815 A1 | 5/2016 | Ishiguro et al. |
| 2016/0260258 A1 | 9/2016 | Lo et al. |
| 2016/0306390 A1 | 10/2016 | Vertegaal et al. |
| 2016/0335749 A1 | 11/2016 | Kano |
| 2017/0027435 A1 | 2/2017 | Boutinon et al. |
| 2017/0060399 A1 | 3/2017 | Hough et al. |
| 2017/0123209 A1 | 5/2017 | Spitzer et al. |
| 2017/0212352 A1 | 7/2017 | Cobb et al. |
| 2017/0227781 A1 | 8/2017 | Banerjee et al. |
| 2017/0302913 A1 | 10/2017 | Fonar et al. |
| 2017/0307898 A1 | 10/2017 | Vdovin et al. |
| 2017/0353717 A1 | 12/2017 | Zhou et al. |
| 2017/0365101 A1 | 12/2017 | Samec et al. |
| 2017/0365189 A1 | 12/2017 | Halpin et al. |
| 2018/0033209 A1 | 2/2018 | Akeley |
| 2018/0070820 A1 | 3/2018 | Fried et al. |
| 2018/0084245 A1 | 3/2018 | Lapstun |
| 2018/0136486 A1 | 5/2018 | Macnamara et al. |
| 2018/0203232 A1 | 7/2018 | Bouchier et al. |
| 2018/0252935 A1 | 9/2018 | Vertegaal et al. |
| 2018/0290593 A1 | 10/2018 | Cho |
| 2018/0329485 A1 | 11/2018 | Carothers et al. |
| 2018/0330652 A1 | 11/2018 | Perreault et al. |
| 2019/0094552 A1 | 3/2019 | Shousha |
| 2019/0125179 A1 | 5/2019 | Xu et al. |
| 2019/0150729 A1 | 5/2019 | Huang et al. |

(56) References Cited

U.S. PATENT DOCUMENTS

| | | | |
|---|---|---|---|
| 2019/0175011 A1 | 6/2019 | Jensen et al. |
| 2019/0228586 A1 | 7/2019 | Bar-Zeev et al. |
| 2019/0246095 A1 | 8/2019 | Kishimoto |
| 2019/0246889 A1 | 8/2019 | Marin et al. |
| 2019/0310478 A1 | 10/2019 | Marin et al. |
| 2020/0012090 A1 | 1/2020 | Lapstun |
| 2020/0272232 A1 | 8/2020 | Lussier et al. |
| 2021/0255701 A1 | 8/2021 | Lussier |
| 2021/0271091 A1 | 9/2021 | Xu et al. |

FOREIGN PATENT DOCUMENTS

| | | |
|---|---|---|
| DE | 102004038822 A1 | 3/2006 |
| DE | 102016212761 | 5/2018 |
| DE | 102018121742 A1 | 3/2020 |
| DE | 102018129600 A1 | 5/2020 |
| DE | 102019102373 A1 | 7/2020 |
| EP | 2127949 A1 | 12/2009 |
| EP | 1509121 B1 | 9/2012 |
| EP | 2589020 A2 | 5/2013 |
| EP | 2678804 A1 | 1/2014 |
| EP | 2760329 A1 | 8/2014 |
| EP | 2999393 A1 | 3/2016 |
| EP | 2547248 B1 | 5/2017 |
| EP | 3262617 A1 | 1/2018 |
| EP | 3339943 A1 | 6/2018 |
| EP | 3367307 A3 | 12/2018 |
| EP | 2828834 B1 | 11/2019 |
| EP | 3620846 A1 | 3/2020 |
| EP | 3631770 A1 | 4/2020 |
| EP | 3657440 A1 | 5/2020 |
| EP | 3659109 A1 | 6/2020 |
| EP | 3689225 A1 | 8/2020 |
| EP | 3479344 B1 | 12/2020 |
| EP | 3313263 A1 | 12/2021 |
| FR | 3059537 B1 | 5/2019 |
| JP | 2003038443 A | 2/2003 |
| WO | 2011156721 A1 | 12/2011 |
| WO | 2013166570 A1 | 11/2013 |
| WO | 2014174168 A1 | 10/2014 |
| WO | 2014197338 A2 | 12/2014 |
| WO | 2015162098 A1 | 10/2015 |
| WO | 2017192887 A2 | 11/2017 |
| WO | 2017218539 A1 | 12/2017 |
| WO | 2018022521 A1 | 2/2018 |
| WO | 2018092989 A1 | 5/2018 |
| WO | 2018129310 A1 | 7/2018 |
| WO | WO2021038421 A1 | 8/2020 |
| WO | WO2021087384 | 10/2020 |
| WO | 2021038430 A1 | 3/2021 |
| WO | 2021122640 A1 | 6/2021 |

OTHER PUBLICATIONS

U.S. Appl. No. 17/309,133, filed Apr. 29, 2021, Daniel Gotsch.
U.S. Appl. No. 62/929,639, filed Nov. 1, 2019, Guillaume Lussier.
"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.
Agus M. et al., "GPU Accelerated Direct Volume Rendering on an Interactive Light Field Display", EUROGRAPHICS 2008, vol. 27, No. 2, 2008.
Burnett T., "FoVI3D Extreme Multi-view Rendering for Light-field Displays", GTC 2018 (GPU Technology Conference), Silicon Valley, 2018.
Ciuffreda, Kenneth J., et al., Understanding the effects of mild traumatic brain injury on the pupillary light reflex, Concussion (2017) 2(3), CNC36.
Fattal, D. et al., A Multi-Directional Backlight for a Wide-Angle, Glasses-Free Three-Dimensional Display, Nature, Mar. 21, 2013, pp. 348-351, vol. 495.
Fielmann Annual Report 2019 (https://www.fielmann.eu/downloads/fielmann_annual_report_2019.pdf).
Gray, Margot, et al., Female adolescents demonstrate greater oculomotor and vestibular dysfunction than male adolescents following concussion, Physical Therapy in Sport 43 (2020) 68-74.
Halle M., "Autostereoscopic displays and computer graphics", Computer Graphics, ACM SIGGRAPH, 31(2), May 1997, pp. 58-62.
Howell, David R., et al., Near Point of Convergence and Gait Deficits in Adolescents After Sport-Related Concussion, Clin J Sport Med, 2017.
Howell, David R., et al., Receded Near Point of Convergence and Gait Are Associated After Concussion, Br J Sports Med, Jun. 2017; 51:e1, p. 9 (Abstract).
Huang, F.C. et al., "Eyeglasses-Free Display: Towards Correcting Visual Aberrations With Computational Light Field Displays,", ACM Transactions on Graphics (TOG)—Proceedings of ACM SIGGRAPH 2014, vol. 33, Issue 4, Article No. 59, Jul. 2014.
Kawata, K., et al., Effect of Repetitive Sub-concussive Head Impacts on Ocular Near Point of Convergence, In t. J Sports Med 2016; 37; 405-410.
Lewin, Sarah "No Need for Reading Glasses With Vision-Correcting Display", published 2014.
Mainone, Andrew, et al. "Focus 3D: Compressive accommodation display." ACM Trans. Graph. 32.5 (2013): 153-1.
Masia B. et al., "A survey on computational displays: Pushing the boundaries of optics, computation, and perception", Computer & Graphics, vol. 37, 2013, pp. 1012-1038.
Murray, Nicholas G., et al., Smooth Pursuit and Saccades after Sport-Related Concussion, Journal of Neurotrauma 36: 1-7 (2019).
Pamplona V. F. et al., "Tailored Displays to Compensate for Visual Aberrations," ACM Transactions on Graphics (TOG), Jul. 2012 Article No. 81, https://doi.org/10.1145/2185520.2185577.
Pamplona V. F., Thesis (Ph.D.)—Universidade Federal do Rio Grande do Sul. Programa de Pós-Graduação em Computação, Porto Alegre, BR-RS, 2012. Advisor: Manuel Menezes de Oliveira Neto.
Ventura, Rachel E., et al., Diagnostic Tests for Concussion: Is Vision Part of the Puzzle?, Journal of Neuro-Ophthalmology 2015; 35; 73-81.
Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.
Zahid, Abdullah Bin, et al., Eye Tracking as a Biomarker for Concussion in Children, Clin J Sport Med 2018.

```
                                    1102
                                    ┌─────────────────────────────────────────┐
                                    │                                         │
                                    │         Eye lens Focal Plane            │
                                    │                                         │
                                    │                    ┌──────────────────┐ │
                                    │                    │ Determine location│ │
                                    │                    │  of eye focal    │ │
                                    │                    │      plane       │ │
                                    │                    └──────────────────┘ │
                                    │                            ▲    1312    │
                                    │         1301               │            │
                                    │        ╱╲                  │            │
                                    │       ╱  ╲                 │            │
                                    │      ╱Ray- ╲                            │
          ──────────────────────────┼────▶ Tracing ╲                          │
                                    │    ╱on Virtual╲                         │
                                    │   ╱Image plane ╲                        │
                                    │   ╲ or on Eye  ╱─────┐                  │
                                    │    ╲Focal Plane╱     │                  │
                                    │     ╲        ╱    ┌──▼───────────────┐  │
                                    │      ╲      ╱     │ Draw vector from │  │
                                    │       ╲    ╱      │ center of display│  │
                                    │        ╲  ╱       │ through pupil    │  │
                                    │  Virtual                Center and find│
                                    │  Image                intersection with│
                                    │  Plane            │   retina plane    │  │
                                    │      │            └──────────────────┘  │
                                    │      │                   │   1308       │
                                    │      ▼                   ▼              │
                                    │  ┌──────────────┐  ┌──────────────────┐ │
                                    │  │Place Virtual │  │  Scale Image on  │ │
                                    │  │Image in plane│  │  Retinal plane   │ │
                                    │  │at Correct    │  └──────────────────┘ │
                                    │  │ Distance     │          │   1310     │
                                    │  └──────────────┘          │            │
                                    │         │   1302           │            │
                                    │         ▼                  │            │
                                    │  ┌──────────────┐          │            │
                                    │  │ Scale Image  │          │            │
                                    │  │on Virtual    │          │            │
                                    │  │   Plane      │          │            │
                                    │  └──────────────┘          │            │
                                    │         │   1304           │            │
                                    │         └─────────┬────────┘            │
                                    │                   │                     │
                                    └───────────────────┼─────────────────────┘
                                                        ▼
```

Figure 13

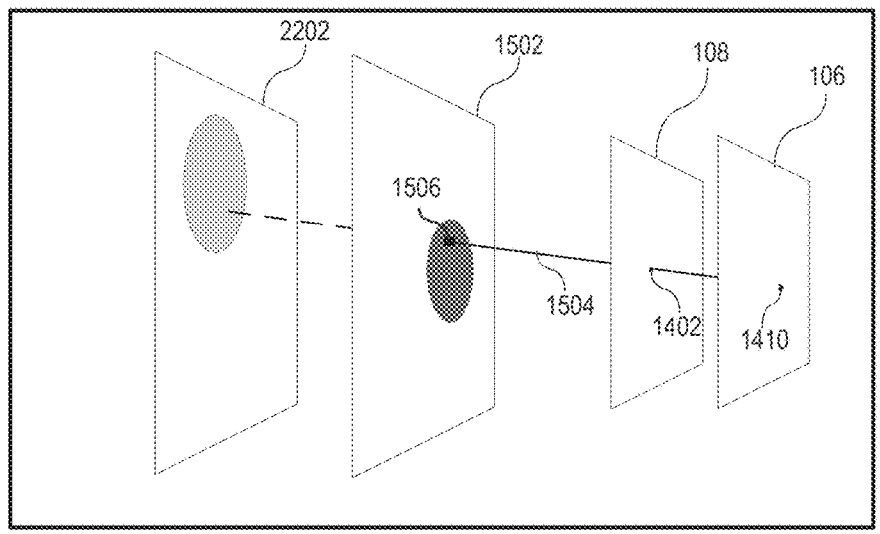
Figure 22A
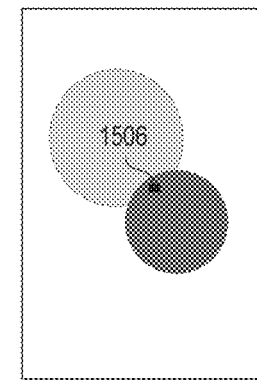
Figure 22B
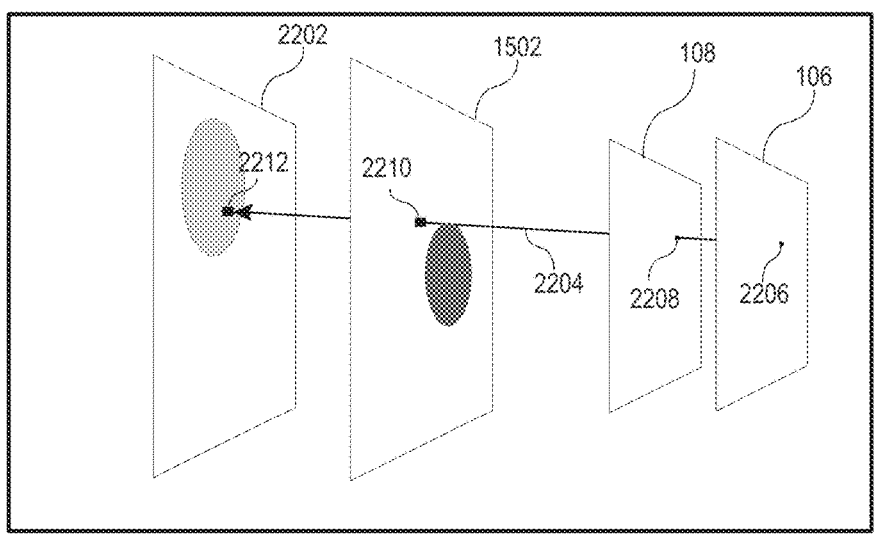
Figure 22C
Figure 22D

US 11,487,361 B1

LIGHT FIELD DEVICE AND VISION TESTING SYSTEM USING SAME

CROSS REFERENCE TO RELATED APPLICATIONS

This application is a continuation-in-part of International Application No. PCT/IB2020/057910 filed Aug. 24, 2020, which is a continuation of U.S. patent application Ser. No. 16/992,583 filed Aug. 13, 2020, which is a continuation-in-part of U.S. patent application Ser. No. 16/810,143 filed Mar. 5, 2020 and issued as U.S. Pat. No. 10,761,604 on Sep. 1, 2020.

This application is also a continuation-in-part of International Application No. PCT/US2021/070936 filed Jul. 22, 2021, which is a continuation-in-part of U.S. patent application Ser. No. 17/309,133 filed Apr. 28, 2021, which is a US national stage of International Application No. PCT/IB2020/057887 filed Aug. 22, 2020, which claims priority to, and is a continuation of, U.S. patent application Ser. No. 16/810,143 filed Mar. 5, 2020 and issued as U.S. Pat. No. 10,761,604 on Sep. 1, 2020. International Application No. PCT/IB2020/057887 also claims priority to U.S. Provisional Application No. 62/929,639 filed Nov. 1, 2019.

International Application No. PCT/US2021/070936 is also a continuation-in-part of U.S. patent application Ser. No. 17/302,392 filed Apr. 30, 2021, which is a continuation-in-part of International Application No. PCT/US2020/058392 filed Oct. 30, 2020.

International Application No. PCT/US2021/070936 also claims priority to U.S. Provisional Application No. 63/200,433 filed Mar. 5, 2021, to U.S. Provisional Application No. 63/179,057 filed Apr. 23, 2021, and to U.S. Provisional Application No. 63/179,021 filed Apr. 23, 2021.

The entire disclosure of each of the above-referenced applications is hereby incorporated herein by reference.

FIELD OF THE DISCLOSURE

The present disclosure relates to digital displays and, in particular, to a light field device and vision-based testing system using same.

BACKGROUND

Refractive errors such as myopia, hyperopia, and astigmatism affect a large segment of the population irrespective of age, sex and ethnic group. If uncorrected, such errors can lead to impaired quality of life. One method to determine the visual acuity of a person is to use a phoropter to do a subjective vision test (e.g. blur test) which relies on feedback from the subject. The phoropter is used to determine the refractive power needed to bring any projected image to focus sharply onto the retina. A traditional phoropter is usually coupled with a screen or a chart where optotypes are presented, for example a Snellen chart. A patient is asked to look through the instrument to a chart placed at optical infinity, typically equivalent to 6 m/20 feet. Then he/she will be asked about the letters/symbols presented on the screen, and whether he/she is able to differentiate/resolve the letters. The patient will keep looking at letters of smaller size or higher resolution power until there is no improvement, at that time the eye-care practitioner is able to determine the visual acuity (VA) of the subject and proceed with the other eye.

There also exists a range of physiological conditions that are indirectly related to the visual system of a patient, and which may be screened for, observed or otherwise detected by testing said visual system. One such physiological condition is cognitive impairment. The Centers for Disease Control estimates that more than 1.6 million people in the United States suffer a concussion—or traumatic brain injury—every year. It was once assumed that the hallmark of a concussion was a loss of consciousness. More recent evidence, however, does not support that. The majority of people diagnosed with a concussion do not experience any loss of consciousness. The most common immediate symptoms are amnesia and confusion. Since the visual system of a person is a relatively easily accessible part of the nervous system, it may be used to evaluate possible brain injury resulting from a concussion or similar. Indeed, the visual system involves half of the brain circuits and many of them are vulnerable to head injury. Traditionally, vision has not been properly used as a diagnostic tool, but a more careful analysis could provide a powerful tool to save precious time in the diagnosis and early treatment. For example, post-concussion syndrome (PCS) involves a constellation of symptoms and/or signs that commonly follow traumatic brain injury (TBI). After a concussion, the oculomotor control, or eye movement, may be disrupted. Examining the oculomotor system may thus provide valuable information in evaluating the presence or degree of cognitive impairment, for example caused by a concussion or similar.

Light field displays are known to adjust a user's perception of an input image by adjusting a light field emanated by the display so to control how a light field image is ultimately projected for viewing. For instance, in some examples, users who would otherwise require corrective eyewear such as glasses or contact lenses, or again bifocals, may consume images produced by such devices in clear or improved focus without the use of such eyewear. Other light field display applications, such as 3D displays, are also known.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for light field device and vision-based testing system using same that overcome some of the drawbacks of known techniques, or at least, provides a useful alternative thereto.

In accordance with one aspect, there is provided a binocular vision-based testing device for digitally implementing a vision-based test for a user using both their left and right eye simultaneously, the device comprising: left and right digital display portions comprising respective pixel arrays; corresponding light field shaping layer (LFSL) portions comprising respective light field shaping element (LFSE) arrays disposed at a distance from said respective pixel arrays to shape a respective left and right light field emanating therefrom; a digital data processor operable on pixel data for vision-based test content to output adjusted pixel data to be simultaneously rendered via said respective pixel arrays and LFSE arrays in accordance with a designated user perception adjustment and projected within respective predominant left and right light field view zones formed thereby along respective optical paths to respective left and right optical outputs while concurrently projecting at least some same vision-based test content within adjacent left and right view zones, respectively; wherein projection of said adjacent left and right view zones toward said right and left optical outputs is optically obstructed from interfering with user viewing of said predominant right and left light field view zones, respectively.

In one embodiment, a distance between a center of said left and right digital display portions is greater than an interpupillary distance resulting in an initial separation between said respective predominant left and right light filed view zones also being greater than said interpupillary distance, wherein said left and right optical outputs are disposed so to substantially correspond with said interpupillary distance, and wherein the device further comprises respective mirror assemblies disposed along said respective left and right optical paths to non-refractively narrow said initial separation substantially in line with said interpupillary distance thereby substantially aligning said left and right light field view zones with said left and right optical outputs.

In one embodiment, the left and right optical outputs and said respective mirror assemblies are adjustable to accommodate different interpupillary distances.

In one embodiment, the mirror assemblies comprise periscope-like assemblies.

In one embodiment, the vision-based test content is to be simultaneously perceived by the left and right eye via said left and right optical outputs to be at a common virtual position relative thereto.

In one embodiment, the common virtual position comprises a virtual depth position relative to said display portions.

In one embodiment, the designated user perception adjustment comprises respective left and right vision correction adjustments.

In one embodiment, the left and right display portions comprise respective displays, and wherein said respective LFSL portions comprise respective microlens arrays.

In one embodiment, the projection of said adjacent left and right view zones is optically obstructed by a physical barrier.

In one embodiment, the digital data processor is operable to adjust rendering of said vision-based test content via said respective LFSL portions so to accommodate for a visual aberration in at least one of a user's left or right eye.

In one embodiment, the visual aberration comprises distinct respective visual aberrations for the left and right eye.

In one embodiment, the vision-based test comprises a visual acuity test to determine an optimal user perception adjustment corresponding with a reduced user visual acuity level in prescribing corrective eyewear or surgery for each of the user's left and right eye.

In one embodiment, the vision-based test is first implemented for each eye separately in identifying a respective optimal user perception adjustment therefor, and wherein both said respective optimal user perception adjustment are then validated concurrently via binocular rendering of said vision-based content according to each said respective optimal user perception adjustment.

In one embodiment, the device is a refractor or a phoropter.

In one embodiment, the vision-based test comprises a cognitive impairment test to determine a physiological user response to a designated set of binocular user perception adjustments.

In one embodiment, the device further comprises respective optical view zone isolators disposed along said respective optical paths between said LFSL portions and said respective left and right optical outputs to at least partially obstruct visual content projected within said adjacent left and right view zones from interfering with visual content projected within said predominant left and right view zones, respectively.

In one embodiment, each of said optical view zone isolators defines a view zone isolating aperture dimensioned and disposed so to at most substantially correspond with a cross section of said predominant view zones.

In one embodiment, the hardware processor is operable to adjust said adjusted pixel data to adjust said designated user perception adjustment within a designated range, wherein the device further comprises an adjustable refractive optical system interposed between said LFSL portions and said respective optical outputs to shift said designated range in extending an overall range of the device, and wherein said respective view zone isolators are disposed between said LFSL portions and said adjustable refractive optical system so to at least partially obstruct projection of said adjacent view zones through said adjustable refractive optical system.

In one embodiment, the adjustable refractive optical system comprises respective tunable lenses or respective lenses selectable from respective arrays of selectable lenses.

In one embodiment, the hardware processor is operable to adjust said adjusted pixel data to adjust said designated user perception adjustment within a designated range, wherein the device further comprises respective tunable lenses interposed between said LFSL portions and said respective optical outputs to shift said designated range in extending an overall range of the device, and wherein said respective view zone isolators are defined by said respective tunable lenses.

In one embodiment, the hardware processor is operable to adjust said adjusted pixel data to adjust said designated user perception adjustment within a designated range, wherein the device further comprises an adjustable refractive optical system interposed between said LFSL portions and said respective optical outputs to shift said designated range in extending an overall range of the device, and wherein the device further comprises an optical assembly to optically transfer respective exit plane light fields of said adjustable refractive optical element to said respective optical outputs.

In one embodiment, the optical assembly comprises respective left and right telescope-like assemblies.

In one embodiment, the telescope-like assemblies optimize at least one of the following light field parameters at the optical outputs: exit aperture, field of view (FoV), and/or angular resolution.

In one embodiment, the telescope-like assemblies define Keplerian-type assemblies each comprising an input lens disposed along said respective optical path at an input lens focal distance downstream from said adjustable refractive optical system to receive said exit plane light field therefrom, and an output lens disposed along said respective optical path at an output lens focal distance upstream of the respective optical output.

In one embodiment, the telescope-like assemblies define Galilean-type telescope assemblies each comprising an input lens disposed along said respective optical path an input lens focal distance upstream of said adjustable refractive optical system, and an output lens disposed along said respective optical path an output lens distance downstream of said adjustable refractive optical system.

In one embodiment, the distance is lower than a focal distance of the LFSE array.

In accordance with another aspect, there is provided a device operable to dynamically adjust user perception of visual content via an optical output thereof, the device comprising: an array of digital display pixels for rendering the visual content to be viewed via the optical output; a light field shaping layer (LFSL) comprising a corresponding array of light field shaping elements (LFSEs) disposed at a distance from said digital display pixels to shape a light field emanated therefrom along an optical path formed with the optical output, wherein said LFSL is positioned so to optically project at least some of the visual content within a predominant view zone along the optical path and aligned with the optical output, while concurrently projecting at least some same visual content within an adjacent view zone; and a hardware processor operable on input pixel data for the visual content to output adjusted pixel data to be rendered via said LFSEs in accordance with a designated user perception within said predominant view zone such that the visual content, when so rendered in accordance with said adjusted pixel data, is projected via said LFSEs to produce said designated user perception of the visual content when viewed via the optical output; an optical view zone isolator disposed along said optical path between said LFSL and the optical output to at least partially obstruct visual content projected within said adjacent view zone from interfering with visual content projected within said predominant view zone at the optical output.

In one embodiment, the optical view zone isolator defines a view zone isolating aperture dimensioned and disposed so to at most substantially correspond with a cross section of said predominant view zone.

In one embodiment, the hardware processor is operable to adjust said adjusted pixel data to adjust said designated user perception within a designated range, wherein the device further comprises an adjustable refractive optical system interposed between said LFSL and the optical output to shift said designated range in extending an overall range of the device, and wherein said view zone isolator is disposed between said LFSL and said adjustable refractive optical system so to at least partially obstruct projection of said adjacent view zone through said adjustable refractive optical system.

In one embodiment, the adjustable refractive optical system comprises at least one of a tunable lens or a lens selectable from an array of selectable lenses.

In accordance with another aspect, there is provided a subjective eye test device comprising: an array of digital display pixels; and a light field shaping layer (LFSL) comprising a corresponding array of light field shaping elements (LFSEs) disposed at a distance from said digital display pixels to shape a light field emanated therefrom along an optical path formed with the optical output, wherein said LFSL is positioned so to optically project rendering of at least one optotype within a predominant view zone along the optical path and aligned with the optical output, while concurrently projecting at least some same said at least one optotype within an adjacent view zone; an optical view zone isolator disposed along said optical path between said LFSL and the optical output to at least partially obstruct said adjacent view zone from interfering with said predominant view zone at the optical output; and a hardware processor operable on input pixel data for the at least one optotype to output adjusted pixel data to be rendered via said LFSEs in accordance with a designated vision correction parameter within said predominant view zone such that said at least one optotype, when so rendered in accordance with said adjusted pixel data, is projected via said LFSEs to at least partially accommodate for a reduced visual acuity condition corresponding to said designated vision correction parameter when viewed via the optical output, wherein said hardware processor is further operable to adjust said designated vision correction parameter to accommodate for a distinct reduced visual acuity condition until an optimal vision correction parameter is identified.

In one embodiment, the hardware processor is operable to adjust said adjusted pixel data to adjust said designated vision correction parameter within a designated range, wherein the device further comprises an adjustable refractive optical system interposed between said LFSL and the optical output to shift said designated range in extending an overall range of the device, and wherein said view zone isolator is disposed between said LFSL and said adjustable refractive optical system so to at least partially obstruct projection of said adjacent view zone through said adjustable refractive optical system.

In accordance with another aspect, there is provided a device operable to dynamically adjust user perception of visual content via an optical output thereof associated with a user eye location, the device comprising: an array of digital display pixels for rendering the visual content to be viewed via the optical output; a light field shaping layer (LFSL) comprising a corresponding array of light field shaping elements (LFSEs) disposed at a distance from said digital display pixels to shape a light field emanated therefrom along an optical path formed with the optical output; a hardware processor operable on input pixel data for the visual content to output adjusted pixel data to be rendered via said LFSEs in accordance with a designated user perception such that the visual content, when so rendered in accordance with said adjusted pixel data, is projected via said LFSEs to produce said designated user perception of the visual content when viewed via the optical output, wherein said hardware processor is operable to adjust said adjusted pixel data to adjust said designated user perception within a designated dioptric range; an adjustable refractive optical element interposed between said LFSL and the optical output to shift said designated dioptric range in extending an overall dioptric range of the device; and an optical assembly disposed along said optical path to optically transfer an exit plane light field of said adjustable refractive optical element to the optical output and user eye location.

In one embodiment, the optical assembly comprises a telescope-like assembly.

In one embodiment, the optical assembly further magnifies or de-magnifies said light field at the optical output.

In one embodiment, the telescope-like assembly optimizes at least one of the following light field parameters at the optical output: exit aperture, field of view (FoV), and/or angular resolution.

In one embodiment, the telescope-like assembly defines a Keplerian-type assembly comprising an input lens disposed along said optical path at an input lens focal distance downstream from said adjustable refractive optical element to receive said exit plane light field therefrom, and an output lens disposed along said optical path at an output lens focal distance upstream of the optical output.

In one embodiment, the telescope-like assembly defines a Galilean-type telescope assembly comprising an input lens disposed along said optical path an input lens focal distance upstream of said adjustable refractive optical element, and an output lens disposed along said optical path an output lens distance downstream of said adjustable refractive optical element.

In accordance with another aspect, there is provided a device operable to render distinct portions of visual content in accordance with respective designated visual perception adjustments, the device comprising: an array of digital display pixels; a corresponding array of light field shaping elements (LFSEs) disposed at a distance from said digital display pixels to shape a light field emanated therefrom; and a hardware processor operable to associate a respective subset of the display pixels with each of the distinct portions, and further operable on input pixel data for each of the distinct portions to output respectively adjusted pixel data therefor in accordance with a respective designated visual perception adjustment associated therewith, such that each of the distinct portions, when rendered according to said respectively adjusted pixel data via said respective subset of the display pixels, is projected via said LFSEs such that each of the portions are effectively viewed concurrently in accordance with their respective designated visual perception adjustment.

In one embodiment, the hardware processor is operable to simultaneously render said respectively adjusted pixel data for each of the distinct portions via each said respective distinct subset of the display pixels.

In one embodiment, the hardware processor is operable to alternatingly render said respectively adjusted pixel data for each of the distinct portions via each said respective distinct subset of the display pixels.

In one embodiment, the hardware processor is operable to alternatingly render said respectively adjusted pixel data at a frequency beyond a visible flicker frequency.

In one embodiment, the respective designated visual perception adjustments comprise respective perceived image portion depths.

In one embodiment, the respective designated visual perception adjustments correspond with respective visual aberration correction parameters, and wherein said hardware processor is further operable to dynamically adjust said respective visual aberration correction parameters for comparative purposes until an optimal visual aberration corrective parameter is identified in prescribing corrective eyewear or surgery.

In one embodiment, the distinct portions are rendered in accordance with said respective visual aberration correction parameters in respective quadrants of said digital display.

In accordance with another aspect, there is provided a device operable to render distinct portions of visual content in accordance with respective designated visual perception adjustments, the device comprising: an array of digital display pixels; a corresponding array of light field shaping elements (LFSEs) disposed at a distance from said digital display pixels to shape a light field emanated therefrom; a hardware processor operable on input pixel data for each of the distinct portions to output respectively adjusted pixel data therefor in accordance with a respective designated visual perception adjustment associated therewith, such that each of the distinct portions, when rendered according to said respectively adjusted pixel data, is projected via said LFSEs to produce said respective designated visual perception adjustment accordingly, wherein said hardware processor is operable to alternatingly render said respectively adjusted pixel data for each of the distinct portions beyond a visible flicker frequency such that each of the portions are effectively viewed concurrently in accordance with their respective designated visual perception adjustment.

In one embodiment, the respective designated visual perception adjustments comprise respective perceived image portion depths.

In one embodiment, the respective designated visual perception adjustments correspond with respective visual aberration correction parameters, and wherein said hardware processor is further operable to dynamically adjust said respective visual aberration correction parameters for comparative purposes until an optimal visual aberration corrective parameter is identified in prescribing corrective eyewear or surgery.

In one embodiment, the distinct portions are rendered in accordance with said respective visual aberration correction parameters in respective quadrants of said digital display.

In accordance with another aspect, there is provided a computer-implemented method, automatically implemented by one or more digital processors, to adjust perception of distinct portions of visual content to be rendered via a set of pixels and a corresponding array of light field shaping elements (LFSE), in accordance with respective designated visual perception adjustments, the method comprising: associating a respective subset of the display pixels with each of the distinct portions; adjusting pixel data associated with each of the distinct portions to output respectively adjusted pixel data therefor in accordance with a respective designated visual perception adjustment associated therewith; rendering each of the distinct portions according to said respectively adjusted pixel data via said respective subset of the display pixels to be projected via said LFSEs such that each of the portions are effectively viewed concurrently in accordance with their respective designated visual perception adjustment.

In one embodiment, the rendering comprises simultaneously rendering said respectively adjusted pixel data for each of the distinct portions via each said respective distinct subset of the display pixels.

In one embodiment, the rendering comprises alternatingly rendering said respectively adjusted pixel data for each of the distinct portions via each said respective distinct subset of the display pixels at a frequency beyond a visible flicker frequency.

In one embodiment, the respective designated visual perception adjustments comprise respective perceived image portion depths.

In one embodiment, the respective designated visual perception adjustments correspond with respective visual aberration correction parameters, and wherein the method further comprises dynamically adjusting said respective visual aberration correction parameters for comparative purposes until an optimal visual aberration corrective parameter is identified in prescribing corrective eyewear or surgery.

In accordance with another aspect, there is provided a computer-implemented method, automatically implemented by one or more digital processors, to adjust perception of distinct portions of visual content to be rendered via a set of pixels and a corresponding array of light field shaping elements (LFSE), in accordance with respective designated visual perception adjustments, the method comprising: adjusting pixel data associated with each of the distinct portions to output respectively adjusted pixel data therefor in accordance with a respective designated visual perception adjustment associated therewith; alternatingly rendering said respectively adjusted pixel data for each of the distinct portions beyond a visible flicker frequency such that each of the portions are effectively viewed concurrently in accordance with their respective designated visual perception adjustment.

In accordance with another aspect, there is provided a subjective vision-based testing device comprising: an array of digital display pixels; a corresponding array of light field shaping elements (LFSEs) disposed at a distance from said digital display pixels to shape a light field emanated therefrom; a hardware processor operable on input pixel data for each of distinct image portions set to correspond with respective designated visual aberration correction parameters, to output respectively adjusted pixel data therefor in accordance with said respective designated visual aberration correction parameters such that each of the distinct image portions, when rendered according to said respectively adjusted pixel data, is projected via said LFSEs such that each of the portions are effectively viewed concurrently in accordance with their respective designated visual aberration correction parameter; wherein said hardware processor is further operable to dynamically adjust said respective visual aberration correction parameters for comparative purposes until an optimal visual aberration corrective parameter is identified in prescribing corrective eyewear or surgery.

In one embodiment, the hardware processor is operable to alternatingly render said respectively adjusted pixel data for each of the distinct portions beyond a visible flicker frequency such that each of the portions are effectively viewed concurrently in accordance with their respective designated visual aberration correction parameter.

In one embodiment, the hardware processor is operable to simultaneously render said respectively adjusted pixel data for each of the distinct portions via respective subjects of the display pixels such that each of the portions are effectively viewed concurrently in accordance with their respective designated visual aberration correction parameter.

In one embodiment, the distinct portions are rendered to be perceived within respective quadrants.

In accordance with another aspect, there is provided a computer-implemented method, automatically implemented by one or more digital processors, given a user pupil location, to adjust perception of an input to be rendered via a set of pixels and a corresponding array of light field shaping elements (LFSE), wherein the array of LFSE is defined by a LFSE array geometry, the method comprising: virtually defining, at the user pupil location, a non-circular digital pupil shape defined as a function of said LFSE array geometry and dimensioned as a function of a user pupil dimension; for at least some of said pixels, digitally: projecting an adjusted ray trace linking a given pixel and the user pupil location given a corresponding LFSE intersected thereby, to intersect an adjusted image surface at a given adjusted image surface location, wherein said adjusted image surface corresponds to a designated perception adjustment; and only upon said adjusted ray trace intersecting said non-circular digital pupil shape at the user pupil location, associating an adjusted pixel value designated for said given adjusted plane location with said given pixel for rendering a perceptively adjusted version of the input.

In one embodiment, the non-circular shape is defined as a function of a symmetry of said LFSE array geometry.

In one embodiment, the non-circular shape is defined as a function of a reciprocal lattice unit cell of said LFSE array.

In one embodiment, an orientation of said non-circular shape is further defined as a function of a rotation of said LFSE array relative to said pixel array.

In one embodiment, the non-circular digital pupil shape is dimensioned to substantially correspond with a given or average user pupil dimension.

In one embodiment, a central portion of said non-circular digital pupil shape is dimensioned to correspond with a given or average user pupil dimension, whereas said non-circular digital pupil shape further comprises a dead-zone extent extending beyond said central portion such that adjusted pixel data associated with any said adjusted ray trace intersecting said dead-zone extend is adjusted accordingly and distinctly from any said adjusted ray trace intersecting said central region of said non-circular digital pupil shape.

In one embodiment, the adjusted pixel data associated with said dead-zone extent is distinctly adjusted in accordance with at least one of a designated brightness uniformity, contrast, view zone transition intensity level, view zone transition intensity transition fade rate, or view zone transition blurring.

In one embodiment, the non-circular digital pupil shape is defined by a circumscribed polygon having a number of sides equal to a number of sides of a unit cell of a reciprocal lattice of said LFSE array, and wherein each of said sides of said circumscribed polygon is tangent to a circle centered on a user pupil center location and having a radius defined as a function of a given or average user pupil radius.

In one embodiment, the radius is substantially equal to said given or average pupil radius.

In one embodiment, the computer-implemented method further comprises tracking the given user pupil location via a pupil or eye tracker.

In one embodiment, the computer-implemented method further comprises receiving as input said user pupil dimension via said pupil or eye tracker.

In accordance with another aspect, there is provided a device for adjusting perception of an input, the device comprising: a set of pixels; a corresponding array of light field shaping elements (LFSE), wherein the array of LFSE is defined by a LFSE array geometry; a digital data processor operable to: virtually define, at a user pupil location, a non-circular digital pupil shape defined as a function of said LFSE array geometry and dimensioned as a function of a user pupil dimension; for at least some of said pixels, digitally: projecting an adjusted ray trace linking a given pixel and the user pupil location given a corresponding LFSE intersected thereby, to intersect an adjusted image surface at a given adjusted image surface location, wherein said adjusted image surface corresponds to a designated perception adjustment; and only upon said adjusted ray trace intersecting said non-circular digital pupil shape at the user pupil location, associating an adjusted pixel value designated for said given adjusted plane location with said given pixel for rendering a perceptively adjusted version of the input.

In one embodiment, an orientation of said non-circular shape is further defined as a function of a rotation of said LFSE array relative to said pixel array.

In one embodiment, the device further comprises a pupil or eye tracker for tracking the given user pupil location.

In one embodiment, the digital data processor is further operable to access said user pupil dimension via said pupil or eye tracker.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 13 is a process flow diagram illustrating certain process steps of FIG. 11, in accordance with one embodiment;

FIGS. 22A to 22D are schematic diagrams illustrating certain process steps of FIGS. 21A and 21B, in accordance with one embodiment;

Figure 1A:
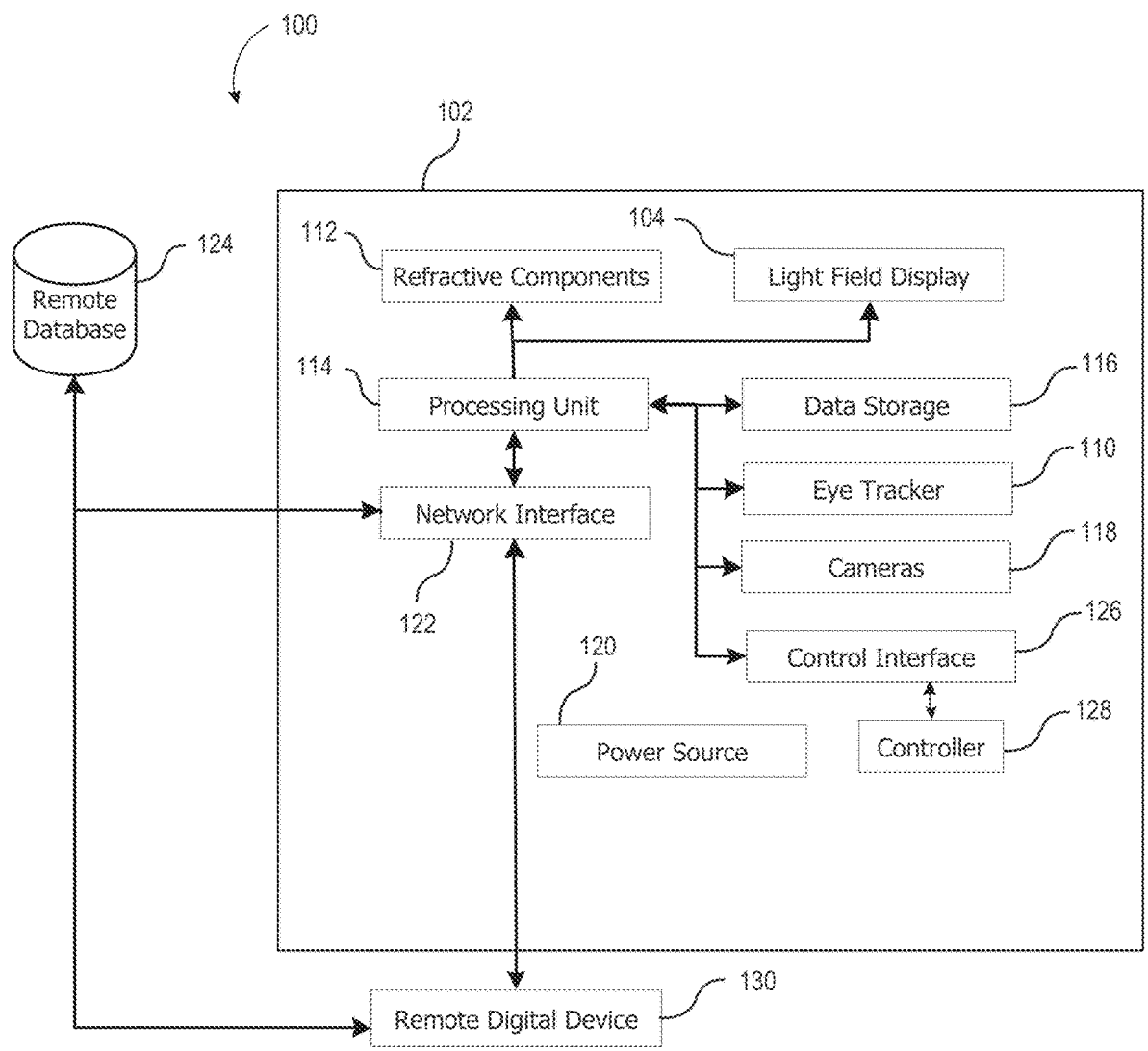
FIGS. 1A and 1B are schematic diagrams of an exemplary light field vision testing or previewing system, in accordance with one embodiment.

Elements in the several figures are illustrated for simplicity and clarity and have not necessarily been drawn to scale.

For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The systems and methods described herein provide, in accordance with different embodiments, different examples of light field vision-based testing systems and methods for assessing the presence of one or more vision-related physiological conditions, such as a light field refractor and/or refractor, or vision-based cognitive impairment detection device or system, adjusted pixel rendering methods therefor, and online or telepresence vision-based testing systems and methods using same.

These vision-related physiological conditions, as the name implies, may include any physiological condition which affects, directly or indirectly, a patient's visual system. For example, this may include reduced or impacted visual acuity itself, but also other conditions such as cognitive impairment as a result of a concussion or similar neurological trauma that may impact a user's vision, visual acuity, responsivity, etc.

In addition, the systems and methods described herein also provide, in some embodiments, for remotely administering via a network connection, at least in part, a vision-based examination by a remotely located specialist, for example an ophthalmologist or eye doctor in the case of a vision examination or a physician or brain specialist in the case of a cognitive impairment examination. Such telepresence may allow for enhanced accuracy in the implementation of a particular test, greater patient comfort during and trust in results achieved from such tests, greater geographical reach of such tests for implementation in the field (e.g. within a competitive sport context, dangerous work sites, etc.) or in remote locations where expertise on the ground may be limited or inaccessible, or other such advantages.

For example, a subjective vision (e.g. blur) testing tool can rely on the herein-described solutions to simultaneously depict distinct optotypes corresponding to respective optical resolving or corrective powers in providing a subjective basis for optical testing comparisons, while concurrently or intermittently rendering testing guidance or support from within a same device, such as by means of an integrated livestream or pre-recorded guidance video, instructions or the like. For example, the devices, displays and methods described herein may allow a user's perception of one or more input images (or input image portions), where each image or image portion is virtually located at a distinct image plane/depth location, to be adjusted or altered using the light field display. These may be used, as described below, to provide vision correction for a user viewing such digital displays, but the same light field displays and rendering technology, as detailed below and according to different embodiments, may also be used or be implemented in a refractor or phoropter-like device to test, screen, diagnose and/or deduce a patient's reduced visual acuity.

In accordance with some embodiments, different vision testing devices and systems as described herein may be contemplated so to replace or complement traditional vision testing devices such as refractors and/or phoropters, in which traditional devices different optotypes are shown to a user in sequence via changing and/or compounding optical elements (lenses, prisms, etc.) so to identify an optical combination that best improves the user's perception of these displayed optotypes. As will be described in greater detail below, embodiments as described herein introduce light field display technologies and image rendering techniques, alone or in combination with complementary optical elements such as refractive lens, prisms, etc., to provide, amongst other benefits, for greater vision testing versatility, compactness, portability, range, precision, and/or other benefits as will be readily appreciated by the skilled artisan. Accordingly, while the terms light field refractor or phoropter will be used interchangeably herein to reference the implementation of different embodiments of a more generally defined light field vision testing device and system, the person of ordinary skill in the art will appreciate the versatility of the herein described implementation of light field rendering techniques, and ray tracing approaches detailed herein with respect to some embodiments, in the provision of effective light field vision testing devices and systems in general.

As noted above, some of the herein described embodiments provide for digital display devices, or devices encompassing such displays, for use by users having reduced visual acuity, whereby images ultimately rendered by such devices can be dynamically processed to accommodate the user's reduced visual acuity so that they may consume rendered images without the use of corrective eyewear, as would otherwise be required. Accordingly, such embodiments can be dynamically controlled to progressively adjust a user's perception of rendered images or image portions (e.g. optotype within the context of a blur test for example) until an optimized correction is applied that optimizes the user's perception. Perception adjustment parameters used to achieve this optimized perception can then be translated into a proposed vision correction prescription to be applied to corrective eyewear. Conversely, a user's vision correction eyewear prescription can be used as input to dictate selection of applied vision correction parameters and related image perception adjustment, to validate or possibly further fine tune the user's prescription, for example, and progressively adjusting such correction parameters to test for the possibility of a further improvement. As noted above, embodiments are not to be limited as such as the notions and solutions described herein may also be applied to other technologies in which a user's perception of an input image to be displayed can be altered or adjusted via the light field display. However, for the sake of illustration, a number of the herein described embodiments will be described as allowing for implementation of digitally adaptive vision tests such that individuals with such reduced visual acuity can be exposed to distinct perceptively adjusted versions of an input image(s) (e.g. optotypes) to subjectively ascertain a potentially required or preferred vision correction.

Moreover, different vision or visual system testing tools may also rely on the herein described solutions to provide a fast and reliable response when a head injury happens. For example, after mild traumatic head injury (TBI) or concussion, common visual disorders that may ensue include convergence insufficiency (CI), accommodative insufficiency (AI), and mild saccadic dysfunction (SD). Since a mild concussion is frequently associated with abnormalities of saccades, pursuit eye movements, convergence, accommodation, and the vestibular-ocular reflex, testing or evaluating the vision system or eyes of an individual suspected of being cognitively impaired may be used to detect abnormalities in some of these aspects. For example, such tools may be highly beneficial, in some embodiments or applications, for a quick evaluation, assessment or screening (e.g. in a clinical environment, in the field and/or through other direct/remote configurations), especially when it may differentiate between mild and no concussion. Most people with visual complaints after a concussion have 20/20 distance visual acuity so more specific testing of near acuity, convergence amplitudes, ocular motility, and peripheral vision can be done. The light field rendering and vision testing tools described below may be used to implement the required tests to evaluate some of the signs and symptoms of TBI. Furthermore, the telepresence features described herein in accordance with some embodiments may again enhance or promote greater adherence to testing protocols, and/or provide more reliable results and conclusions.

Generally, digital displays as considered herein will comprise a set of image rendering pixels and a corresponding set of light field shaping elements that at least partially govern a light field emanated thereby to produce a perceptively adjusted version of the input image, notably distinct perceptively adjusted portions of an input image or input scene, which may include distinct portions of a same image, a same 2.5D/3D scene, or distinct images (portions) associated with different image depths, effects and/or locations and assembled into a combined visual input. For simplicity, the following will generally consider distinctly addressed portions or segments as distinct portions of an input image, whether that input image comprises a singular image having distinctly characterized portions, a digital assembly of distinctly characterized images, overlays, backgrounds, foregrounds or the like, or any other such digital image combinations.

In some examples, light field shaping elements may take the form of a light field shaping layer or like array of optical elements to be disposed relative to the display pixels in at least partially governing the emanated light field. As described in further detail below, such light field shaping layer elements may take the form of a microlens and/or pinhole array, or other like arrays of optical elements, or again take the form of an underlying light shaping layer, such as an underlying array of optical gratings or like optical elements operable to produce a directional pixelated output.

Within the context of a light field shaping layer, as described in further detail below in accordance with some embodiments, the light field shaping layer can be disposed at a pre-set distance from the pixelated display so to controllably shape or influence a light field emanating therefrom. For instance, each light field shaping layer can be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping elements and/or layer, e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping element and/or layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer and/or elements, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Figure 1B:
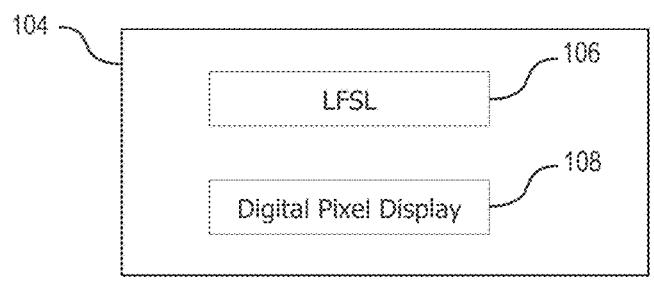

With reference to FIGS. 1A and 1B, and in accordance with different embodiments, an exemplary subjective vision testing device/system (interchangeably referred to as a corrective vision previewing device/system), generally referred to using the numeral 100, will now be described. At the heart of this system is a light field vision testing device such as a light field refractor or phoropter device 102. Generally, light field refractor 102 is a device comprising, as mentioned above, a light field display 104 and which is operable to display or generate one or more images, including optotypes, to a user or patient having his/her vision acuity (e.g. refractive error) tested.

In some embodiments, as illustrated in FIG. 1B, light field display 104 comprises a light field shaping layer (LFSL) 108 overlaid or placed in front of a digital pixel display 110 (i.e. LCD, LED, OLED, etc.). For the sake of illustration, the following embodiments will be described within the context of a LFSL 108 defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources (e.g. directional light sources and/or backlit integrated optical grating array) or like component.

Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display.

Figure 2A:
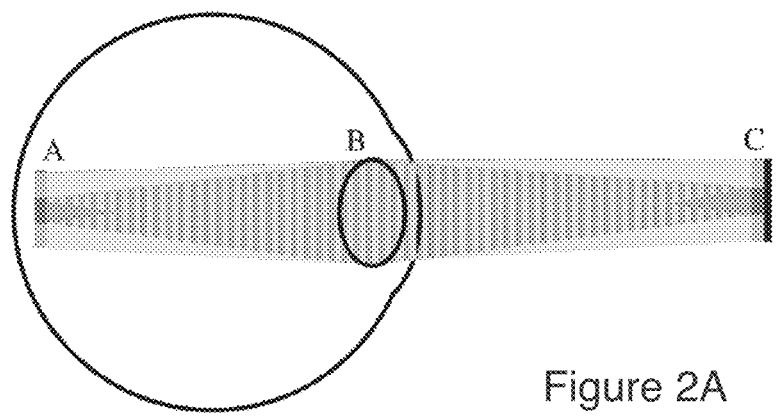
FIGS. 2A to 2C schematically illustrate normal vision, blurred vision, and corrected vision in accordance with one embodiment, respectively.
Figure 2B:
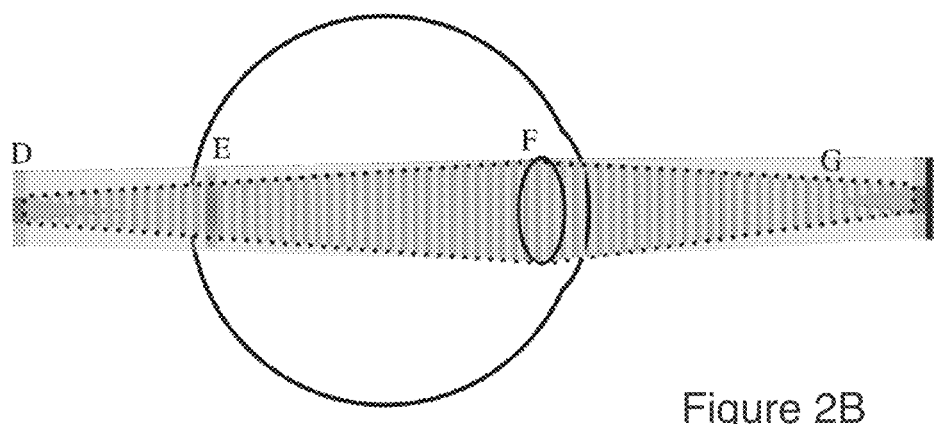

In one example, to apply this technology to vision correction, consider first the normal ability of the lens in an eye, as schematically illustrated in FIG. 2A, where, for normal vision, the image is to the right of the eye (C) and is projected through the lens (B) to the retina at the back of the eye (A). As comparatively shown in FIG. 2B, the poor lens shape and inability to accommodate (F) in presbyopia causes the image to be focused past the retina (D) forming a blurry image on the retina (E). The dotted lines outline the path of a beam of light (G). Naturally, other optical aberrations present in the eye will have different impacts on image formation on the retina. To address these aberrations, a light field display 104, in accordance with some embodiments, projects the correct sharp image (H) on the retina for an eye with a crystalline lens which otherwise could not accommodate sufficiently to produce a sharp image. The other two light field pixels (I) and (J) are drawn lightly, but would otherwise fill out the rest of the image.

Figure 2C:
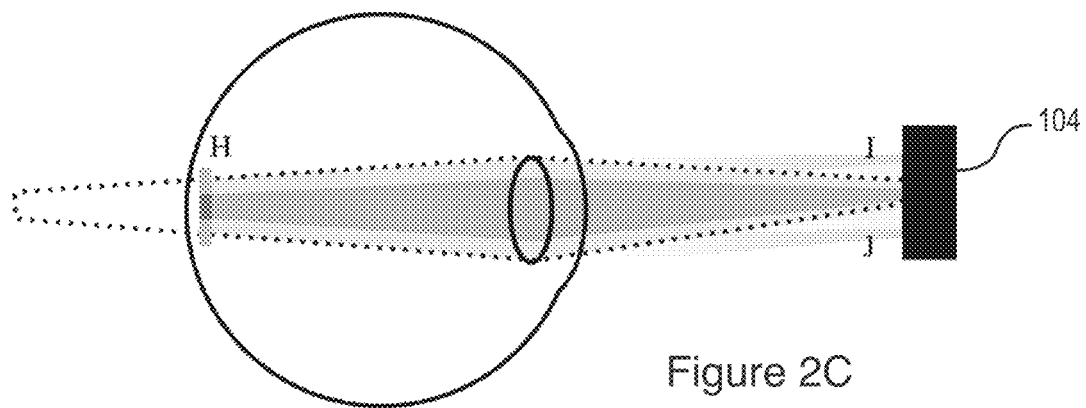
Figure 3A:
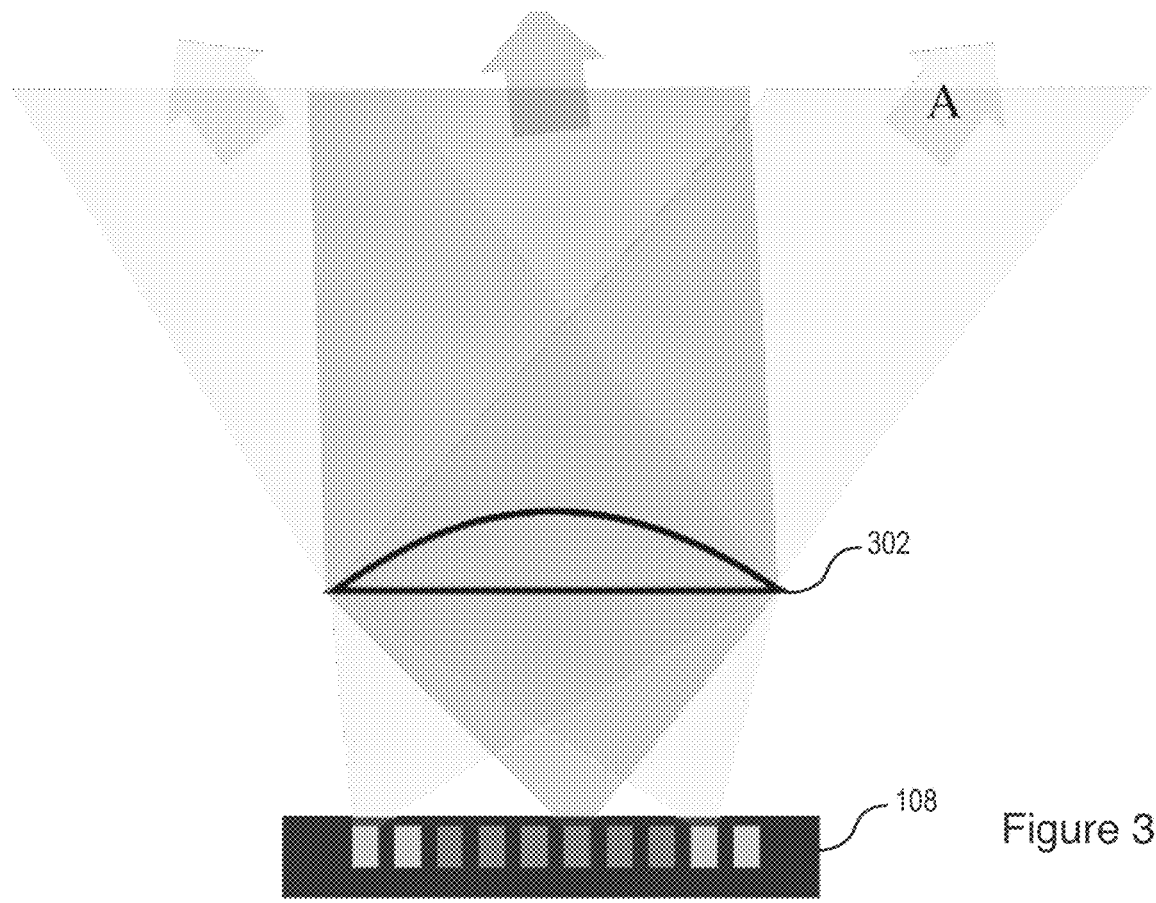
FIGS. 3A and 3B are schematic diagrams of a light field display in which respective pixel subsets are aligned to emit light through a corresponding microlens or lenslet, in accordance with one embodiment.

As will be appreciated by the skilled artisan, a light field as seen in FIG. 2C cannot be produced with a 'normal' two-dimensional display because the pixels' light field emits light isotopically. Instead it is necessary to exercise tight control on the angle and origin of the light emitted, for example, using a microlens array or other light field shaping layer such as a parallax barrier, or combination thereof. Following with the example of a microlens array for LFSL 106, FIG. 3A schematically illustrates a single light field pixel defined by a convex microlens 302 disposed at its focus from a corresponding subset of pixels in a digital pixel display 108 to produce a substantially collimated beam of light emitted by these pixels, whereby the direction of the beam is controlled by the location of the pixel(s) relative to the microlens. The single light field pixel produces a beam similar to that shown in FIG. 2C where the outside rays are lighter and the majority inside rays are darker. The digital pixel display 108 emits light which hits the microlens 302 and it results in a beam of substantially collimated light (A).

Figure 3B:
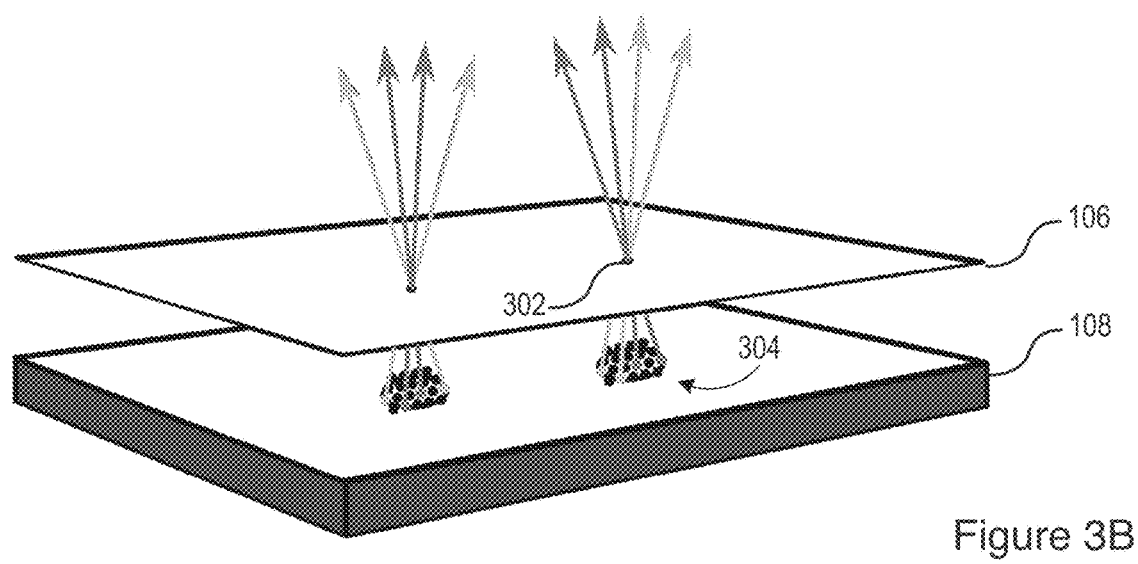

Accordingly, upon predictably aligning a particular microlens array with a pixel array, a designated "circle" of pixels will correspond with each microlens and be responsible for delivering light to the pupil through that lens. FIG. 3B schematically illustrates an example of a light field display assembly in which a LFSL 106 sits above a pixel display 108 to have pixels 304 emit light through the microlens array. A ray-tracing algorithm can thus be used to produce a pattern to be displayed on the pixel array below the microlens in order to create the desired virtual image that will effectively correct for the viewer's reduced visual acuity.

As will be detailed further below, the separation between the LFSL 106 and the pixel array 108 as well as the pitch of the lenses can be selected as a function of various operating characteristics, such as the normal or average operating distance of the display, and/or normal or average operating ambient light levels.

In some embodiments, LFSL 106 may be a microlens array (MLA) defined by a hexagonal array of microlenses or lenslet disposed so to overlay a corresponding square pixel array of digital pixel display 108. In doing so, while each microlens can be aligned with a designated subset of pixels to produce light field pixels as described above, the hexagonal-to-square array mismatch can alleviate certain periodic optical artifacts that may otherwise be manifested given the periodic nature of the optical elements and principles being relied upon to produce the desired optical image corrections. Conversely, a square microlens array may be favoured when operating a digital display comprising a hexagonal pixel array.

In some embodiments, the MLA may further or alternatively be overlaid or disposed at an angle (rotation) relative to the underlying pixel array, which can further or alternatively alleviate period optical artifacts.

In yet some further or alternative embodiments, a pitch ratio between the microlens array and pixel array may be deliberately selected to further or alternatively alleviate periodic optical artifacts. For example, a perfectly matched pitch ratio (i.e. an exact integer number of display pixels per microlens) is most likely to induce periodic optical artifacts, whereas a pitch ratio mismatch can help reduce such occurrences.

Accordingly, in some embodiments, the pitch ratio will be selected to define an irrational number, or at least, an irregular ratio, so to minimize periodic optical artifacts. For instance, a structural periodicity can be defined so to reduce the number of periodic occurrences within the dimensions of the display screen at hand, e.g. ideally selected so to define a structural period that is greater than the size of the display screen being used.

While this example is provided within the context of a microlens array, similar structural design considerations may be applied within the context of a parallax barrier, diffractive barrier or combination thereof. In some embodiments, light field display 104 can render dynamic images at over 30 frames per second on the hardware in a smartphone.

Accordingly, a display device as described above and further exemplified below, can be configured to render a corrected or adjusted image via the light field shaping layer that accommodates, tests or simulates for the user's visual acuity. By adjusting the image correction in accordance with the user's actual predefined, set or selected visual acuity level, different users and visual acuity may be accommodated using a same device configuration, whereas adjusting such parameters for a given user may allow for testing for or simulation of different corrective or visual adjustment solutions. For example, by adjusting corrective image pixel data to dynamically adjust a virtual image distance below/above the display as rendered via the light field shaping layer, different visual acuity levels may be accommodated, and that, for an image input as a whole, for distinctly various portions thereof, or again progressively across a particular input.

As noted in the examples below, in some embodiments, light field rendering may be adjusted to effectively generate a virtual image on a virtual image plane that is set at a designated distance from an input user pupil location, for example, so to effectively push back, or move forward, a perceived image, or portion thereof, relative to the light field refractor device 102. In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 5:
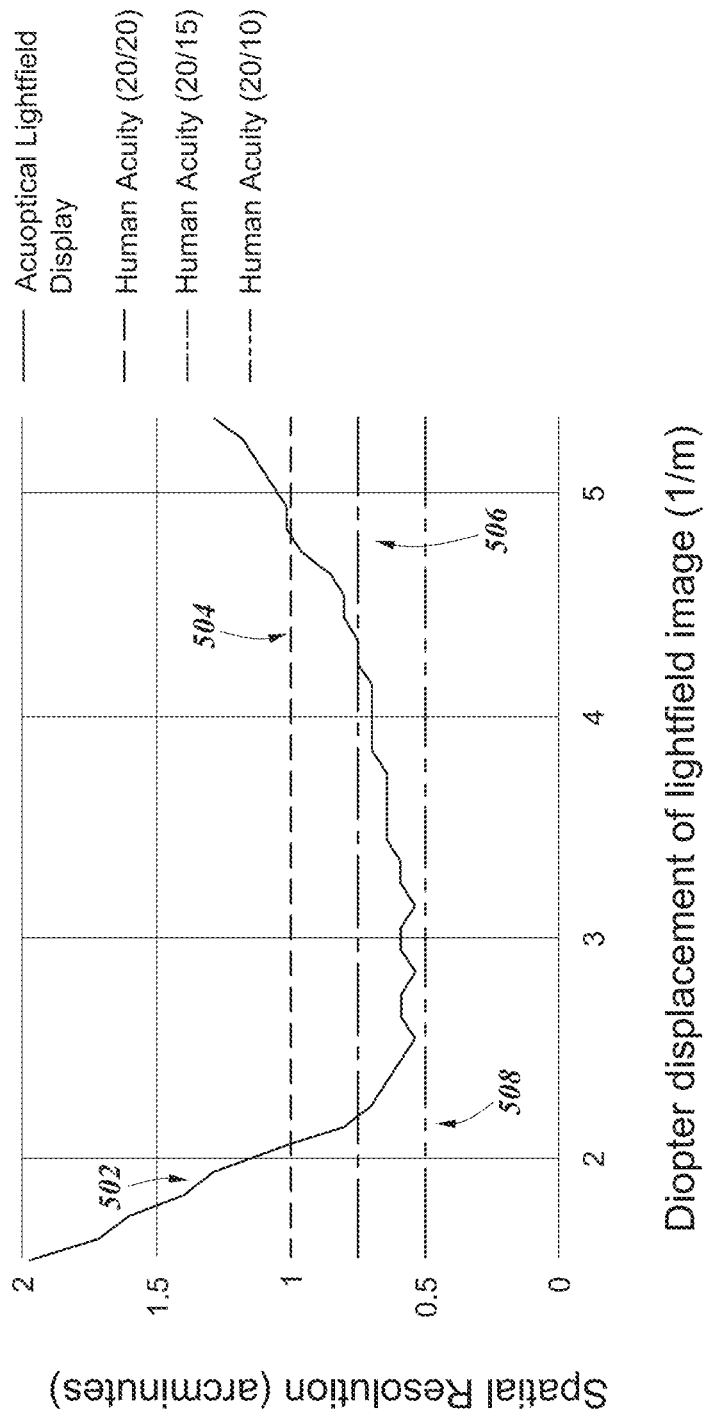
FIG. 5 is a plot of the angular resolution of an exemplary light field display as a function of the dioptric power generated, in accordance with one embodiment.

As an example of the effectiveness of the light field display in generating a diopter displacement (e.g. simulate the effect of looking through an optical component (i.e. a lens) of a given diopter strength or power) is shown in FIG. 5, where a plot is shown of the angular resolution (in arcminutes) of an exemplary light field display comprising a 1500 ppi digital pixel display, as a function of the dioptric power of the light field image (in diopters). From this plot, it is clear that, in this particular example, the light field display is able to generate displacements (line 502) in diopters that have higher resolution corresponding to 20/20 vision (line 504) or better (e.g. 20/15—line 506) and close to (20/10—line 508)), here within a dioptric power range of 2 to 2.5 diopters.

Thus, in the context of a refractor 102, light field display 104 may, according to different embodiments, be used to replace, at least in part, traditional optical components.

In some embodiments, the light field display can display a virtual image at optical infinity, meaning that any level of accommodation-based presbyopia (e.g. first order) can be corrected for. In some further embodiments, the light field display can both push the image back or forward, thus allowing for selective image corrections for both hyperopia (far-sightedness) and myopia (nearsightedness). In yet further embodiments as described below, variable displacements and/or accommodations may be applied as a function of non-uniform visual aberrations, or again to provide perceptive previewing or simulation of non-uniform or otherwise variable corrective powers/measures across a particular input or field of view.

However, the light field rendering system introduced above and the ray-tracing methods described below may also be used with other devices which may similarly comprise a light field display. For example, this may include a smartphone, tablets, e-readers, watches, televisions, GPS devices, laptops, desktop computer monitors, televisions, smart televisions, handheld video game consoles and controllers, vehicular dashboard and/or entertainment displays, and the like, without limitation.

Accordingly, any of the light field processing or ray-tracing methods described below, any modification thereto also discussed below, and related light field display solutions, can be equally applied to image perception adjustment solutions for visual media consumption, as they can for subjective vision testing solutions, or other technologically related fields of endeavour. As alluded to above, the light field display and rendering/ray-tracing methods discussed above may all be used to implement, according to various embodiments, a subjective vision testing device or system such as a phoropter or refractor. Indeed, a light field display may replace, at least in part, the various refractive optical components usually present in such a device. Thus, the vision correction light field ray tracing methods discussed below may equally be applied to render optotypes at different dioptric power or refractive correction by generating vision correction for hyperopia (far-sightedness) and myopia (nearsightedness), as was described above in the general case of a vision correction display. Light field systems and methods described herein, according to some embodiments, may be applied to create the same capabilities as a traditional instrument and to open a spectrum of new features, all while improving upon many other operating aspects of the device. For example, the digital nature of the light field display enables continuous changes in dioptric power compared to the discrete change caused by switching or changing a lens or similar; displaying two or more different dioptric corrections seamlessly at the same time; and, in some embodiments, the possibility of measuring higher-order aberrations and/or to simulate them for different purposes such as, deciding for free-form lenses, cataract surgery operation protocols, IOL choice, etc.

Going back to FIG. 1A, as producing a light field with angular resolution sufficient for accommodation correction over the full viewing 'zone' of a display would generally require an astronomically high pixel density, instead, a correct light field can be produced, in some embodiments, only at or around the location of the user's pupil(s). To do so, where a location or position of the user's eye is not otherwise rigidly constrained (e.g. within the context of a subject eye testing device or the like) the light field display can be paired with pupil tracking technology, as will be discussed below, to track a location of the user's eyes/pupils relative to the display. The display can then compensate for the user's eye location and produce the correct virtual image, for example, in real-time. Thus, in some embodiments, light field refractor 102 may include, integrated therein or interfacing therewith, a pupil/eye tracking system 110 to improve or enhance corrective image rendering by tracking a location of the user's eye(s)/pupil(s) (e.g. both or one, e.g. dominant, eye(s)) and adjusting light field corrections accordingly one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying a tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). As mentioned above, in some embodiments, such eye/pupil tracking hardware/software may be integral to device 102, for instance, operating in concert with integrated components such as one or more front facing camera(s), onboard IR/NIR light source(s) (not shown) and the like. In other user environments, such as in a vehicular environment, eye/pupil tracking hardware may be further distributed within the environment, such as dash, console, ceiling, windshield, mirror or similarly-mounted camera(s), light sources, etc.

Figure 4A:
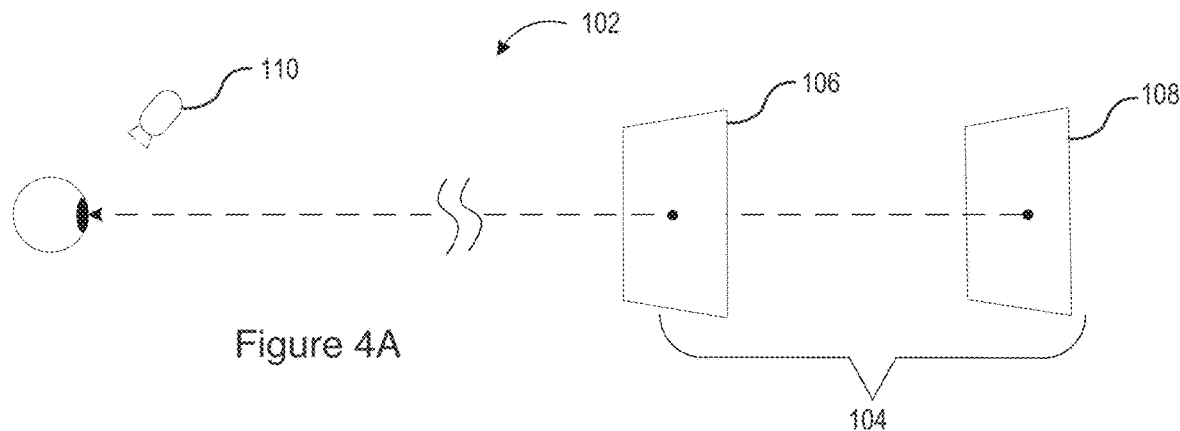
FIGS. 4A to 4C are schematic diagrams of exemplary light field vision testing or previewing systems (e.g. refractors/phoropters), in accordance with different embodiments.
Figure 4B:
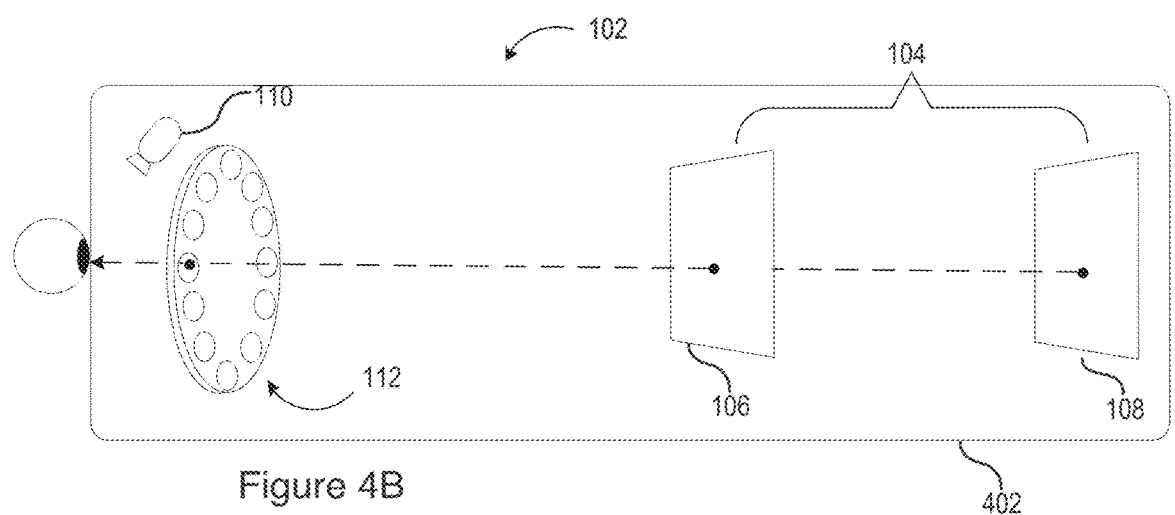
Figure 4C:
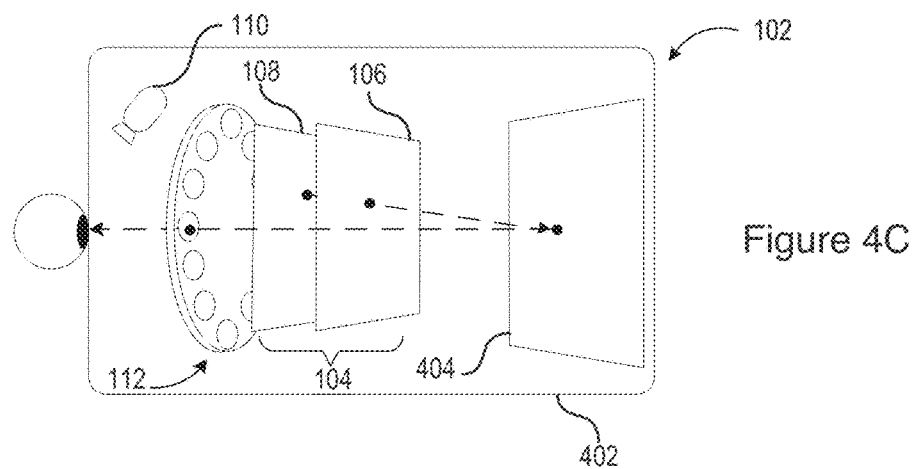

In one embodiment and as illustrated in FIG. 4A, light field refractor 102 may be configured with light field display 104 located relatively far away (e.g. one or more meters) from the user's eye currently being diagnosed. Note that the pointed line in FIGS. 4A to 4C is used to schematically illustrate the direction of the light rays emitted by light field display 104. Also illustrated is eye-tracker 110, which may be provided as a physically separate element, for example, installed in at a given location in a room or similar. In some embodiments, the noted eye/pupil tracker 110 may include the projection of IR markers/patterns to help align the patient's eye with the light field display. In some embodiments, a tolerance window (e.g. "eye box") may be considered to limit the need to refresh the ray-tracing iteration. An exemplary value of the size of the eye box, in some embodiments, is around 6 mm, though smaller (e.g. 4 mm) or larger eye boxes may alternatively be set to impact image quality, stability or like operational parameters.

Going back to FIG. 1A, light field refractor 102 may also comprise, according to different embodiments and as will be further discussed below, one or more refractive optical components 112, a processing unit 114, a data storage unit or internal memory 116, one or more cameras 118, a power source 120, a network interface 122 for communicating via network to a remote database or server 124.

In some embodiments, power source 120 may comprise, for example, a rechargeable Li-ion battery or similar. In some embodiments, it may comprise an additional external power source, such as, for example, a USB-C external power supply. It may also comprise a visual indicator (screen or display) for communicating the device's power status, for example whether the device is on/off or recharging.

In some embodiments, internal memory 116 may be any form of electronic storage, including a disk drive, optical drive, read-only memory, random-access memory, or flash memory, to name a few examples. In some embodiments, a library of chart patterns (Snellen charts, prescribed optotypes, forms, patterns, or other) may be located in internal memory 116 and/or retrievable from remote server 124 via network interface 122.

Figure 6A:
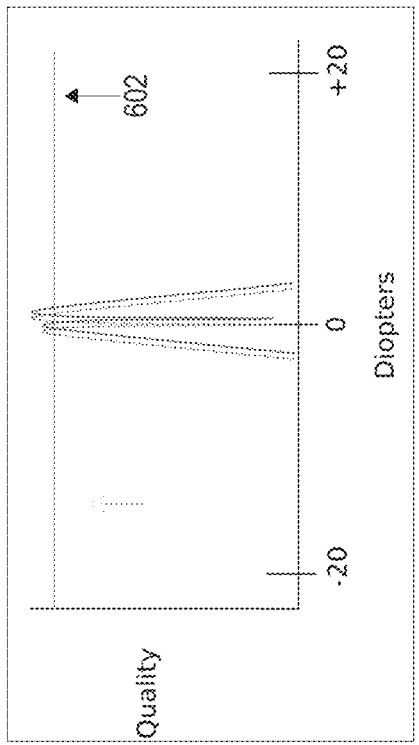
FIGS. 6A to 6D are schematic plots of the image quality generated by a light field refractor/phoropter as a function of the dioptric power generated by using in combination with the light field display (A) no refractive component, (B) one refractive component, (C) and (D) a multiplicity of refractive components.
Figure 6B:
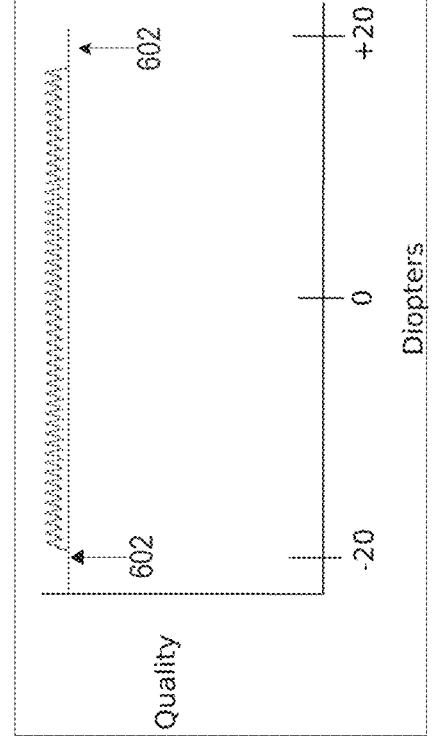

In some embodiments, one or more optical components 112 may be used in combination with the light field display 104, for example to shorten the size of refractor 102 and still offer an acceptable range in dioptric power. The general principle is schematically illustrated in the plots of FIGS. 6A to 6D. In these schematic plots, the image quality (e.g. inverse of the angular resolution, higher is better) at which optotypes are small enough to be useful for vision testing in this plot is above horizontal line 602 which represents typical 20/20 vision. FIG. 6A shows the plot for the light field display only, where we see the characteristic two peaks corresponding to the smallest resolvable point, one of which was plotted in FIG. 5 (here inverted and shown as a peak instead of a basin), and where each region above the line may cover a few diopters of dioptric power, according to some embodiments. While the dioptric range may, in some embodiments, be more limited than needed when relying only on the light field display, it is possible to shift this interval by adding one or more refractive optical components. This is shown in FIG. 6B where the regions above the line 602 is shifted to the left (negative diopters) by adding a single lens in the optical path.

Figure 6C:
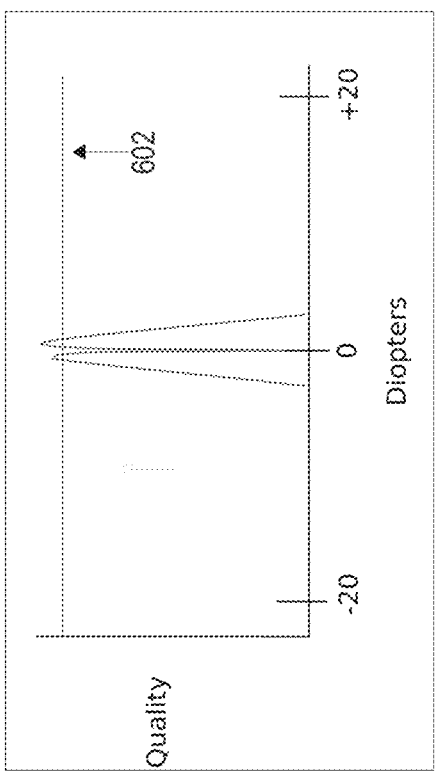
Figure 6D:
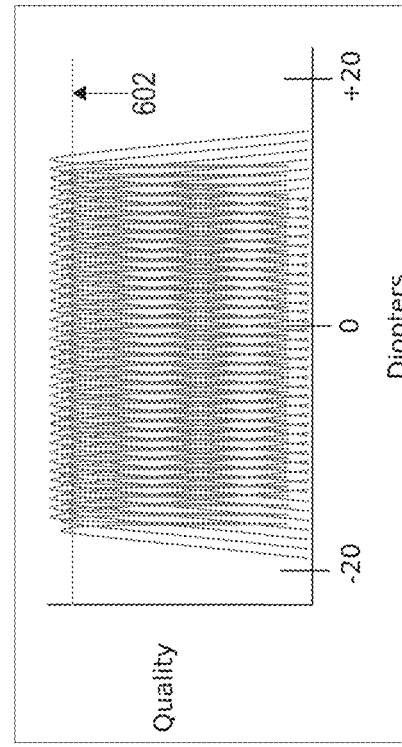

Thus, by using a multiplicity of refractive optical components 112 or by alternating sequentially between different refractive components 112 of increasing or decreasing dioptric power, it is possible to shift the center of the light field diopter range to any required value, as shown in FIG. 6C, and thus the image quality may be kept above line 602 for any required dioptric power as shown in FIG. 6D. In some embodiments, a range of 30 diopters from +10 to −20 may be covered for example. In the case of one or more reels of lenses, the lens may be switched for a given larger dioptric power increment, and the light field display would be used to provide a finer continuous change to accurately pin-point the required total dioptric power required to compensate for the patient's reduced visual acuity. This would still result in light field refractor 102 having a reduced number of refractive optical components compared to the number of components needed in a traditional refractor, while drastically enhancing the overall fine-tuning ability of the device.

One example, according to one embodiment, of such a light field refractor 102 is schematically illustrated in FIG. 4B, wherein the light field display 104 (herein shown comprising LFSL 106 and digital pixel display 108) is combined with a multiplicity of refractive components 112 (herein illustrated as a reel of lenses as an example only). By changing the refractive component used in combination with light field display 104, a larger dioptric range may be covered. This may also provide means to reduce the dimension of device 102 as mentioned above, making it more portable, so that all its internal components may be encompassed into a shell, housing or casing 402. In some embodiments, light field refractor 102 may thus comprise a durable ABS housing that may be shock and harsh-environment resistant. In some embodiments, light field refractor 102 may also comprise a telescopic feel for fixed or portable usage; optional mounting brackets, and/or a carrying case (not shown). In some embodiments, all components may be internally protected and sealed from the elements.

In some embodiments, casing 402 may further comprise a head-rest or similar (not shown) to keep the user's head still and substantially in the same location, thus, in such examples, foregoing the general utility of a pupil tracker or similar techniques by substantially fixing a pupil location relative to this headrest.

In some embodiments, it may also be possible to further reduce the size of device 102 by adding, for example, a mirror or any device which may increase the optical path. This is illustrated in FIG. 4C where the length of the device was reduced by adding a mirror 404. This is shown schematically by the pointed arrow which illustrates the light being emitted from pixel display 108 travelling through LFSL 106 before being reflected back by mirror through refractive components 112 and ultimately hitting the eye.

The skilled technician will understand that different examples of refractive components 112 may be include, without limitation, one or more lenses, sometimes arranged in order of increasing dioptric power in one or more reels of lenses similar to what is typically found in traditional refractors/phoropters; an electrically controlled fluid lens; active Fresnel lens; and/or Spatial Light Modulators (SLM). In some embodiments, additional motors and/or actuators (not shown) may be used to operate refractive components 112. The motors/actuators may be communicatively linked to processing unit 114 and power source 120, and operate seamlessly with light field display 102 to provide the required dioptric power.

Figure 7A:
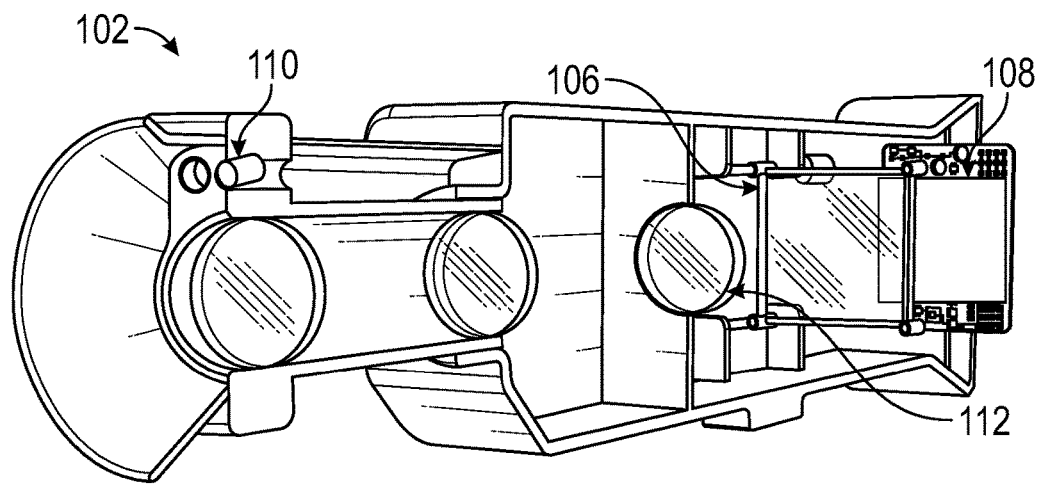
FIGS. 7A, 7B and 7C are perspective views of exemplary light field refractors/phoropters, showing a casing thereof in cross-section (A and B) and a unit combining side-by-side two of the units (C) shown in 7A and 7B, in accordance with one embodiment.
Figure 7B:
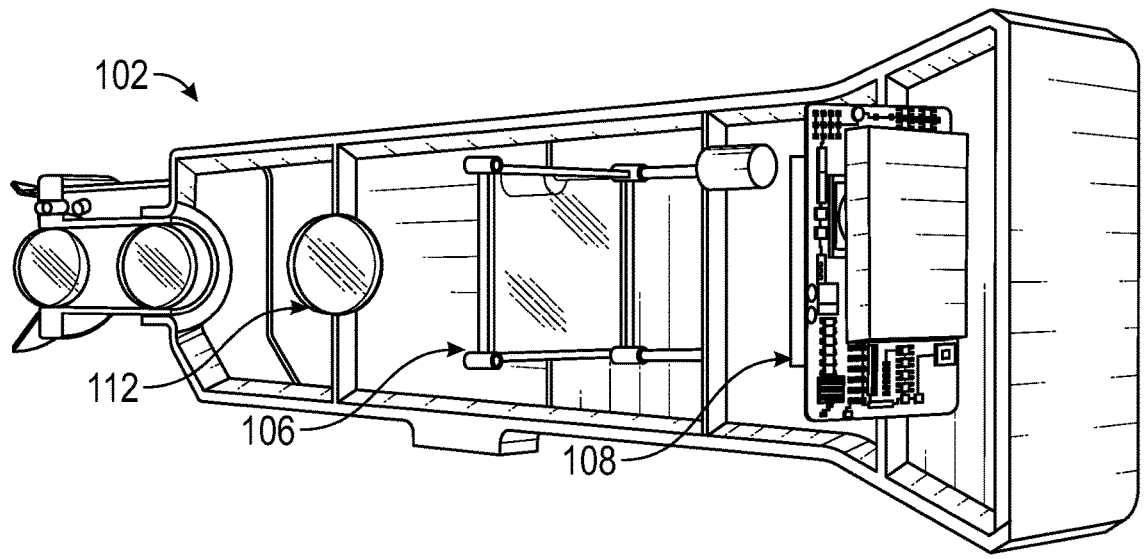

For example, FIGS. 7A and 7B show a perspective view of an exemplary light field phoropter 102 similar to the one schematically shown in FIG. 3B, but wherein the refractive component 112 is an electrically tunable liquid lens. Thus, in this particular embodiment, no mechanical or moving component are used, which may result in the device being more robust. In some embodiments, the electrically tunable lens may have a range of ±13 diopters.

In one illustrative embodiment, a 1000 dpi display is used with a MLA having a 65 mm focal distance and 1000 μm pitch with the user's eye located at a distance of about 26 cm. A similar embodiment uses the same MLA and user distance with a 3000 dpi display.

Other displays having resolutions including 750 dpi, 1000 dpi, 1500 dpi and 3000 dpi were also tested or used, as were MLAs with a focal distance and pitch of 65 mm and 1000 μm, 43 mm and 525 μm, 65 mm and 590 μm, 60 mm and 425 μm, 30 mm and 220 μm, and 60 mm and 425 μm, respectively, and user distances of 26 cm, 45 cm or 65 cm.

Going back to FIG. 1A, in some embodiments, eye-tracker 110 may further comprise a digital camera, in which case it may be used to further acquire images of the user's eye to provide further diagnostics, such as pupillary reflexes and responses during testing for example. In other embodiments, one or more additional cameras 118 may be used to acquire these images instead. In some embodiments, light field refractor 102 may comprise built-in stereoscopic tracking cameras.

In some embodiments, feedback and/or control of the vision test being administered by system 100 may be given via a control interface 126. In some embodiments, the control interface 126 may comprise a dedicated handheld controller-like device 128. This controller 128 may be connected via a cable or wirelessly, and may be used by the patient directly and/or by an operator like an eye professional. In some embodiments, both the patient and operator may have their own dedicated controller 128. In some embodiments, the controller may comprise digital buttons, analog thumbstick, dials, touch screens, and/or triggers.

In some embodiments, control interface 126 may comprise a digital screen or touch screen, either on refractor 102 itself or part of an external module (not shown). In other embodiments, control interface 126 may let on or more external remote devices (i.e. computer, laptop, tablet, smartphone, remote, etc.) control light field refractor 102 via network interface 122. For example, remote digital device 130 may be connected to light field refractor 102 via a cable (e.g. USB cable, etc.) or wirelessly (e.g. via Wi-Fi, Bluetooth or similar) and interface with light field refractor 102 via a dedicated application, software or website (not shown). Such a dedicated application may comprise a graphical user interface (GUI), and may also be communicatively linked to remote database 124.

In some embodiments, the user or patient may give feedback verbally and the operator may control the vision test as a function of that verbal feedback. In some embodiments, refractor 102 may comprise a microphone (not shown) to record the patient's verbal communications, either to communicate them to a remote operator via network interface 122 or to directly interact with the device (e.g. via speech recognition or similar).

Going back to FIG. 1A, processing unit 114 may be communicatively connected to data storage 116, eye tracker 110, light field display 104 and refractive components 112. Processing unit 114 may be responsible for rendering one or more images or optotypes via light field display 104 and, in some embodiments, jointly control refractive components 112 to achieve a required total change in dioptric power. It may also be operable to send and receive data to internal memory 116 or to/from remote database 124 via network interface 122.

In some embodiments, diagnostic data may be automatically transmitted/communicated to remote database 124 or remote digital device 130 via network interface 122 through the use of a wired or wireless network connection. The skilled artisan will understand that different means of connecting electronic devices may be considered herein, such as, but not limited to, Wi-Fi, Bluetooth, NFC, Cellular, 2G, 3G, 4G, 5G or similar. In some embodiments, the connection may be made via a connector cable (e.g. USB including microUSB, USB-C, Lightning connector, etc.). In some embodiments, remote digital device 130 may be located in a different room, building or city.

Figure 7C:
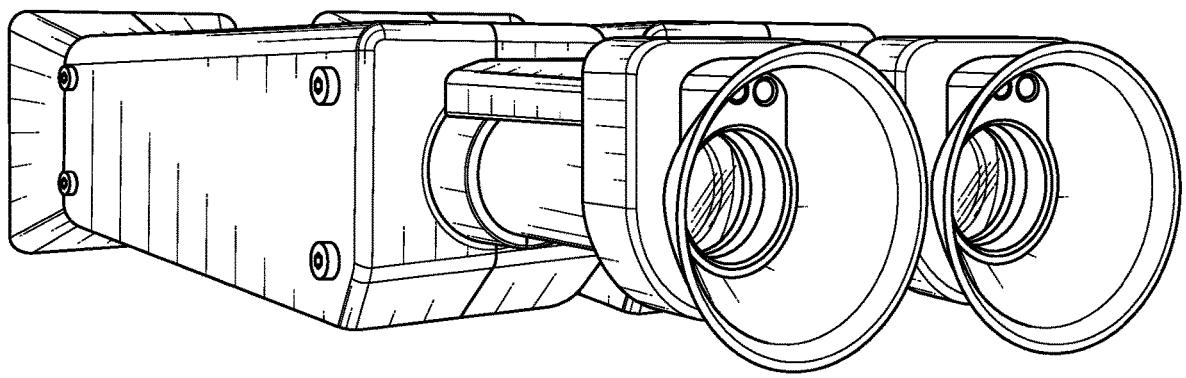

In some embodiments, two light field refractors 102 may be combined side-by-side to independently measure the visual acuity of both left and right eye at the same time. An example is shown in FIG. 7C, where two units corresponding to the embodiment of FIG. 7A or 7B (used as an example only) are placed side-by-side or fused into a single device 702. Thus, such a binocular light field refractor device 702 would comprise, in some embodiments, every element described above with respect to monocular refractor 102 (e.g. in FIG. 1A) but further includes two sets of light field displays 104 and refractive components 112 instead of one (one for each eye). In some embodiments, instead of having a distinct light field display 104 for each eye, as shown in FIG. 7C, a single light field display operable to project light field images to both eyes simultaneously may be used as well. In some embodiments, it may also comprise two eye trackers 110, again one for each eye, or it may use a single eye tracker 110 to track both eyes simultaneously. Below, it will be understood that any embodiment of refractor 102 or improvements thereto, including the addition of optical components, described above or below may equally apply as well to each left and right portions of refractor 702, without restriction. In some embodiments, refractor 702 may be used to do monocular vision testing, just like refractor 102, but it may also be used to project a same image to both eyes simultaneously, as will be discussed further below.

In some embodiments, a dedicated application, software or website may provide integration with third party patient data software. In some embodiments, software required to operate and installed on refractor 102 may be updated on-the-fly via a network connection and/or be integrated with the patient's smartphone app for updates and reminders.

In some embodiments, the dedicated application, software or website may further provide a remote, real-time collaboration platform between an eye professional and user/patient, and/or between different eye professionals. This may include interaction between different participants via video chat, audio chat, text messages, etc.

In some embodiments, light field refractor 102 may be self-operated or operated by an optometrist, ophthalmologist or other certified eye-care professional. For example, in some embodiments, a user/patient may use refractor 102 in the comfort of his/her own home, in a store or a remote location.

Figure 8:
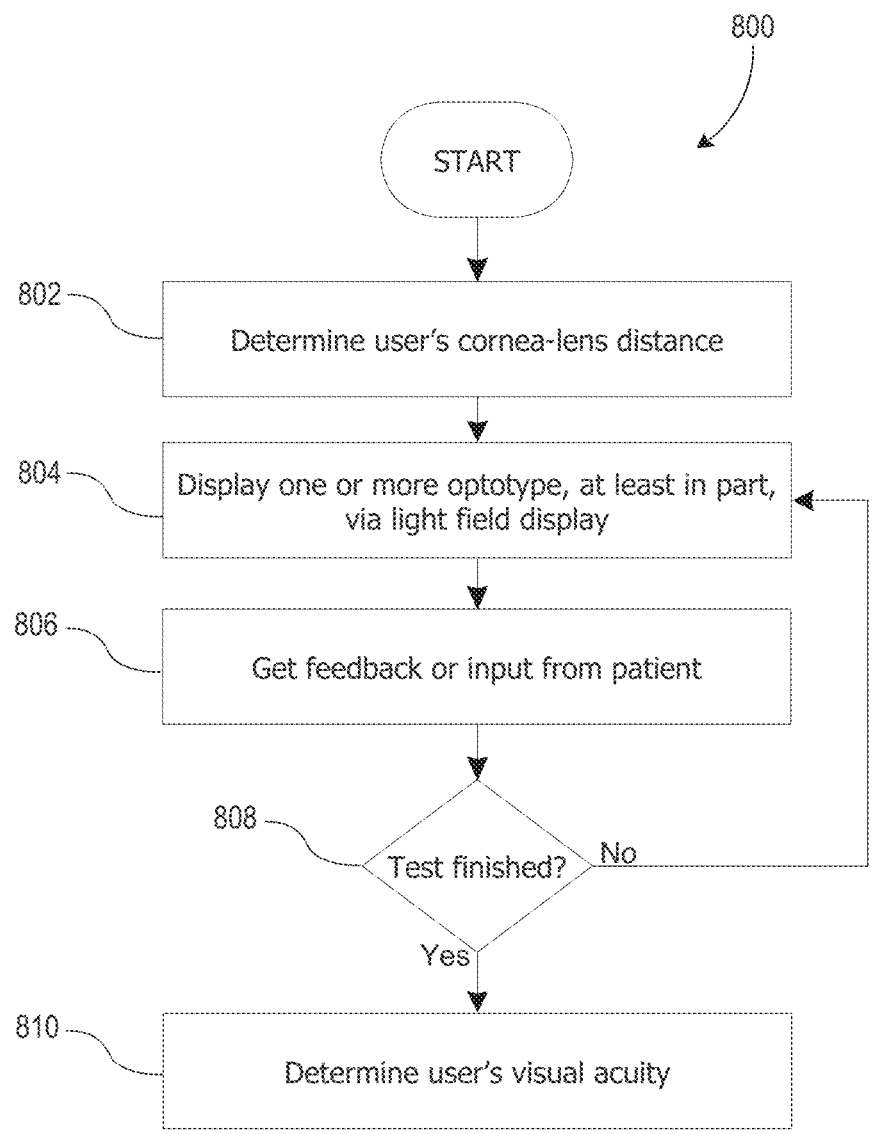
FIG. 8 is a process flow diagram of an exemplary dynamic subjective vision testing method, in accordance with one embodiment.

With reference to FIG. 8 and in accordance with one exemplary embodiment, a dynamic subjective vision testing method using vision testing system 100, generally referred to using the numeral 800, will now be described. As mentioned above, the use of a light field display enables refractor 102 to provide more dynamic and/or more modular vision tests than what is generally possible with traditional refractors/phoropters. Generally, method 800 seeks to diagnose a patient's reduced visual acuity and produce therefrom, in some embodiments, an eye prescription or similar.

In some embodiments, eye prescription information may include, for each eye, one or more of: distant spherical, cylindrical and/or axis values, and/or a near (spherical) addition value.

In some embodiments, the eye prescription information may also include the date of the eye exam and the name of the eye professional that performed the eye exam. In some embodiments, the eye prescription information may also comprise a set of vision correction parameter(s), as will be further discussed below, for operating any vision correction light field displays using the systems and methods described below. In some embodiments, the eye prescription may be tied to a patient profile or similar, which may contain additional patient information such as a name, address or similar. The patient profile may also contain additional medical information about the user. All information or data (i.e. set of vision correction parameter(s), user profile data, etc.) may be kept on external database 124. Similarly, in some embodiments, the user's current vision correction parameter(s) may be actively stored and accessed from external database 124 operated within the context of a server-based vision correction subscription system or the like, and/or unlocked for local access via the client application post user authentication with the server-based system.

Refractor 102 being, in some embodiments, portable, a large range of environments may be chosen to deliver the vision test (home, eye practitioner's office, etc.). At the start, the patient's eye may be placed at the required location. This may be done by placing his/her head on a headrest or by placing the objective (i.e. eyepiece) on the eye to be diagnosed. As mentioned above, the vision test may be self-administered or partially self-administered by the patient. For example, the operator (e.g. eye professional or other) may have control over the type of test being delivered, and/or be the person who generates or helps generate therefrom an eye prescription, while the patient may enter inputs dynamically during the test (e.g. by choosing or selecting an optotype, etc.).

As will be discussed below, light field rendering methods described herein generally requires an accurate location of the patient's pupil center. Thus, at step 802, such a location is acquired. In some embodiments, such a pupil location may be acquired via eye tracker 110, either once, at intervals, or continuously. In other embodiments, the location may be derived from the device or system's dimension. For example, in some embodiments, the use a head-rest and/or an eye-piece or similar provides an indirect means of deriving the pupil location. In some embodiments, refractor 102 may be self-calibrating and not require any additional external configuration or manipulation from the patient or the practitioner before being operable to start a vision test.

At step 804, one or more optotypes is/are displayed to the patient, at one or more dioptric power (e.g. in sequence, side-by-side, or in a grid pattern/layout). The use of light field display 104 offers multiple possibilities regarding how the images/optotypes are presented, and at which dioptric power each may be rendered. The optotypes may be presented sequentially at different dioptric power, via one or more dioptric power increments. In some embodiments, the patient and/or operator may control the speed and size of the dioptric power increments.

Figure 9:
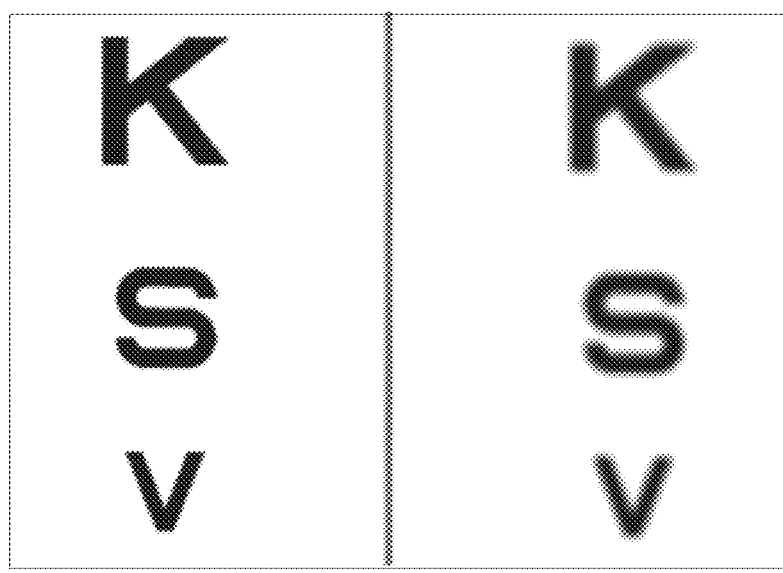
FIG. 9 is a schematic diagram of an exemplary light field image showing two columns of optotypes at different dioptric power for the method of FIG. 8, in accordance with one embodiment.

In some embodiments, optotypes may also be presented, at least in part, simultaneously on the same image but rendered at a different dioptric power. For example, FIG. 9 shows an example of how different optotypes may be displayed to the patient but rendered with different dioptric powers simultaneously. These may be arranged in columns or in a table or similar. In FIG. 9, we see two columns of three optotypes (K, S, V), varying in size, as they are perceived by a patient, each column being rendered at different degrees of refractive correction (e.g. dioptric power). In this specific example, the optotypes on the right are being perceived as blurrier than the optotypes on the left.

Thus, at step 806, the patient would communicate/verbalize this information to the operator or input/select via, for example, control interface 126 the left column as the one being clearer. Thus, in some embodiments, method 800 may be configured to implement dynamic testing functions that dynamically adjust one or more displayed optotype's dioptric power in real-time in response to a designated input, herein shown by the arrow going back from step 808 to step 804 in the case where at step 808, the user or patient communicates that the perceived optotypes are still blurry or similar. In the case of sequentially presented optotypes, the patient may indicate when the optotypes shown are clearer. In some embodiments, the patient may control the sequence of optotypes shown (going back and forth as needed in dioptric power), and the speed and increment at which these are presented, until he/she identifies the clearest optotype. In some embodiments, the patient may indicate which optotype or which group of optotypes is the clearest by moving an indicator icon or similar within the displayed image.

In some embodiments, the optotypes may be presented via a video feed or similar.

In some embodiments, when using a reel of lenses or similar (for refractive components 112), discontinuous changes in dioptric power may be unavoidable. For example, the reel of lenses may be used to provide a larger increment in dioptric power, as discussed above. Thus, step 804 may in this case comprise first displaying larger increments of dioptric power by changing lens as needed, and when the clearest or less blurry optotypes are identified, fine-tuning with continuous or smaller increments in dioptric power using the light field display. In the case of optotypes presented simultaneously, the refractive components 112 may act on all optotypes at the same time, and the change in dioptric power between them may be controlled only by the light display 104. In some embodiments, for example when using an electrically tunable fluid lens or similar, the change in dioptric power may be continuous.

In some embodiments, eye images may be recorded during steps 802 to 806 and analyzed to provide further diagnostics. For example, eye images may be compared to a bank or database of proprietary eye exam images and analyzed, for example via an artificial intelligence (AI) or Machine-learning (ML) system or similar. This analysis may be done by refractor 102 locally or via a remote server or database 124.

Once the correct dioptric power needed to correct for the patient's reduced visual acuity is defined at step 810, an eye prescription or vision correction parameter(s) may be derived from the total dioptric power used to display the best perceived optotypes.

In some embodiments, the patient, an optometrist or other eye-care professional may be able to transfer the patient's eye prescription directly and securely to his/her user profile store on said server or database 124. This may be done via a secure website, for example, so that the new prescription information is automatically uploaded to the secure user profile on remote database 124. In some embodiments, the eye prescription may be sent remotely to a lens specialist or similar to have prescription glasses prepared.

In some embodiments, vision testing system 100 may also or alternatively be used to simulate compensation for higher-order aberrations. Indeed, the light field rendering methods described above may be used to compensation for higher order aberrations (HOA), and thus be used to validate externally measured or tested HOA via method 3600, in that a measured, estimated or predicted HOA can be dynamically compensated for using the system described herein and thus subjectively visually validated by the viewer in confirming whether the applied HOA correction satisfactory addresses otherwise experienced vision deficiencies.

Ray Tracing

With reference to FIGS. 10A to 17D, and in accordance with different embodiments, an exemplary computationally implemented ray-tracing method for rendering an adjusted image via an array of light field shaping elements, in this example provided by a light field shaping layer (LFSL) disposed relative to a set of underlying display pixels, that accommodates or compensates for the user's reduced visual acuity will now be described. In this first example, for illustrative purposes, adjustment of a single image (i.e. the image as whole) is being implemented without consideration for distinct image portions and taking only into account spherical dioptric power changes.

Figure 10A:
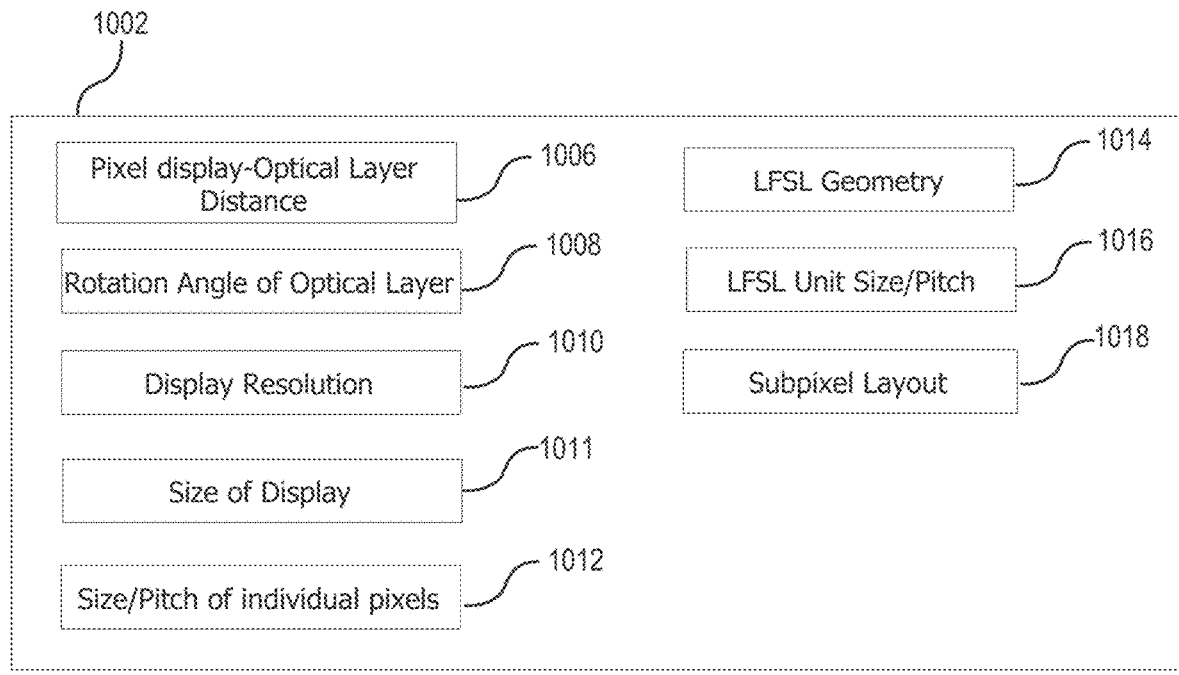
FIGS. 10A and 10B are process flow diagrams of exemplary input constant parameters and variables, respectively, for the ray-tracing rendering process of FIG. 11, in accordance with one embodiment.

In this exemplary embodiment and as shown in FIG. 10A, a set of constant parameters 1002 used for the light field rendering process may be pre-determined. These may include, for example, any data or parameters that are not expected to significantly change during a user's viewing session, between different viewing sessions or even between users, for instance. These may generally be based on the physical and functional characteristics of light field display 104 for which the method is to be implemented, as will be explained below. Similarly, as shown in FIG. 10B, every iteration of the rendering algorithm (i.e. when rendering a full light field image frame) may also use a set of input variables 1004 which are expected to change either at each rendering iteration (i.e. between frames) or at least between each user's viewing session.

As illustrated in FIG. 10A, the list of constant parameters 1002 may include, without limitations, the distance 1006 between pixel display 108 and the LFSL 106, the in-plane rotation angle 1008 between the frames of reference digital pixel display 108 and LFSL 106, the resolution 1010 and/or size 1011 of digital pixel display 108, the size 1012 of each individual pixel, the optical geometry 1014 of LFSL 106, the size or pitch of individual optical elements or units 1016 within LFSL 106 and optionally the subpixel layout 1018 of pixel display 108. Moreover, both the resolution 1010 and the size of each individual pixel 1012 of pixel display 108 may be used to pre-determine both the absolute size of the display in real units (i.e. in mm) and the three-dimensional position/location of each pixel within the display. In some embodiments where the subpixel layout 1018 is available, the position/location within pixel display 108 of each subpixel may also be pre-determined. These three-dimensional location/positions are usually calculated using a given frame of reference located somewhere within the plane of pixel display 108, for example a corner or the middle of the display, although other reference points may be chosen. Concerning the optical layer geometry 1014, different geometries may be considered, for example a hexagonal geometry. Finally, by combining the distance 1006, the rotation angle 1008, and the geometry 1014 with the optical element size 1016, it is possible to similarly pre-determine the three-dimensional location/position of each optical element of LFSL 106 with respect to the frame of reference of pixel display 108.

Figure 10B:
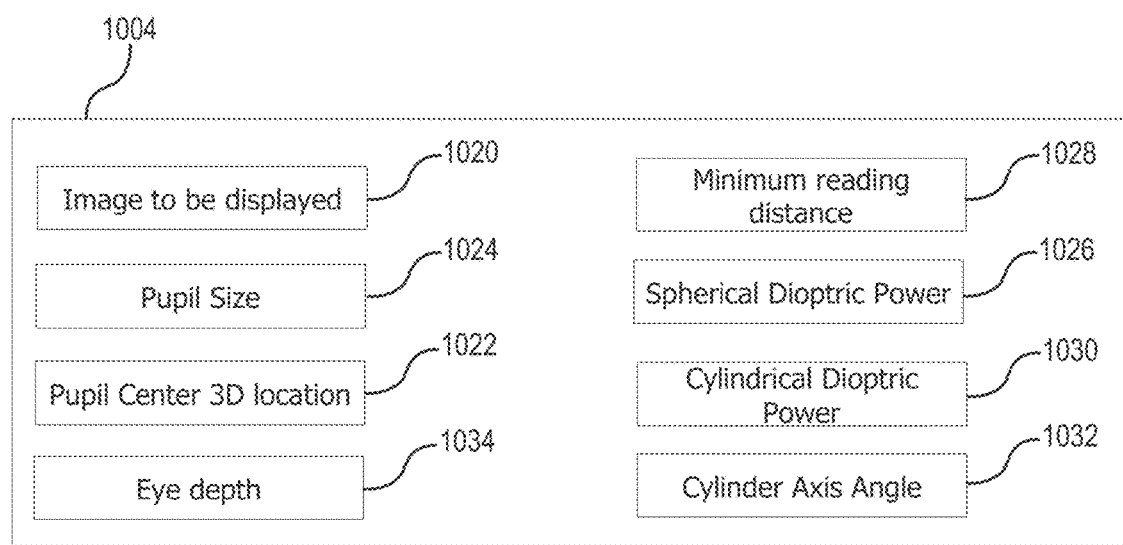

FIG. 10B meanwhile illustratively lists an exemplary set of input variables 1004 that may be used for the light field rendering methods described below, and may include any input data that may reasonably change during a user's single viewing session, for example between each image frame, or between different viewing sessions or even between different users (e.g. not related to the hardware specifications of light field display 104 or refractor 102). These may be automatically acquired by device 102 during normal operation or be inputted (for example by a user or person operating the device for the user) into the device as required. They may thus include without limitation: the image(s)/optotype(s) to be displayed 1020 (e.g. comprising pixel data such as on/off, colour, brightness, etc.), a three-dimensional pupil center location 1022 (e.g. in embodiments implementing active eye/pupil tracking methods) and/or a pupil size 1024.

The methods described below, according to different embodiments, also requires vision correction parameters in the form of dioptric power so as to modulate the strength and nature of the compensation/correction generated by the light field image. These may include a spherical dioptric power 1026 (which may be derived indirectly, for example, from a minimum reading distance value 1028 as will be discussed below), but also, in some embodiments, one or more sets of a cylindrical power 1030 and a corresponding cylindrical axis angle 1032. In some embodiments, these input variables (spherical dioptric power 1026, cylindrical dioptric power 1026 and cylinder axis angle 1030) mirror the SPHERE, CYL and AXIS parameters used in a typical eye examination.

Moreover, in some embodiments, an eye depth value 1034 may also be used, either as an average value or customized for an individual user. In some embodiments, input image 1020, may be representative of one or more digital images to be displayed with digital pixel display 108. In addition, input image 1020 may generally be encoded in any data format used to store digital images known in the art.

Pupil center location 1022, in one embodiment, is the three-dimensional coordinates of at least one the user's pupils' center with respect to a given reference frame, for example a point on device 102 or digital pixel display 108 and may be derived from any eye/pupil tracking method known in the art via eye/pupil tracker 110. In some embodiments, the pupil center location 1022 may be determined prior to any new iteration of the rendering algorithm, or in other cases, at a lower framerate (and thus re-use the same location/position for two or more subsequent image frames). In some embodiments, only the pupil center location of a single user's eye may be determined, for example the user's dominant eye (i.e. the one that is primarily relied upon by the user). In some embodiments, this location/position, and particularly the associated pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1028 is defined as the minimal focus distance for reading that the user's eye(s) may be able to accommodate (i.e. able to view without discomfort). In some embodiments, different values of the minimum reading distance 1028 associated with different users may be entered, for example, as can other adaptive vision correction parameters be considered depending on the application at hand and vision correction being addressed. As mentioned above, in some embodiments, minimum reading distance 1028 may be derived from an eye prescription (e.g. glasses prescription or contact prescription) or similar. It may, for example, correspond to the near point distance corresponding to the uncorrected user's eye, which can be calculated from the prescribed corrective lens power assuming that the targeted near point was at 25 cm.

With added reference to FIGS. 11 to 16D, parameters 1002 and variables 1004 may be used in the light field ray-tracing method 1100, herein presented in accordance with different embodiments. While method 1100 and the steps described in FIG. 12 apply equally to both embodiments, steps 1102 and 1112 may be applied using either virtual image planes "virtually" located behind the display or on the retinal plane (via an eye focal plane (i.e. inside the eye)).

Moreover, method 1100 as illustrated in FIGS. 11 to 17D is designed to correct for spherical aberrations.

Moreover, for illustrative purposes, in this example, adjustment of a single image (i.e. the image as whole) is being implemented without consideration for distinct image portions. Further examples below will specifically address modification of the following example for adaptively adjusting distinct image portions.

Figure 11:
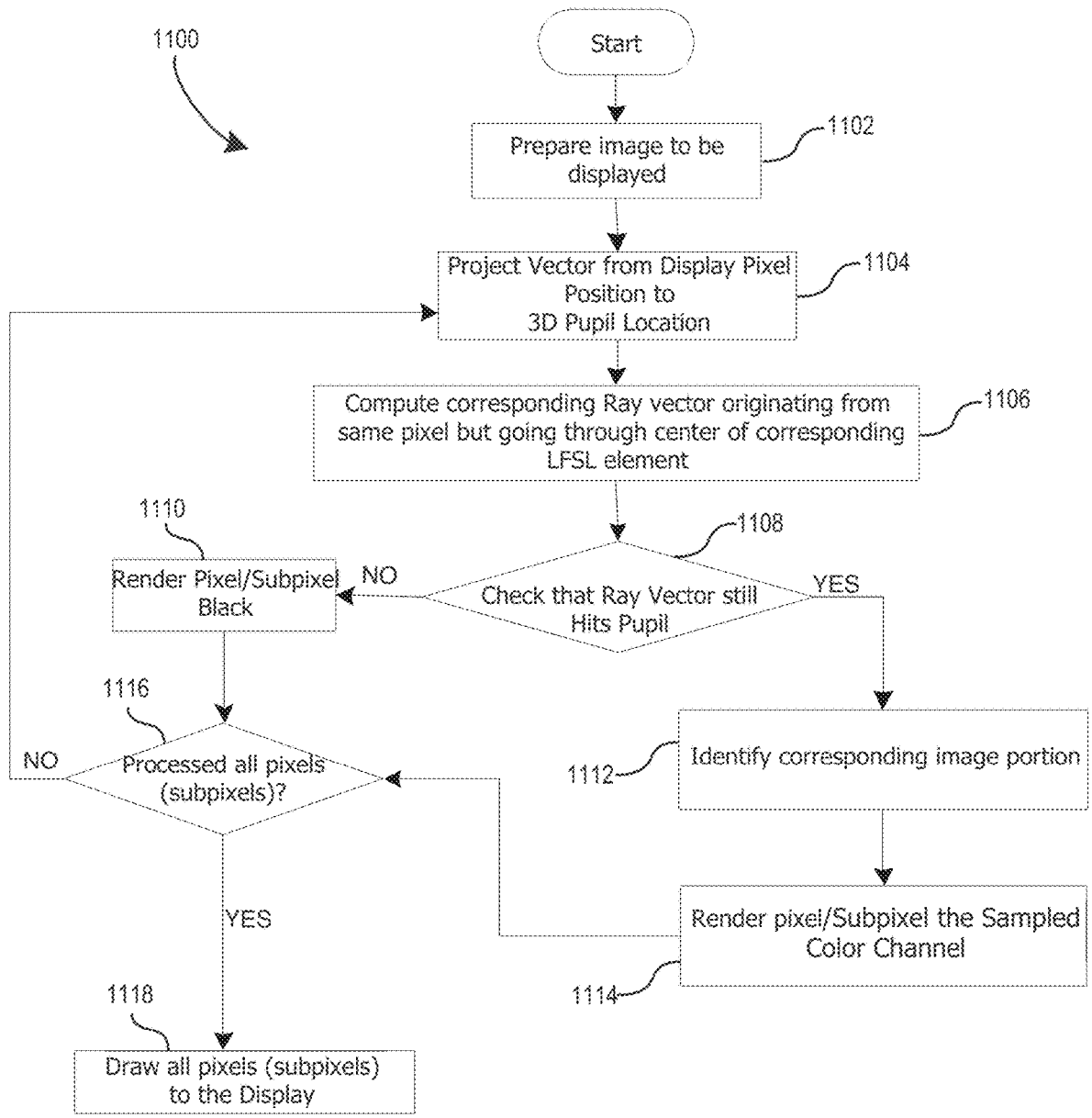
FIG. 11 is a process flow diagram of an illustrative ray-tracing rendering process, in accordance with one embodiment.
Figure 12:
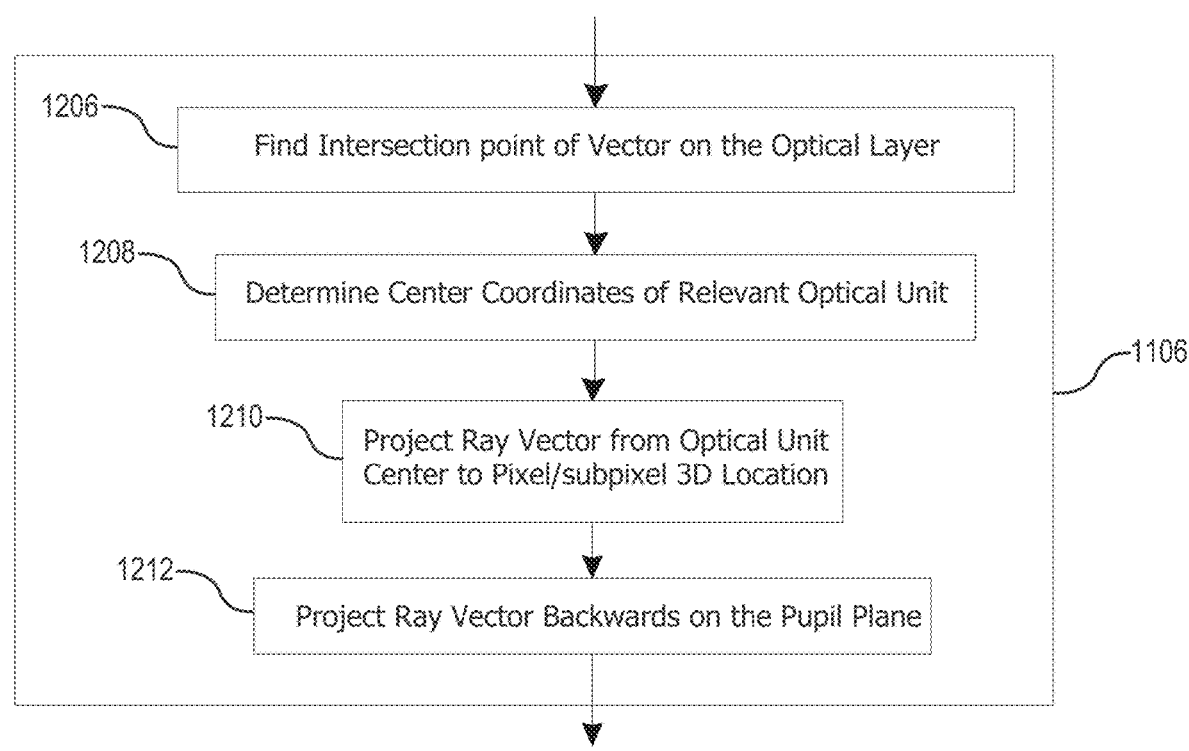
FIG. 12 is a process flow diagram illustrating a process step of FIG. 11, in accordance with one embodiment.

In the illustrated embodiment of FIG. 11, method 1100 begins with step 1102, in which the image to be displayed is pre-processed for subsequent ray-tracing steps. This includes numerically computing a location or position for a corresponding adjusted image surface or plane that corresponds to the required spherical dioptric power 1026 on which the image to be displayed will be mapped.

An exemplary ray-tracing methodology is described in steps 1104 to 1118 of FIG. 11, at the end of which the output color of each pixel of pixel display 108 is known so as to virtually reproduce the light field emanating from an input image 1020 positioned at the adjusted image plane. In FIG. 11, these steps are illustrated as a loop over each pixel in pixel display 108, so that each of steps 1104 to 1116 describes the computations done for each individual pixel. However, in some embodiments, these computations need not be executed sequentially, but rather, steps 1104 to 1116 may be executed in parallel for each pixel or a subset of pixels at the same time. Indeed, as will be discussed below, this exemplary method is well suited to vectorization and implementation on highly parallel processing architectures such as GPUs.

Figure 14A:
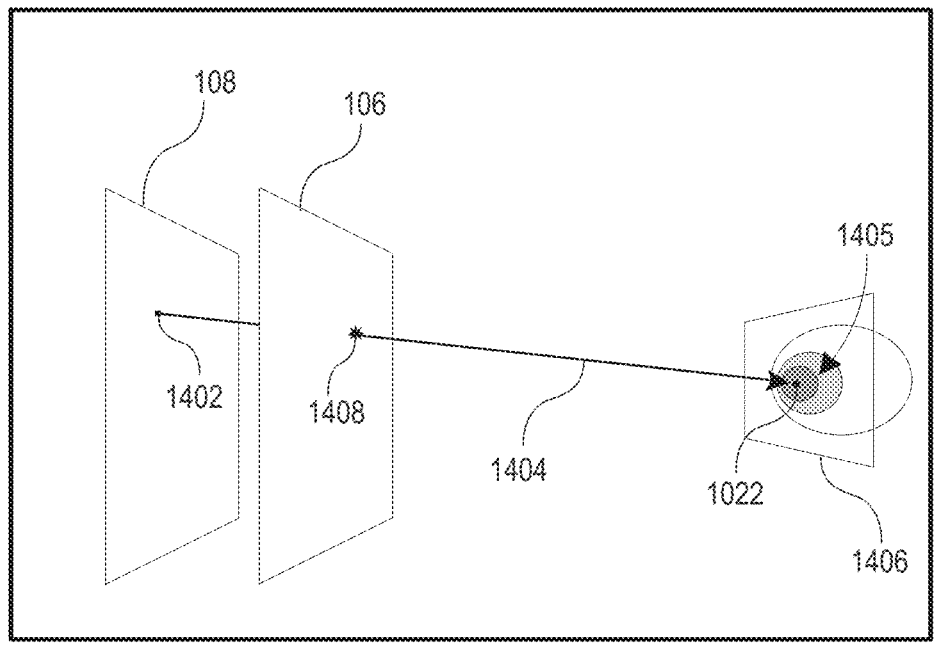
FIGS. 14A and 14B are schematic diagrams illustrating certain process steps of FIG. 11, in accordance with one embodiment.
Figure 14B:
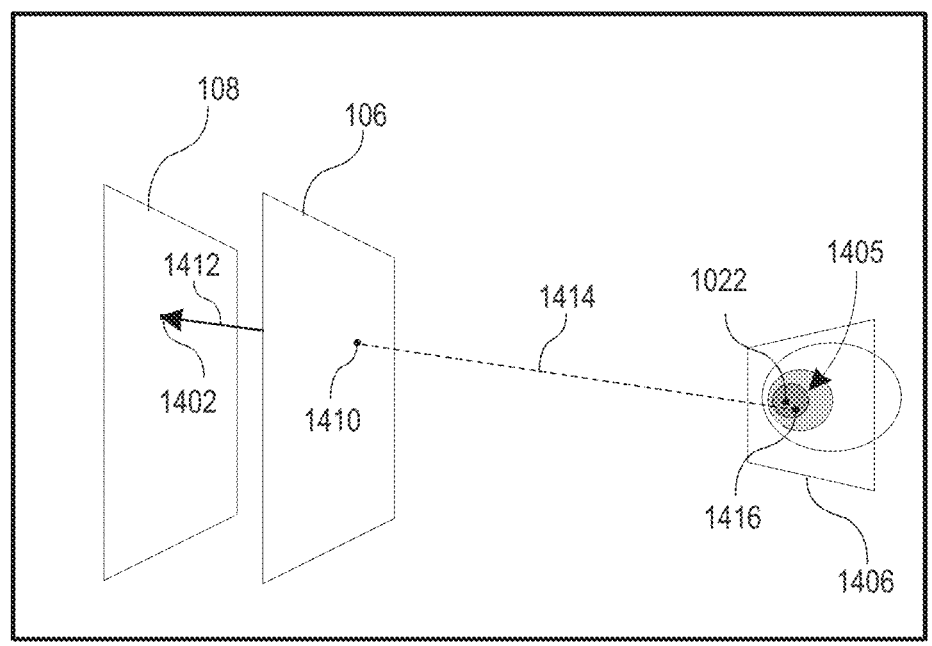

As illustrated in the schematic diagrams of FIG. 14A, in step 1104, for a given pixel 1402 in pixel display 108, a trial vector 1404 is first generated from the pixel's position to the pupil center position 1022 of the user's pupil 1405. As mentioned above, pupil center position 1022 may be acquired via eye/pupil tracker 110. In addition, a corresponding pupil plane 1406, which may be a flat 2D surface or plane in 3D space centered on pupil center position 1022, may be defined here as well. As shown in FIG. 14A, trial vector 1404, by construction, necessarily has to go through a corresponding optical unit of LFSL 106.

Once trial vector 1404 has been computed, in step 1106, a new Ray vector 1412 will be similarly generated from a center location/position 1410 of the corresponding optical unit comprising intersection point 1408 of LFSL 106 and pointing to pixel 1402. In this exemplary embodiment, step 1106 is detailed in the sub-steps 1206 to 1212 shown in FIG. 12.

Thus, in sub-step 1206, the location of intersection point 1408 of vector 1404 with the LFSL 106 is calculated as illustrated in FIG. 14A. In sub-step 1208, the coordinates of the center location 1410 of the optical element or unit of LFSL 106 closest to intersection point 1408 are computed. One way to efficiently compute this location is provided in related U.S. Pat. No. 10,394,322, the contents of which are incorporated herein by reference.

Once the position of the center 1410 of the optical element of LFSL 106 is known, in step 1210, as mentioned above, a normalized unit ray vector is generated from normalizing a ray vector 1412 originating from center position 1410 of LSFL 106 and extending to pixel 1402. This unit ray vector thus approximates the direction of the light field emanating from pixel 1402 through the center 1410 of this particular LFSL element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan.

The orientation of ray vector 1412 will be used to find the portion of input image 1020 on the adjusted image plane, and thus the associated color, represented by pixel 1402. But first, in step 1212, ray vector 1412 is projected backwards (dotted line 1414 on FIG. 14B) to intersect with pupil plane 1406 at location 1416.

Going back to FIG. 11, at step 1108, method 1100 verifies that intersection point 1416 with pupil plane 1406 of projected ray vector 1414 is still located within user pupil entrance 1405 (i.e. that the user can still "see" it). Thus, once intersection point 1416 shown in FIG. 14B of projected ray vector 1414 with the pupil plane 1406 is known, the distance between the pupil center 1022 and intersection point 1416 within pupil plane 1406 may be calculated to determine if the deviation is acceptable, for example by using predetermined pupil size 1424 and verifying how far the projected ray vector intersection 1416 is from pupil center 1022 within pupil plane 1406. If this deviation is deemed to be too large (i.e. light emanating from pixel 1402 channeled through optical element center 1410 is not perceived by pupil 1405), then in step 1110, method 1100 flags pixel 1402 as unnecessary and to simply be turned off or to render a black color.

In other embodiments, step 1108 may be modified so that instead of having a binary choice between the ray vector hitting the pupil or not, one or more smooth interpolation function (i.e. linear interpolation, Hermite interpolation or similar) may be used to quantify how far or how close intersection point 1416 is to pupil center 1022 within pupil plane 1406 and outputs a corresponding continuous value between 1 or 0. For example, the assigned value is equal to 1 substantially close to pupil center 1022 and gradually change to 0 as intersection point 1416 substantially approaches the pupil edges or beyond. In this case, the branch containing step 1110 may be ignored completely and step 1108 goes directly to step 1112. Then, at the end of step 1114, which will be discussed below, the pixel color value computed therein for pixel 1402 will be modified to be somewhere between the full color value identified therein or black, depending on the value of the interpolation function used at step 1108 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In the case where ray vector 1414 is within the pupil entrance (or if an interpolation function is used as discussed above), at step 1112, a corresponding image portion of input image 1020 located on the adjusted image plane and its corresponding color value are identified. As discussed above, two different but equivalent adjusted image planes may be used: a virtual image plane 1502 as shown schematically in FIG. 15 (i.e. positioned behind pixel display 108), or the retinal plane 1702 as shown in FIGS. 17A to 17D (i.e. behind user pupil 1405). Correspondingly, each variation of steps 1002 and 1112 are listed in the flow diagrams of FIGS. 13 and 16, respectively.

Figure 15:
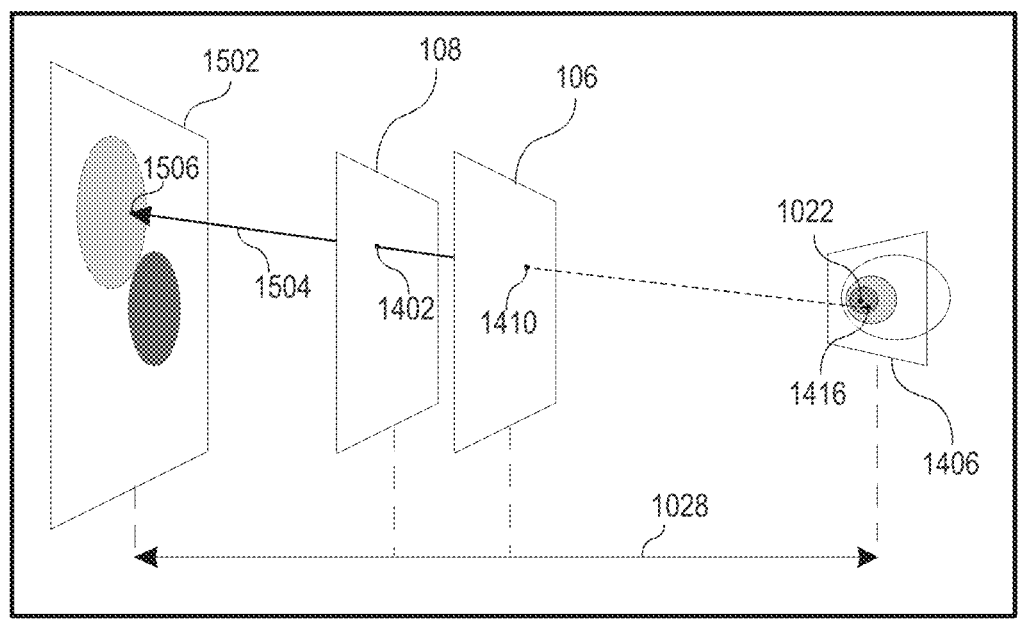
FIG. 15 is a schematic diagram illustrating the process steps of FIGS. 13 and 16, in accordance with one embodiment.

Thus, step 1102 is illustrated in FIG. 13, in accordance with one embodiment. In the case where virtual image planes are selected for ray-tracing in sub-step 1301, then as mentioned above ray-tracing is done using a virtual image plane 1502 as illustrated in FIG. 15. At sub-step 1302, the location or distance of virtual image plane 1502 from pupil plane 1406 may be computed as a function of spherical dioptric power 1026 (i.e. using the thin lens formula or other) and/or minimum reading distance 1028 (and/or related parameters). Then, at step 1304, input image 1020 is mapped onto virtual image plane 1502 so that its size of also scaled so to ensure that the perceived light field image correctly fills pixel display 108 when viewed by the distant user. An example is shown in FIG. 15 wherein virtual image plane 1502 is shown, as an example only, being located at a distance 1028 (in the z direction or depth) from pupil plane 1406, and the size of image 1020 is increased to avoid having the image as perceived by the user appear smaller than the display's size.

Figure 16:
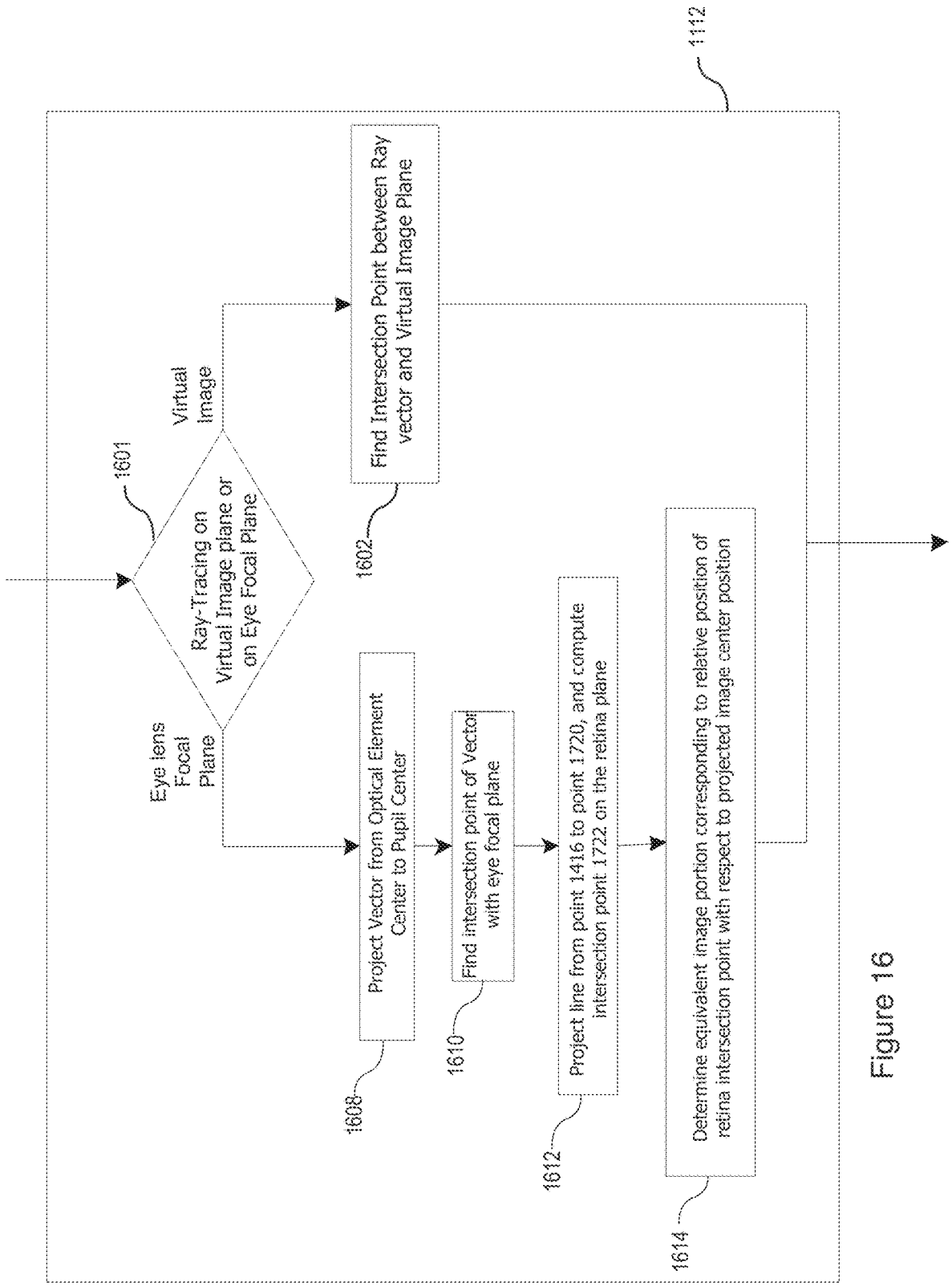
FIG. 16 is a process flow diagram illustrating certain process steps of FIG. 11, in accordance with one embodiment.

Continuing for the case of ray-tracing on virtual image plane 1502, the correct image portion is then identified in step 1112. So, as illustrated in FIG. 16, in this case sub-step 1601 leads to sub-step 1602. As schematically illustrated in FIG. 15, in sub-step 1602, ray vector 1412 is projected towards virtual image plane 1502 (shown as vector 1504 in FIG. 15) to find the position of the intersection point 1506. After this, the portion of image 1020 (and its associated colour channel) corresponding to intersection point 1506 on virtual image plane 1502 is identified.

As mentioned above, it may also be possible to use a retinal plane, herein defined as a 2D plane or surface substantially located at the location of the user's retina, as the adjusted image plane instead of virtual plane 1502.

Thus, in this case, illustrated schematically in FIGS. 17A to 17D, the adjusted image portion associated with a given pixel/subpixel is computed (mapped) on retinal plane 1702 instead of virtual image plane 1502 considered in the above example, again in order to provide the user with a designated image perception adjustment.

The skilled artisan will understand that a retinal plane may be defined in various ways. The exemplary embodiment described herein, the retinal plane 1702 is defined as a 2D plane located at a distance inside the eye equal to eye depth 1034 from the location of pupil center location 1022. It may also be taken to be parallel to pupil plane 1406, as illustrated in FIG. 17A to 17D, although it is not required to be so. It is meant to be an approximate location corresponding to the user's real retina.

Figure 17A:
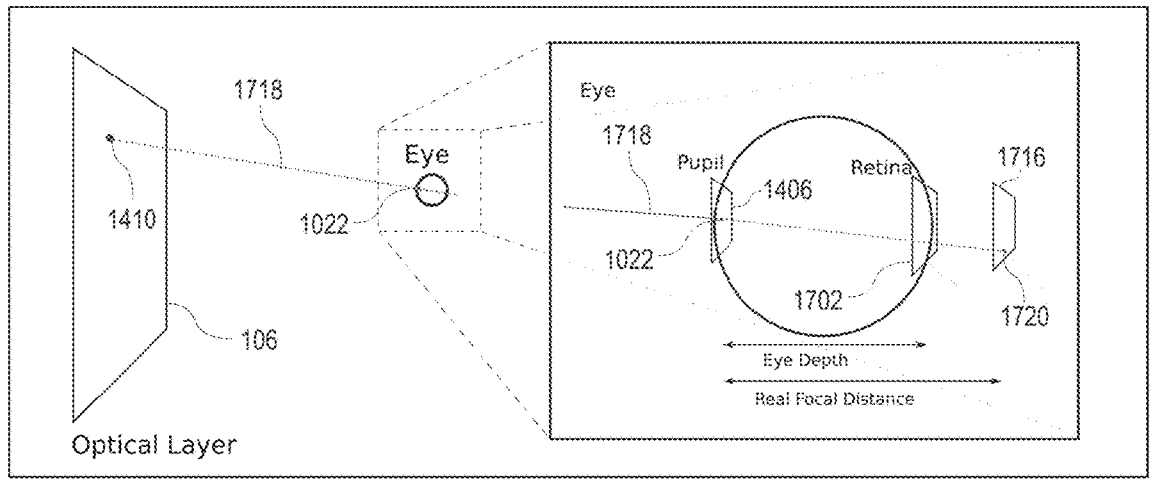
FIGS. 17A to 17D are schematic diagrams illustrating certain process steps of FIGS. 13 and 16, in accordance with one embodiment.
Figure 17B:
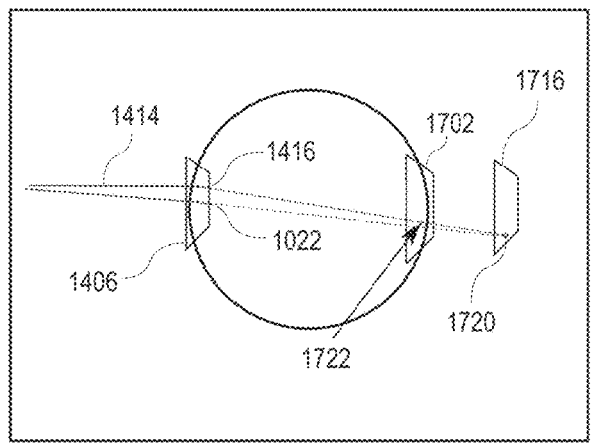
Figure 17C:
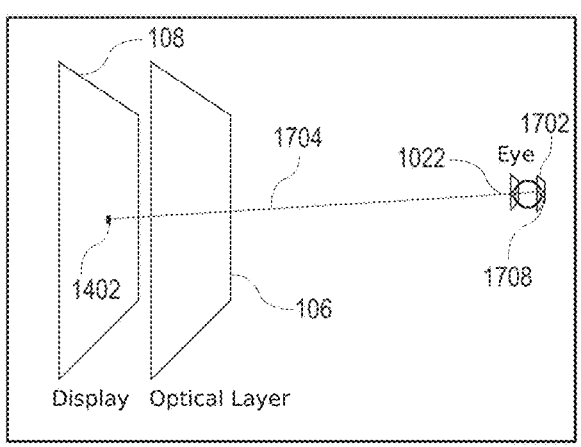
Figure 17D:
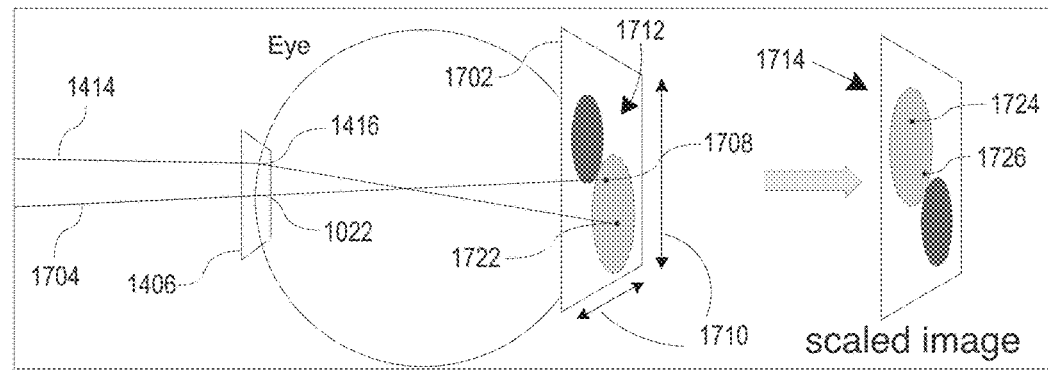

Thus, in the case where ray-tracing is done on retina image plane 1702, in step 1102 as shown in FIG. 13, sub-step 1301 leads to sub-step 1308, where a projected image center position on retinal plane 1702 is calculated. To do so, as illustrated in FIG. 17C, a vector 1704 is drawn originating from the center 1706 of pixel display 108 and passing through pupil center 1022. Vector 1704 is further projected beyond pupil plane 1405 onto retinal plane 1702, and the associated intersection point 1708 gives the location of the corresponding image center on retinal plane 1702. Once image center 1708 is known, in sub-step 1310 one can scale image 1020 to the x/y retina image size 1710, as illustrated schematically in FIG. 17D. In some embodiments, the required scaling may be computed by calculating the magnification of an individual pixel on retinal plane 1702, for example, which may be approximately equal to the x or y dimension of an individual pixel multiplied by the eye depth 1034 and divided by the absolute value of the distance to the eye (i.e. thus giving the magnification of the image portion created a pixel once focused by the eye lens on retinal plane 1702). An exemplary scaled inverted image 1712 on retinal plane 1702 is shown in FIG. 17D. Similarly, for comparison purposes, the input image 1020 may also normalized by the image x/y dimensions to produce a corresponding normalized input image 1714 having a width and height between −0.5 to 0.5 units, which may be compared to inverted scaled image 1712 which may also be similarly normalized.

In addition to sub-steps 1308 and 1310, sub-step 1312 is done independently to determine a location of a focal plane as produced by the user's eye for a given input value of spherical dioptric power 1026 (or minimum reading distance 1028). Thus, eye focal plane 1716 shown in FIGS. 17A and 17B is defined as the location where any light ray originating from optical unit center location 1410 would be focused by the user's eye. For a user with perfect vision, focal plane 1716 would be located at the same location as retinal plane 1702, but in the example shown in FIGS. 17A and 17B, as an example only, focal plane 1716 is located behind retinal plane 1702, which would be expected for a user with some form of farsightedness. The position of focal plane 1716 may be derived from the user's minimum reading distance 1028 or spherical dioptric power 1026, for example, by deriving therefrom the corresponding focal length of the user's eye. Other manually input or computationally or dynamically adjustable means may also or alternatively be considered to quantify this parameter.

Going back to FIG. 16, step 1112 in the case of ray-tracing on retinal plane 1702 has sub-step 1601 leading to to sub-step 1608, illustrated schematically in FIG. 17A, where a vector 1718 is drawn from optical unit center 1410 to pupil center 1022. Then, in sub-step 1610, vector 1718 is projected further behind pupil plane 1406 onto eye focal plane 1716 where intersection point 1720 is identified.

The skilled artisan will note that any light ray originating from optical unit center 1410, no matter its orientation, will also be focused onto intersection point 1720, to a first approximation. Therefore, in some embodiments, the location 1722 on retinal plane 1702 onto which light entering the pupil at intersection point 1416 will converge may be approximated, at sub-step 1612, by drawing a straight line between intersection point 1416 where projected ray vector 1414 hits pupil plane 1406 and focal point 1720 on focal plane 1716, as illustrated in FIG. 17B. The intersection of this line with retinal plane 1702 (retina image point 1722) is thus the location on the user's retina corresponding to the image portion that will be reproduced by corresponding pixel 1402 as perceived by the user. Therefore, at sub-step 1614, by comparing the relative position of retinal point 1722 with the overall position of the projected image on the retinal plane 1702, the relevant adjusted image portion associated with pixel 1402 may be computed.

For example, the image portion position 1724 relative to retina image center position 1726 in the scaled coordinates (scaled input image 1714) corresponds to the inverse (because the image on the retina is inverted) scaled coordinates of retina image point 1722 with respect to retina image center 1708, as shown in FIG. 17D. Thus, the associated color with image portion position 1724 may be therefrom extracted and associated with pixel 1402.

Once step 1112 is finished, in step 1114, pixel 1409 is flagged as having the color value associated with the portion of image corresponding to intersection point 1506 in the case of ray-tracing on virtual image plane 1502 (as shown in FIG. 15) or in the case of ray-tracing on retinal plane 1702, to the image portion corresponding to intersection 1725 as shown in FIG. 17D.

At step 1116, a check is made to see if every pixel in pixel display 108 has been ray-traced. If not then method 1100 chooses another pixel 1402 and goes back to step 1104; if so, then the output color of all pixels has been determined and these are finally rendered in step 1118 by pixel display 108 to be viewed by the user, therefore presenting a light field corrected image. In the case of a single static image, the method may stop here. In yet other embodiments, pixels found to illuminate a designated area around the pupil may still be rendered, for example, to produce a buffer zone to accommodate small movements in pupil location, for example, or again, to address potential inaccuracies or misalignments.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process steps of FIGS. 16A and 16B can accommodate the formation of a virtual image effectively set at infinity without invoking such computational challenges. Likewise, while first order aberrations are illustratively described with reference to FIG. 11, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1104 to 1116 of FIG. 11) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

In some embodiments, additional efficiencies may be leveraged on the GPU by storing the image data, for example image 1020, in the GPU's texture memory. Texture memory is cached on chip and in some situations is operable to provide higher effective bandwidth by reducing memory requests to off-chip DRAM. Specifically, texture caches are designed for graphics applications where memory access patterns exhibit a great deal of spatial locality, which is the case of the steps 1104 to 1116 of FIG. 11. For example, in method 1100, image 1020 may be stored inside the texture memory of the GPU, which then greatly improves the retrieval speed during step 1112 (including either one of the ray-tracing variants presented in FIGS. 13 and 16) where the color channel associated with the portion of input image 1020 is determined.

Non-Parallel Planes

While method 1100 presented above (and its associated variations) was discussed and illustrated as having each plane (i.e. virtual image plane 1502, pixel display 108, LSFL 106, pupil plane 1406, retinal plane 1702 or eye lens focal plane 1716) as being parallel with each other, this was only done as an example for clarity and to better describe the methodology associated therewith. Indeed, method 1100 as discussed may equally be applied to account for changes in the relative orientation between any one of those planes.

Figure 18:
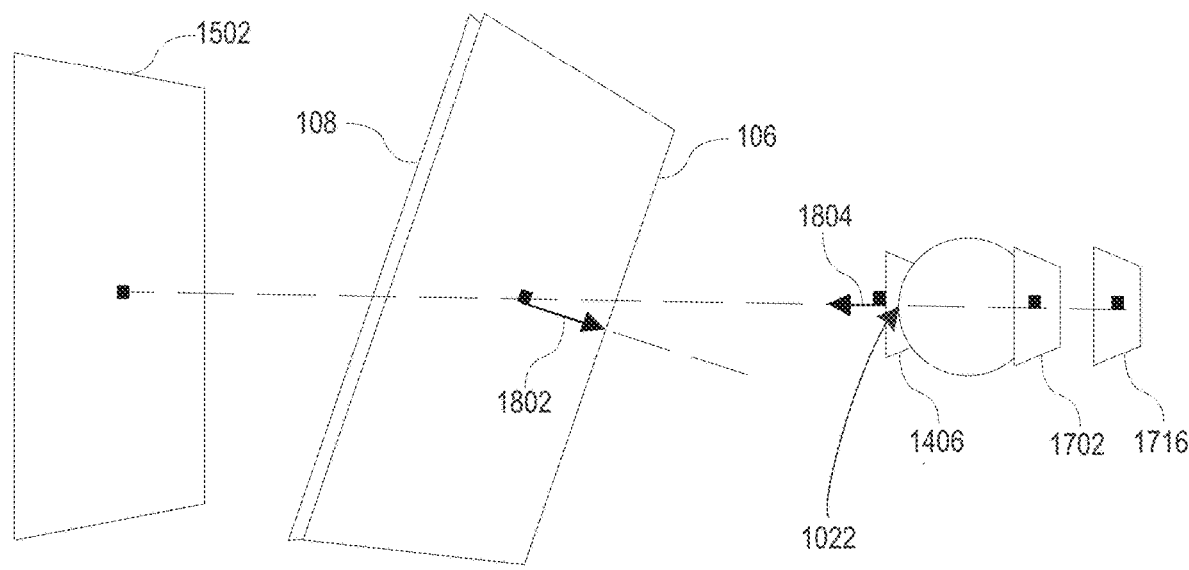
FIGS. 18 and 19 are schematic diagrams illustrating ray-tracing in the context of non-parallel planes, in accordance with one embodiment.
Figure 19:
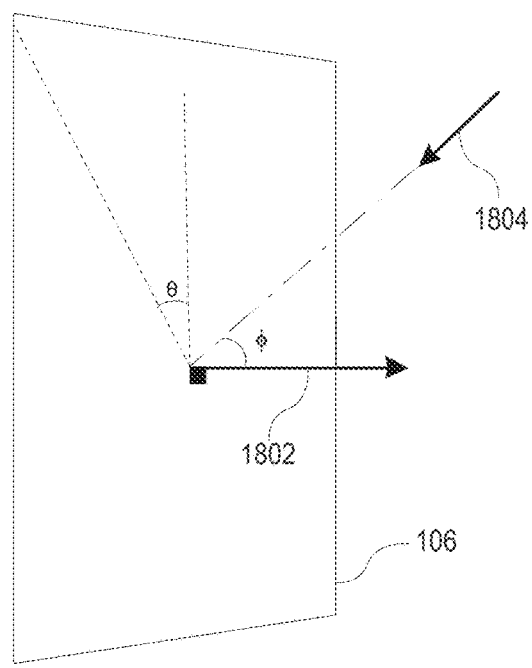

For example, and with reference to FIGS. 18 and 19, and in accordance with one exemplary embodiment, ray-tracing with non-parallel planes will now be discussed. In some embodiments, and as illustrated in FIG. 18, cases may be considered wherein the user is viewing the light field display at an angle. In this specific example, the ray-tracing method can therefore account for a change in orientation of the pupil plane 1406 with respect to the pixel display 108 and optical layer 106. In this example, other planes such as virtual image plane 1502, and retinal plane 1702 and focal plane 1716 may be taken to be parallel to pupil plane 1406. The relative difference in orientation between the two sets of planes is illustrated by using vector 1802 which is the normal vector to the plane of corresponding optical layer 106, and vector 1804 which is the normal vector to pupil plane 1406. The relative orientation between the two normal vectors is illustrated in FIG. 19, using polar and azimuthal angles.

The general orientation of pupil plane 1406 may be parametrized, for example, by using the 3D location of pupil center 1022 and a corresponding normal vector 1804. Normal vector 1804 may be taken to be, in some embodiments, equal to the gaze direction as measured by a gaze tracking system or similar, as will be discussed below.

Once the relative position and orientation of pupil plane 1406 is determined, the relative position/orientation of all remaining planes (parallel or non-parallel) may be determined and parametrized accordingly. Planes that are parallel share the same normal vector. From there, the method 1100 and its variants described above may be applied by finding the intersection point between an arbitrary vector and an arbitrarily oriented plane, as is done for example at steps 1206, 1212, 1602, 1610, 1612 for example.

In the illustrated example of FIG. 18, the position of virtual image plane 1502 may be computed using spherical dioptric power 1026 (and/or minimum reading distance 1028 and/or related parameters) but from the position of pupil plane 1406 and along the direction vector 1804.

To extract normal vector 1804 of pupil plane 1406, the eye tracking methods and systems described above may be used or modified to further provide a measure of the eye's gaze direction (e.g. gaze tracking). As discussed above, there are many known eye tracking methods in the art, some of which may also be used for gaze-tracking. For example, this includes Near-IR glint reflection methods and systems or methods purely based on machine vision methods. Hence, in some embodiments, pupil plane 1406 may be re-parametrized using an updated 3D location of pupil center 1022 and an updated normal vector 1804 at each eye tracking cycle. In other embodiments, a hybrid gaze tracking/pupil tracking system or method may be used wherein gaze direction (e.g. normal vector 1804) is provided at a different interval than pupil center location 1022. For example, in some embodiments, for one or more cycles, only the 3D pupil center location 1022 may be measured and an old gaze direction vector may be re-used or manually updated. In some embodiments, an eye model or similar may be constructed to map a change in measured pupil center location 1022 to a change in the gaze direction vector without relying on the full capabilities of the gaze tracking system or method. Such a map may be based on one or more previous gaze tracking measurements. In any case, by measuring/determining the 3D pupil center location 1022 and normal vector 1804, the pupil plane may be parametrized accordingly.

Note that in FIG. 18, pixel display 108 and optical layer 106 are shown as being parallel for simplicity, but other embodiments may envision optical layer 106 to be non-parallel to display 108 as well. This doesn't change the general scope of the present discussion, as long as the relative angle between them is known. For example, such an angle may be pre-determined during manufacturing or measured in real-time using one or more sensors (for example in the case where optical layer 106 may be mobile). Similarly, other planes like for example retinal plane 1702 may also be made to be non-parallel to the pupil plane, depending on the user's eye geometry.

Concurrent Multi-Depth Rendering

Figure 20A:
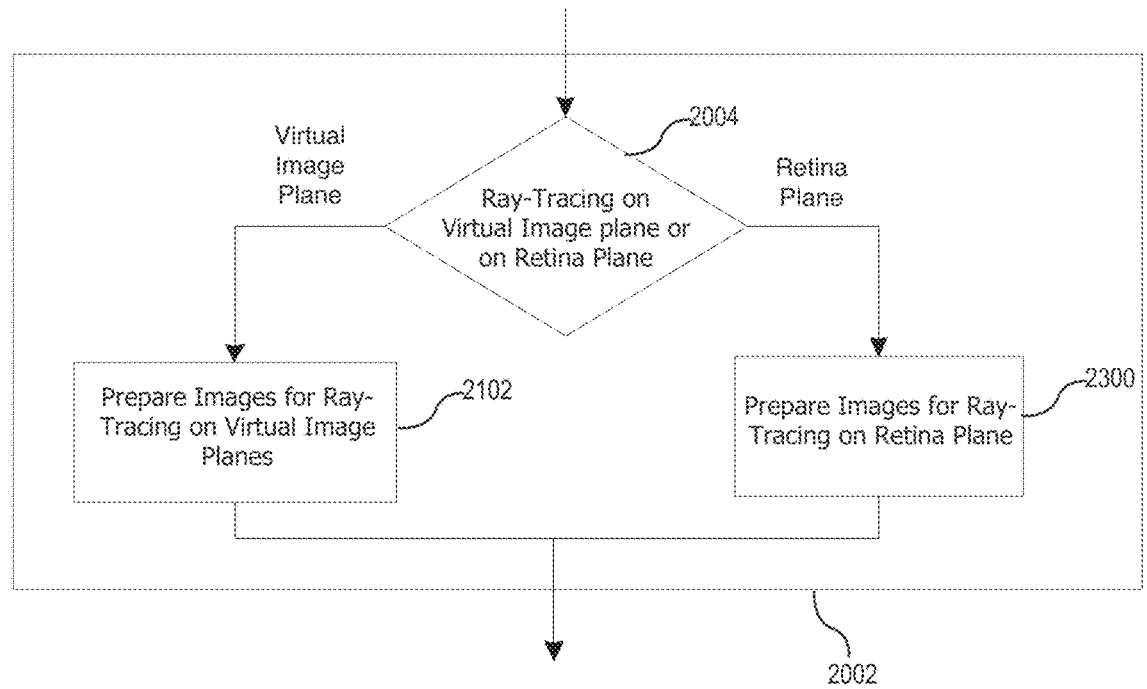
FIGS. 20A and 20B are process flow diagrams of certain process steps of FIG. 11 for rendering a light field originating from multiple distinct virtual image planes, in accordance with one embodiment.
Figure 20B:
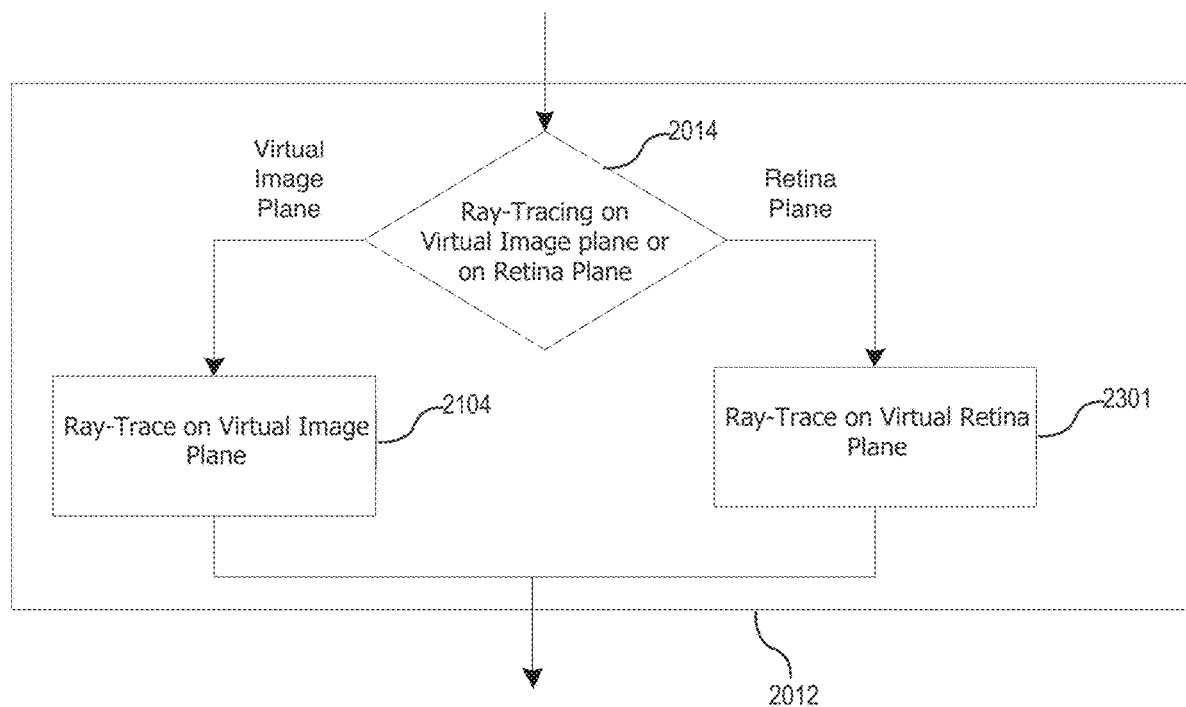

With reference to FIGS. 20A to 22D and in accordance with one embodiment, a modified embodiment of method 1100 operable to render multiple images or image portions on multiple adjusted distinct image planes simultaneously via an array of light field shaping elements, or light field shaping layer (LFSL) thereof, will now be discussed. Thus, step 2002 shown in FIG. 20A is meant to replace step 1102 in method 1100, while step 2012 of FIG. 20B replaces step 1112. This is because the previously above-described steps 1102 and 1112 were directed to correcting a single image by directly or indirectly modifying the location of the virtual image plane and/or eye focal plane. In contrast, the below-described embodiments of steps 2002 and 2012 are directed to a light field display which is generally operable to display multiple image planes at different locations/depths/aberrations simultaneously. Thus, in step 2002, at sub-step 2004, the method continues to sub-step 2102 (illustrated in FIG. 21A) if ray-tracing is done using the virtual image plane or if ray-tracing is done using the retinal plane then sub-step 2300 is used (illustrated in FIG. 23A). Similarly, as shown in FIG. 20B, from sub-step 2014, the method proceeds to sub-step 2104 in the case of ray-tracing to virtual image plane (illustrated in FIG. 21B) or to sub-step 2301 (illustrated in FIG. 23B if ray-tracing is done using the retinal plane).

Unlike known stereoscopic effects, the methods as herein described may be implemented to generate varying depth perceptions within a same eye, that is, allowing for the monoscopic viewing of an input to exhibit multiple distinct image perception adjustments (i.e. multiple juxtaposed and/or overlapping depths, enhancements or like optical adjustments, compensations, etc.). For example, in some embodiments, distinct image planes may be juxtaposed such that different sides or quadrants of an image, for example, may be perceived at different depths. In such embodiments, a different effective vision correction parameter (e.g. diopter), or depth, may be applied, to each portion or quadrant. While this approach may result in some distortions or artefacts at the edges of the areas or quadrants, depending on the image data to be rendered along these edges, such artefacts may be negligible if at all perceivable. In other embodiments, however, different image portions may be at least partially superimposed such that portions at different depths, when viewed from particular perspectives, may indeed appear to overlap. This enables a user to focus on each plane individually, thus creating a 2.5D effect. Thus, a portion of an image may mask or obscure a portion of another image located behind it depending on the location of the user's pupil (e.g. on an image plane perceived to be located at an increased distance from the display than the one of the first image portion). Other effects may include parallax motion between each image plane when the user moves.

Figure 23A:
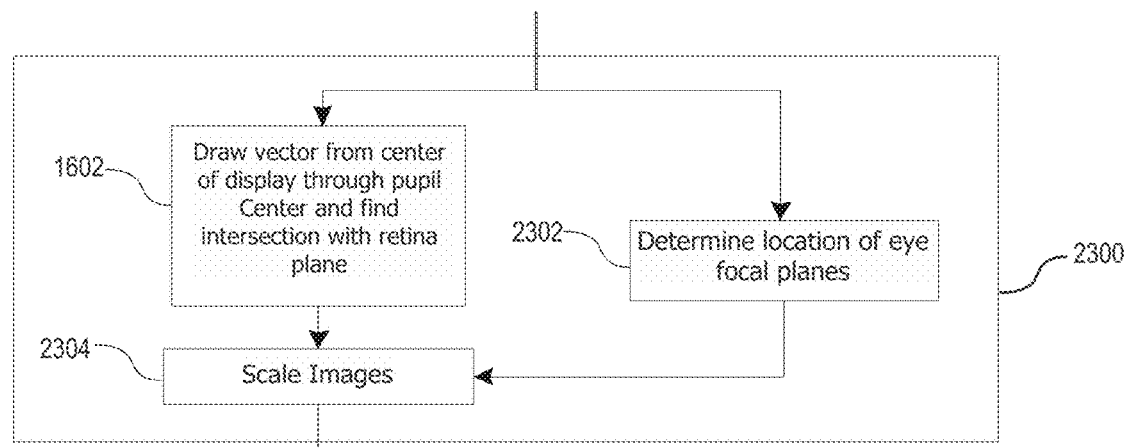
FIGS. 23A and 23B are process flow diagrams of certain process steps of FIG. 11 for rendering a light field originating from multiple distinct focal planes, in accordance with one embodiment.
Figure 23B:
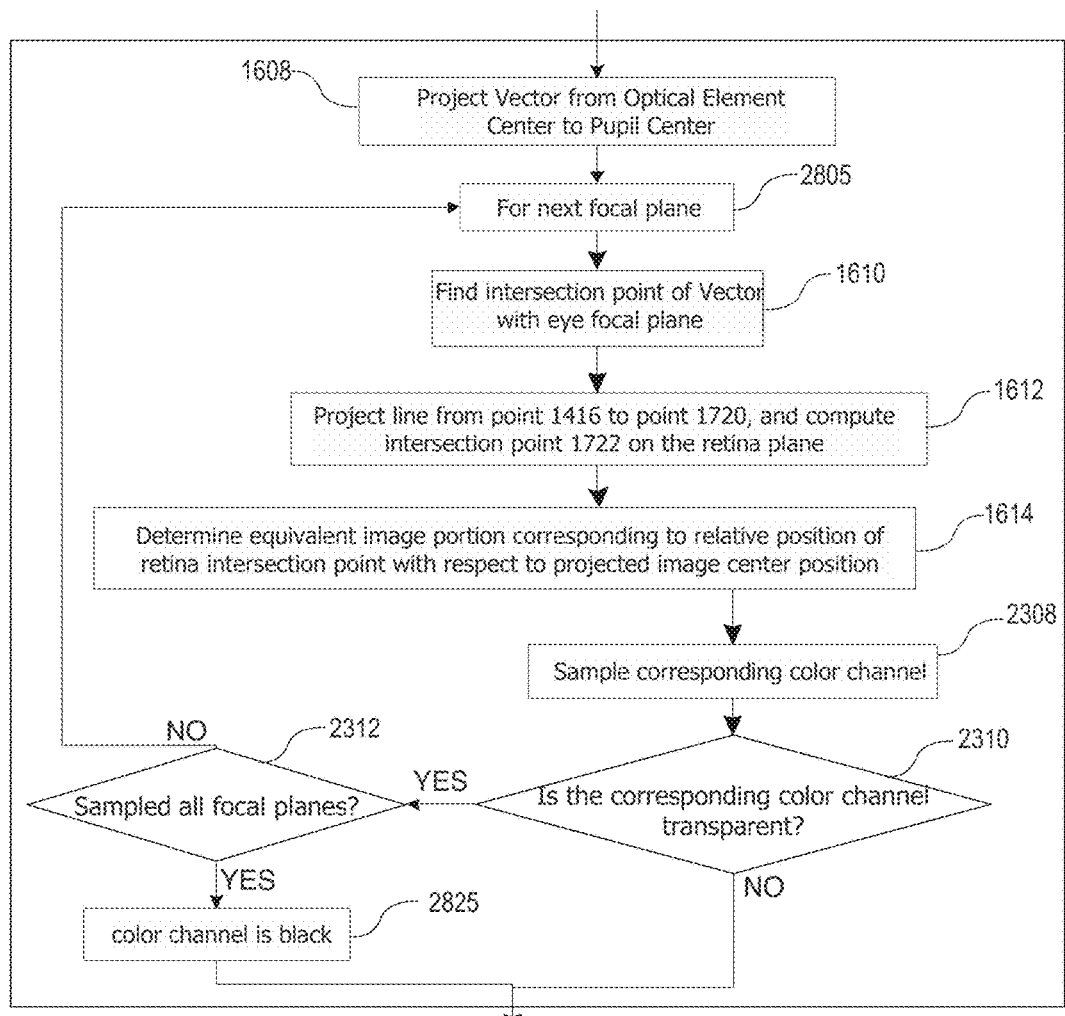

As mentioned above, steps 2102 and 2104 of FIGS. 21A and 21B are directed towards ray-tracing on one or more virtual image plane only, while steps 2300 and 2301 of FIGS. 23A and 23B are directed towards ray-tracing on the retinal plane.

For example, to account for multiple distinct image planes, input image 1020 of input variables 1004 may also include, in addition to pixel data, variable dioptric powers or perceptive "depth" information or parameters. Thus, any image or image portion may have a respective depth indicator. Thus, at sub-step 2106, a set of multiple virtual image planes may be defined, at sub-step 2108, which includes deriving their respective (virtual) location, similarly to sub-step 1302. On these planes, images or image portions may be present. Areas around these images may be defined as transparent or see-through, meaning that a user would be able to view through that virtual image plane and see, for example, images or image portions located behind it. At sub-step 2108, any image or image portion on each of these virtual image planes may be optionally scaled to fit the display, similarly as described for sub-step 1304 for a single image plane.

In the previous example shown in FIG. 15, a single virtual image plane 1502, showing an exemplary input image 1020 comprising two circles, was used. In contrast, FIGS. 22A to 22D show an example wherein each circle is located on its own virtual image plane (e.g. original virtual plane 1502 with new virtual image plane 2202). The skilled technician will understand that two planes are shown here only as an example and that the method steps described herein apply equally well to any number of virtual planes. The only effect of having more planes is a larger computational load.

Going back to 21B, in step 2104, an iteration is done over the set of virtual image planes to compute which image portion from which virtual image plane is seen by the user. Thus, at sub-step 2110 a virtual image plane is selected, starting from the plane located closest to the user. Then step 1602 proceeds as described previously for that selected virtual plane. At sub-step 2112 the corresponding color channel of the intersection point identified at step 1602 is sampled. Then at sub-step 2114, a check is made to see if the color channel is transparent. If this is not the case, then the sampled color channel is sent to step 1114 of FIG. 11, which was already described and where the color channel is rendered by the pixel/subpixel. An example of this is illustrated in FIGS. 22A and 22B, wherein a user is located so that a ray vector 2204 computed passing through optical element center location 1410 and pixel/subpixel 1402 intersects virtual image plane 1502 at location 1506. Since in this example this location is non-transparent, this is the color channel that will be assigned to the pixel/subpixel. However, as this example shows, this masks or hides parts of the image located on virtual image plane 2202. Thus, an example of the image perceived by the user is shown in FIG. 22B.

Figure 21A:
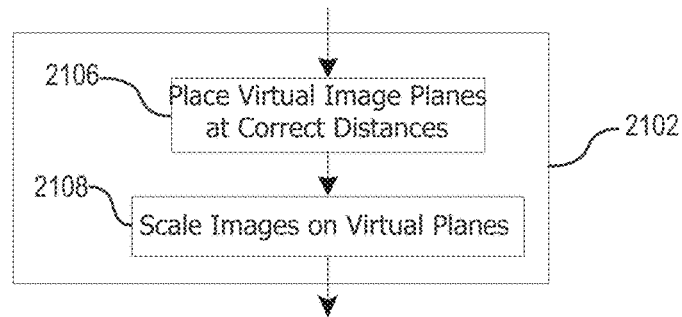
FIGS. 21A and 21B are process flow diagrams of certain process steps of FIGS. 20A and 20B for rendering a light field originating from multiple distinct virtual image planes, in accordance with one embodiment.
Figure 21B:
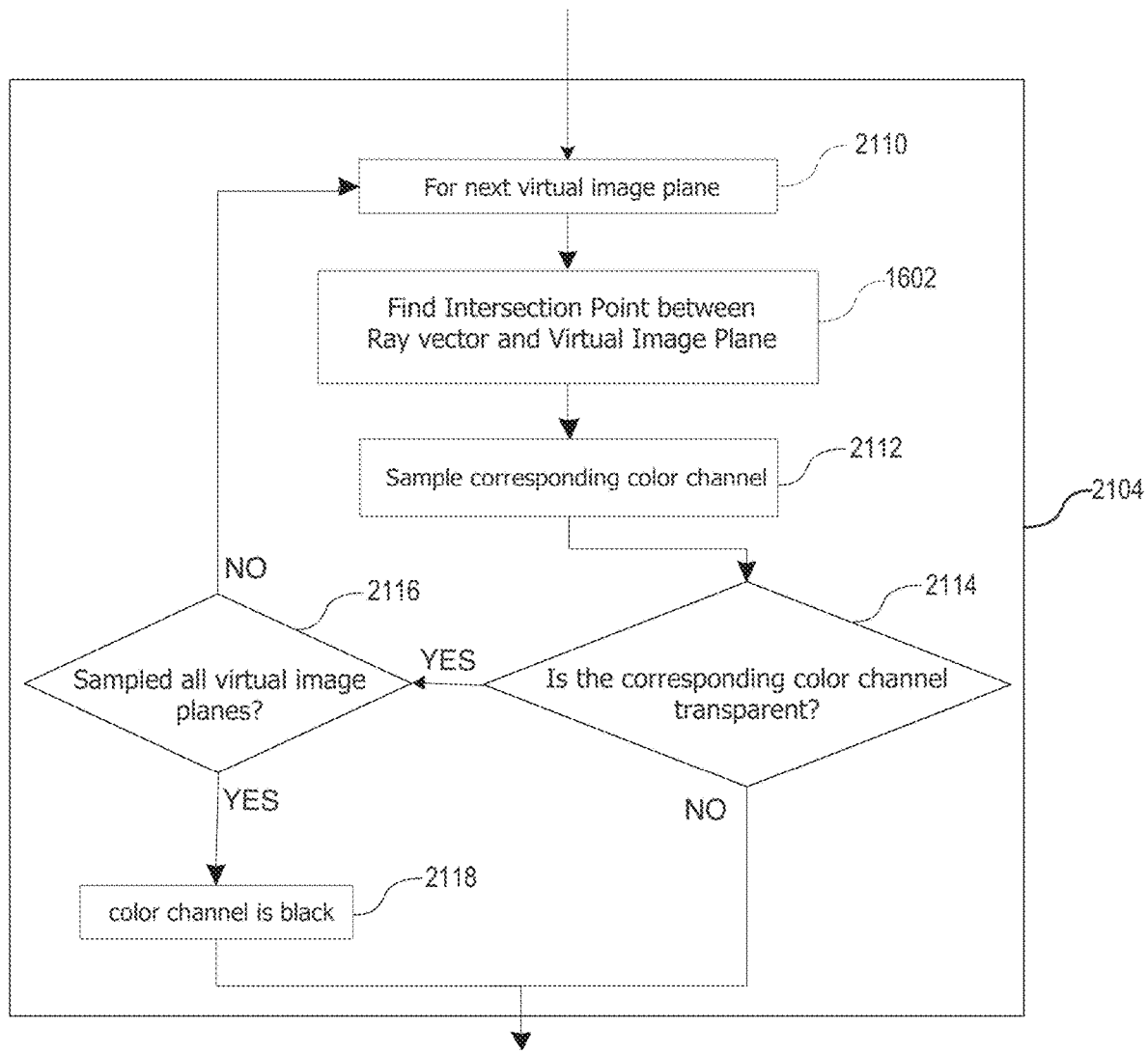

Going back to FIG. 21B, at sub-step 2114 if the color channel is transparent, then another check is made at sub-step 2116 to see if all virtual image planes have been iterated upon. If this is the case, then that means that no image or image portion is seen by the user and at sub-step 2118, for example, the color channel is set to black (or any other background colour), before proceeding to step 1114 of FIG. 11. If however at least one more virtual image plane is present, then the method goes back to step 2110 and selects that next virtual image plane and repeats sub-steps 1602, 2112 and 2114. An example of this is illustrated in FIG. 22C, wherein a user is located so that a distinct ray vector 2204 computed passing through optical element center 2206 of LFSL 106 and pixel/subpixel 2208 of pixel display 108 first intersects at location 2210 of virtual image plane 1502. Since, in this example, this location is defined to be transparent (i.e. not on the circle), the method checks for additional virtual image planes (here plane 2202) and extends vector 2204 so as to compute intersection point 2212, which is now non-transparent (i.e. on the circle), and thus the corresponding color channel is selected. An example of the image perceived by the user is shown in FIG. 22D.

Similarly, steps 2300 and 2301 of FIGS. 23A and 23B substantially mirrors steps 2102 and 2104, respectively, described in FIGS. 21A and 21B, but are herein applied to be used with two or more eye focal planes (e.g. for ray-tracing the image on retinal image plane 1702). Thus, we see that the method iterates, after sub-step 1608, over all designated image planes, each corresponding to a different eye focal plane, starting from the plane corresponding to an image located closest to the user. Thus, a new eye focal plane is selected at sub-step 2306, which is used for sub-steps 1610 to 1614 already described above. Once the corresponding image portion is determined at sub-step 1614, at sub-step 2308, the corresponding pixel/subpixel color channel is sampled. Then at sub-step 2310, if the color channel is non-transparent, then the method continues to step 1114 of FIG. 11, wherein the pixel/subpixel is assigned that color channel. However, if the image portion is transparent, then the method iterates to the eye focal plane corresponding to the next designated image plane. Before this is done, the method checks at sub-step 2312 if all the eye focal planes have been iterated upon. If this is the case, then no image portion will be selected and at sub-step 2314 the color channel is set to black, for example, before exiting to step 1114. If other eye focal planes are still available, then the method goes back to sub-step 2306 to select the next eye focal plane and the method iterates once more.

Figure 24A:
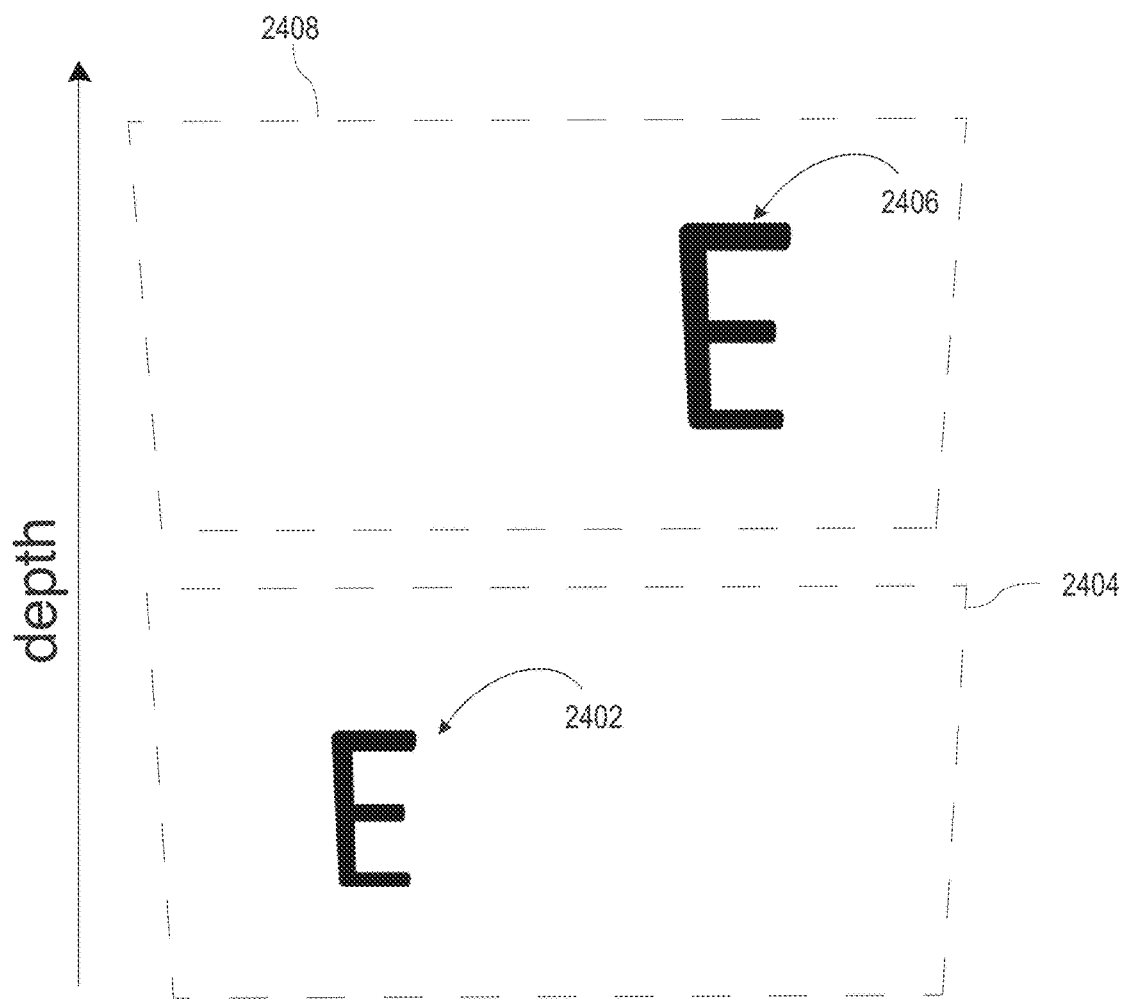
FIGS. 24A and 24B are schematic diagrams illustrating an example of a subjective visual acuity test using the ray-tracing rendering process of FIG. 23A or FIG. 23B, in accordance with one embodiment.
Figure 24B:
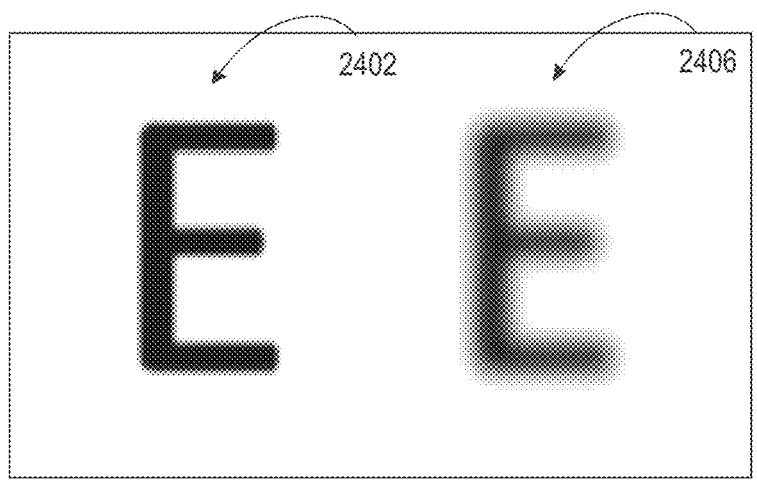

In some embodiments, as mentioned above, steps 2102, 2104 or 2300 and 2301 for multiple designated image planes of FIGS. 21A-B (on virtual planes) or FIGS. 23A-B (retinal plane) may be used to implement a phoropter/refractor device to do subjective visual acuity evaluations. For example, as illustrated in FIGS. 24A and 24B, and similarly to FIG. 9, different optotypes (e.g. letters, symbols, etc.) may be displayed simultaneously but at different perceived depths, to simulate the effect of adding a refractive optical component (e.g. change in focus/optical power). In FIG. 24A, two images of the same optotype (e.g. letter E) are displayed, each on their own designated image plane (e.g. here illustrated as virtual image planes as an example only). In this example, image 2402 is located on designated image plane 2404 while image 2406 is located on designated image plane 2408, which is located further away. Optionally, as illustrated herein, the size of the image may be increased with increased depth so that all images displayed are perceived to be of a similar relative size by the user. In FIG. 24B, we see an example of the perception of both images as perceived by a user with reduced visual acuity (e.g. myopia), for example, wherein the image closest to the user is seen to be clearer. Thus, a user could be presented with multiple images (e.g. 2 side-by-side, 4, 6 or 9 in a square array, etc.) and indicate which image is clearer and/or most comfortable to view. An eye prescription may then be derived from this information.

While the above presents a multi-depth ray-tracing approach that may be applied to each image frame, effectively, whereby image portions to be respectively perceived at respective image depths are concurrently processed for a given rendering, alternative approaches may also be considered to achieve a similar effect.

For example, in some embodiments, interlacing techniques or methods may be used to generate two or more light field images to the patient simultaneously. In some embodiments, concurrent light field vision-corrected images may be generated at multiple values of eye focus dioptric powers using refractor 102. This method is based on dividing the spatial or temporal (or both) domains of the display separately or concurrently so as to enable a user to be able to focus on different optical planes at the same time simultaneously.

Figure 32A:
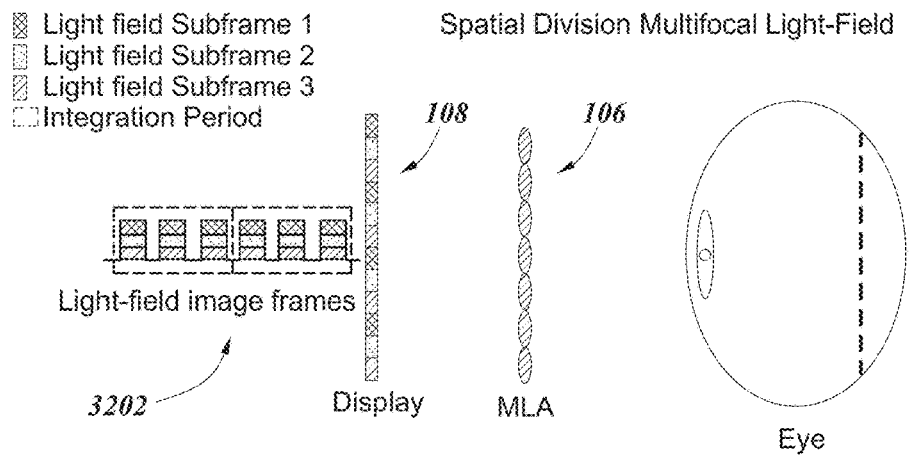
FIGS. 32A to 32C are schematic diagrams illustrating the rendering of multiple light field images simultaneously using spatial interlacing (32A), temporal interlacing (32B) or a combination thereof (32C)

In some embodiments, schematically illustrated in FIG. 32A, spatial interlacing may be used. For example, the pixels of pixel display 108 may be divided or grouped in a periodic manner wherein each periodic division of the display may be used to generate a light-field image at a corresponding (different) focal plane. This is shown in FIG. 32A where composite light field image frame 3202, comprising light field image subframes 1, 2 and 3, are fed simultaneously to different pixels of pixel display 108, so as to produce different light field image depths via LFSL 106. This provides the ability to simultaneously project corrected images for people with different visual deficiency levels. This allows to simultaneously project different images or optotypes corresponding to different image plane locations.

Figure 32B:
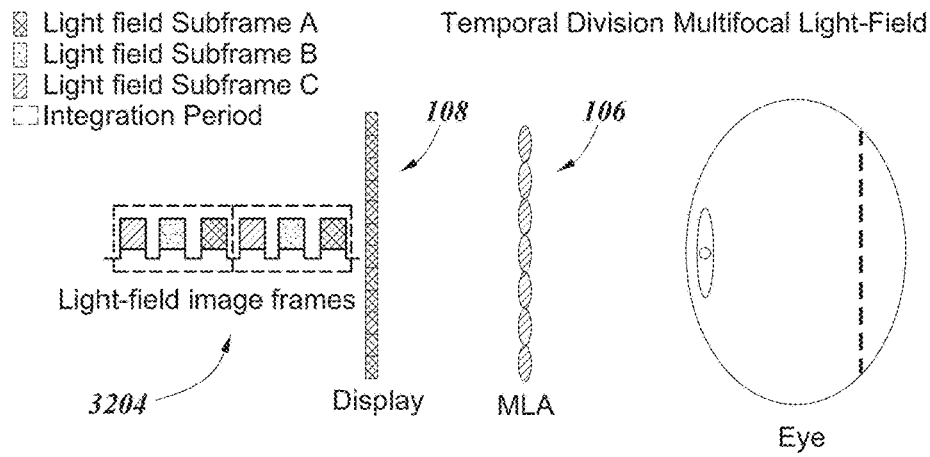

In some embodiments, a temporal interlacing implementation may be used instead. For example, and as schematically illustrated in FIG. 32B, pixel display 108 may be configured to have a refresh rate which is faster than the human flicker fusion threshold so that subsequent image frames may be used to generate distinct light field images that will be perceived as being generated simultaneously by the human brain. This is shown in FIG. 32B where the light field image frames 3204 are shown comprising three different light field image frames A, B and C, which are shown subsequently within the integration period. Thus, in contrast with spatial interlacing where for a given image only some portion of the pixels may be used, herein the full display may be used to calculate and project light field images at different focal planes or correction levels simultaneously. The number of the desired concurrent light-field images may be selected based on the refresh rate of the high-speed display and the flicker fusion threshold of the subject.

Figure 32C:
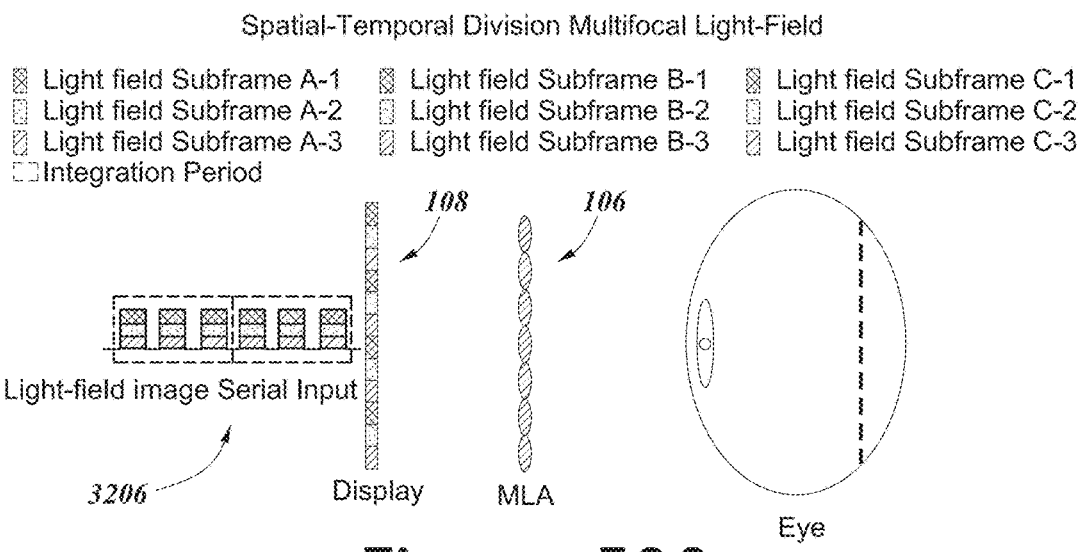

In some embodiments, schematically illustrated in FIG. 32C, the two methods above, spatial and temporal interlacing, may be combined to increase the number of the projected light-field images at different planes. Thus, in FIG. 32C, light field image serial input or frame 3206 comprises a combination of subframes A-1 to A3, B-1 to B-3, and C-1 to C3, respectively.

Design Optimization

Figure 25A:
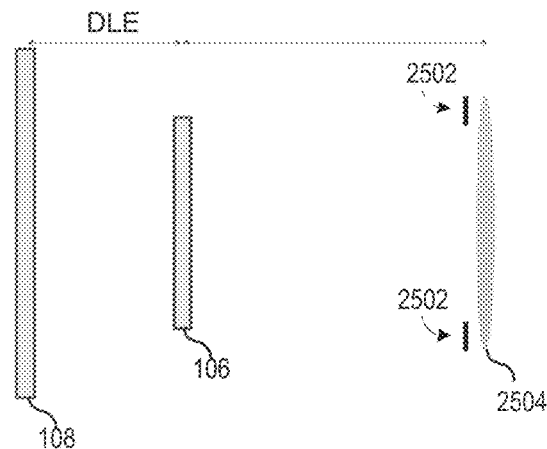
FIGS. 25A, 25B, 25C and 25D are, respectively, a schematic diagram of an exemplary refractor device, a schematic diagram illustrating certain variables for a binocular implementation of the refractor device, a photograph of a light field image produced by the exemplary refractor device, and a plot illustrating the change in resolution of a light field image as a function of the cylindrical dioptric power correction, in accordance with one embodiment.

As detailed above, and reprised here with reference to FIG. 25A, a light-field vision-based testing device as contemplated herein will generally include a light field display (e.g. pixel display 108 and LFSL 106) operated to controllably produce an output image to be perceived by a user in accordance with a desired viewing perspective, which may include various variable simulated optical depth, distortion, aberration or correction values and effects. Generally, a quality of the perceptively adjusted effect will rely, in part, on a quality and alignment of the view zone/produced by the device at its output in relation to the user's eye, in particular, when perceived through their pupil and projected on their retina.

As will be described in further detail, below, a device as described herein operating in accordance with sub-optimal ray tracing, optical, geometrical, alignment and/or configurational parameters, may result in a sub-optimal user experience, for example in producing optical artefacts such as view zone interference, overlap, cross-talk, etc. For example, where a view zone projection output geometry does not adequately align or correspond with the viewer's eye geometry, positioning, alignment and/or response, and/or where intervening optics inadvertently interfere with or adversely impact view zone boundaries, alignment, quality and/or accuracy, a degraded user experience may impact test results, accuracy or user comfort, for example. Various image perception parameters may also be adversely impacted such as, for example, image resolution, field of view (FoV), brightness, scaling, etc.

Figure 29:
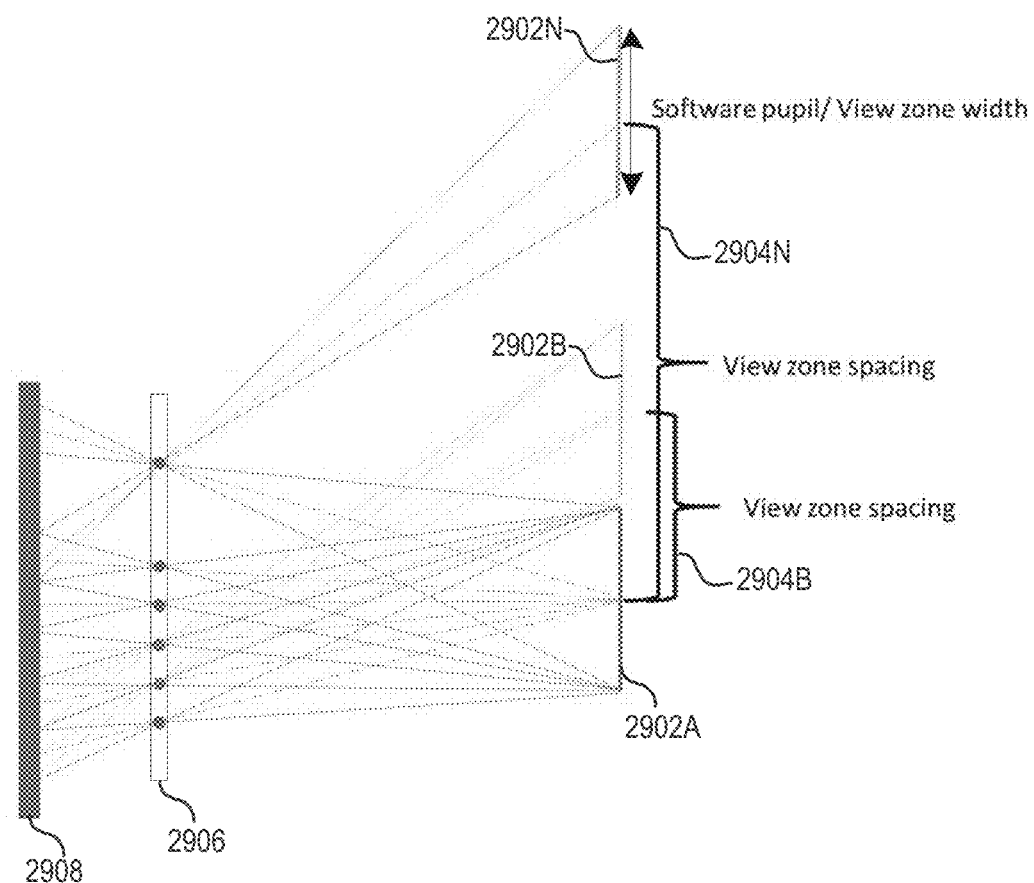
FIG. 29 is a schematic diagram illustrating view zone width and spacing, in accordance with one embodiment.

As illustrated schematically in FIG. 29, a digital display 2908 having a set of LFSEs 2906 disposed at a distance therefrom, will produce spatially recurring images in accordance with periodically recurring view zones 2902A, 2902B, 2902N. The view zone spacing may be prescribed by a spacing of the LSFEs 2906, as for example illustrated as view zone spacing 2904B between view zones 2902A and 2902B, and/or by software in opting to limit pixel use to certain areas thereby possibly imposing greater spacing between generated view zones, as for example illustrated by view zone spacing 2904N between view zones 2902A and 2902N. Correspondingly, a common software-controlled view zone width can be elected to more or less correspond with the user's pupil dimension, with some further consideration. For example, a view zone spacing that is too conservatively narrow will potentially allow multiple view zones to enter the user pupil at once and produce a less stable effect, whereas one that is too broad may have other undesirable effects as it relates to resolution, accuracy, etc.

Figure 30A:
FIGS. 30A and 30B are photographs of two light field images, one showing footprints of circular view zone (software pupil) overlapping with one another (30A) and the other generated by the same refractor device using a software pupil reshaping function to remove the overlap (30B), in accordance with one embodiment.
Figure 30B:

As illustrated in the photograph of FIG. 30A, and as will be described in greater detail below, an exemplary light field image generated in accordance with a suboptimal design results in optical artefacts that can be significantly suppressed using improved design considerations, as shown in corresponding FIG. 30B. Below are various examples, designed in accordance with different embodiments, to improve or optimize optical view zone output quality considerations, for example, in reducing or minimizing view zone boundary overlap, cross talk, interference or the like, and/or in optimizing image perception quality metrics.

Exemplary General Design Parameters

In one exemplary embodiment, refractors 102/702 may have the following hardware specifications:

Display size (e.g. display 108): 51.84 mm×51.84 mm;

MLA (e.g. LFSL 106): hexagonal 65 mm focal length, 1 mm pitch or 1.98 mm pitch MLA with various focal length options;

Tunable lens correction range: −5 Diopter to 10 Diopter per lens or −10 to 10 Diopter per lens.

In the case of a binocular device (comprising 2 joined or integrated monocular refractor devices 102, for example refractor 702 as illustrated in FIG. 7C), the form factor can be determined based on the binocular vision field of view (FoV) needed and the compactness of the device. For example, a device can be designed to have a distance between the display and user's eye of 320 mm, as considered in some of the below examples, whereas a desired FoV can be set to correspond with a standard Snellen chart test with dimensions of 240×300 arcminutes. Other such parameters may naturally be considered depending on the application at hand, available resources, costs and desired results.

Figure 25B:
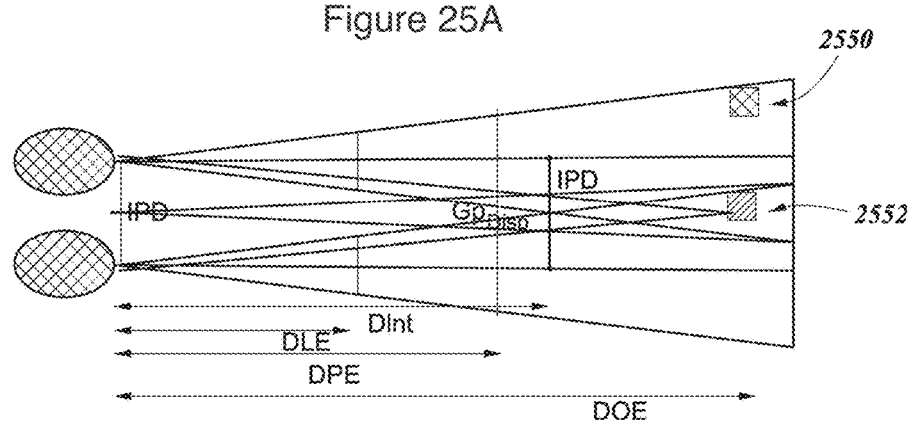

In some embodiments, the binocular vision FoV is determined as illustrated schematically in FIG. 25B, where the IPD is the interpupil distance, DLE is the MLA to eye distance, DPE is the pixel to eye distance and DOE is the projected virtual object distance to eye. Assuming that the gap between the two Binoculars is given by $G_{Disp}$ then the distance at which the display projections intersect with zero gap is given by:

$$D_{Int} = DPE \frac{IPD}{IPD - G_{Disp}}.$$

If the light field displays move to be centered around the center of each eye pupil, then this gap changes as a function of IPD and display width ($W_{Disp}$) as $G_{Disp}$=IPD−$W_{Disp}$. We can then define the view width as a function of the projected plane distance=IPD/DPE*DPO $$W_{Bi} \approx IPD\left(\frac{DOE}{D_{Int}} - 1\right);$$

$$FoV_{Bi} \approx 2\ atan\left(\frac{W_{Bi}}{2DOE}\right) = 2\ atan\left(\frac{IPD}{2}\left(\frac{1}{D_{Int}} - \frac{1}{DOE}\right)\right).$$

Furthermore, FIG. 25B shows an exemplary elaboration where a virtual object 2550 is perceived by both eyes, whereas a virtual object 2552 falls in the monocular region. For wide angle emission display where view for one eye can reach the other eye, a physical barrier can be used in between. Assuming that the gap between the two binoculars is given by $G_{Disp}$) then the distance ($D_{Int}$) at which the display projections intersect with zero gap is given by:

$$D_{Int} = DPE \frac{IPD}{IPD - G_{Disp}};$$

where DPE is the pixels/display to eye distance and the binocular view width ($W_{Bi}$) is a function of DPO, the projected plane distance to pixels/display, =(IPD/DPE)DPO:

$$W_{Bi} \approx IPD\left(\frac{DOE}{D_{Int}} - 1\right);$$

and $$FoV_{Bi} \approx 2\ atan\left(\frac{W_{Bi}}{2DOE}\right) = 2\ atan\left(\frac{IPD}{2}\left(\frac{1}{D_{Int}} - \frac{1}{DOE}\right)\right).$$

In some embodiments, moving the projected scene closer to the eye, as the eye accommodates, results in the resolution decreasing. This might cause a problem with stereoscopic vision known as the Vergence-Accommodation Conflict. Relative to a relaxed eye where the object is projected at infinity, the eye accommodation power as a function of virtual object distance is given by the reciprocal of the virtual object distance. To solve the Vergence-Accommodation Conflict, tunable lenses as described above may be used by directly applying a negative of the accommodation power (added to any power the tunable lens has to account for) for a system designed to work with relaxed eyes. If the range of accommodation needed of the projected virtual object plane is small it can be handled by the light field display.

For example, the image/object distance perceived by the eye (DOE) is related to the accommodation power (AP) of the eye via the following relationship:

$$DOE = \frac{1}{AP}.$$

With the above described systems and devices, some approaches to forcing the eye to accommodate to perceive a meaningful image may include:

1) Using external lens/tunable lens; or
2) Working within the correction range of the light field display to shift the correction power.

For an un-aberrated eye, the intersection point on the retina of the incoming rays is only dependent on the angle of incidence at the pupil. Hence, in some embodiments, if the total system is reduced to a single lens and an un-aberrated eye, the light-field and image distance may be calculated more readily. Using an external lens with accommodation power to give a perception of certain image distance, the net power (NP) can be calculated using the equivalent power of the external lens power (ELP) and the accommodation power of the eye, in addition to any spherical error (SE) of the eye:

NP=AP+SE+ELP−DEL(AP+SE)ELP where DEL is the distance between the pupil/eye lens to the external lens.

In some embodiments, an IPD distance smaller that the display width can be achieved using mirrors as will be explained bellow. Therefore, to make a reconfigurable platform, in some embodiments, a mirror assembly may be accounted for with ~40 mm. This also maintains the compactness of the device. For example, in some embodiments, using a 320 mm display to eye distance (excluding the mirror assembly) and designing at the central power correction of the light field, the arrangement for the hardware components can be optimized for different objectives, as shown in Table 1 below:

TABLE 1

|  | (a) | (b) | (c) | (d) | (e) | (f) | (g) |
| --- | --- | --- | --- | --- | --- | --- | --- |
| MLA pitch, focal length (mm) | 1, 65 | 1,65 | 1, 65 | 1.98, 46 | 1.98, 46 | 1.98, 32.5 | 1.98, 55 |
| Display to MLA distance (mm) | 50 | 34.5 | 40 | 86 | 37 | 49 | 47 |
| Angular pitch (arcminute) | 0.36 | 0.49 | 0.56 | 0.7 | 0.89 | 0.93 | 0.95 |
| Center light-field correction power (diopter) | −2.06 | −2.78 | −2.6 | −7.4 | −2.1 | −5.73 | −1.68 |
| Cutoff spatial resolution (arcminute) | 0.85 | 0.39 | 0.52 | 0.7 | 0.38 | 0.53 | 0.52 |
| View zone spacing (mm) | 6.4 | 9.3 | 8 | 7.36 | 17.12 | 12.9 | 13.5 |
| View zone separation from 5 mm pupil (mm) | −0.42 | −0.3 | −0.35 | −0.17 | 3.6 | 2.17 | 2.4 |
| Minimum software pupil diameter (mm) | 2.25 | 4.9 | 3.7 | 2.7 | 4.9 | 3.58 | 3.65 |

If the light field that corrects for power of $P_{LF}$ (within the correction range of the light field around the center of quality $P_Q^{OS}$, then NP should be equal to this value to generate a meaningful image on retina:

$$P_{LF} = AP + SE + ELP - DEL(AP + SE)ELP = \frac{1}{DOE} + SE + ELP - DEL(AP + SE)ELP.$$

Having this, the image distance/inverse distance can be calculated and passed to light field rendering algorithm based on the desired image distance. In some embodiments, this is related to the $P_{LS}$ as follows:

$$\frac{1}{DOE_{Algorithm}} = P_{LF}.$$

With this unified implementation, the image/object is set at the real desired image distance and the ray tracing method is used to correct, using light field, for the power $P_{LS}$ as calculated above.

Figure 26A:
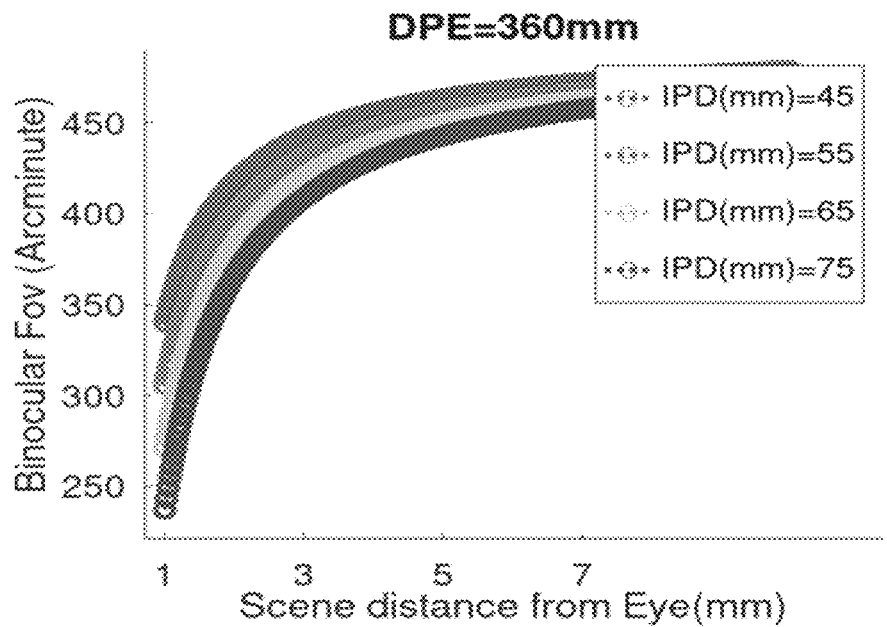
FIGS. 26A and 26B are plots illustrating the change in binocular field of view (FoV) in arcminutes with respect to the scene distance from the eye in mm, in accordance with different embodiments.
Figure 26B:
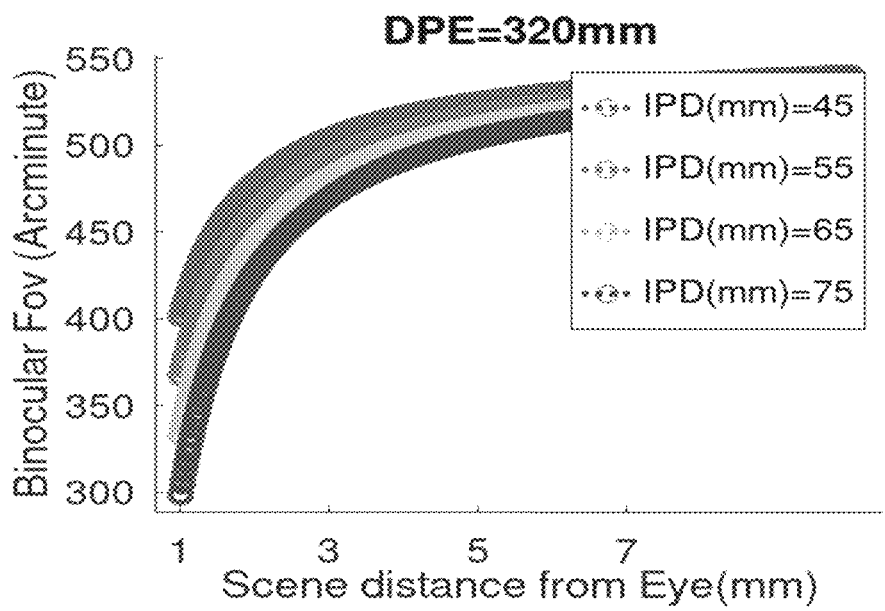

Also, since the angular pitch is inversely dependent on the FoV, the distance between the eye and the display should be maximized to minimize the achieved angular pitch. In some embodiments, the IPD range may be between 40 mm and 76 mm. Then, for example, the maximum distance from the display to the eye of 360 mm allows to project an image/virtual object of distance down to ~one meter, as shown in FIGS. 26A and 26B, which corresponds to a 1 diopter light field correction.

Figure 25C:
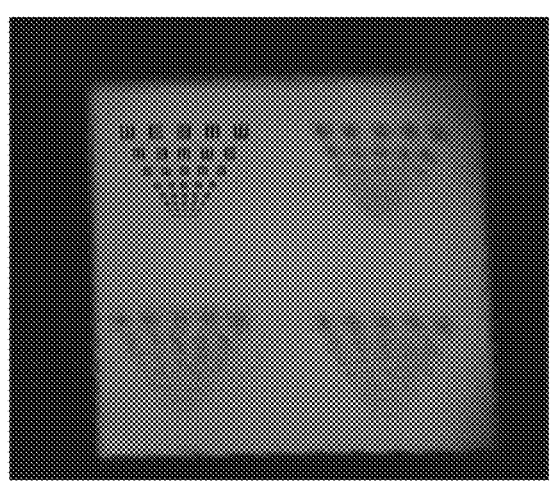

FIG. 25C shows an exemplary photograph of a view of a light field image generated using an embodiment of refractor 102 having the specifications mentioned in column (a) above, the light image showing four optotypes at different dioptric powers disposed in a quadrilateral arrangement.

Figure 25D:
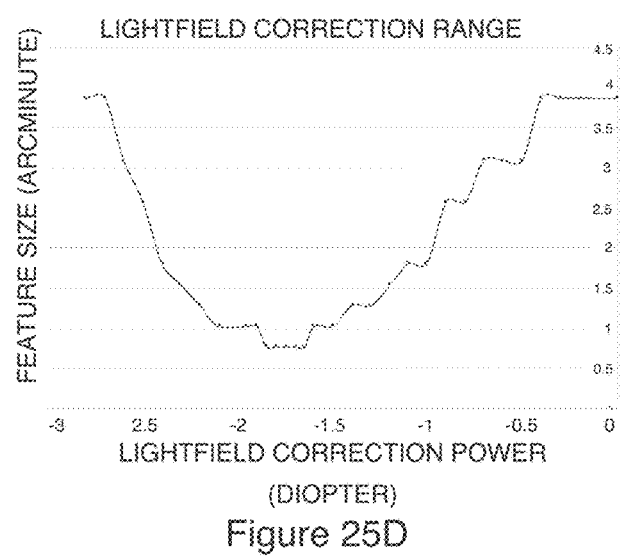

In some embodiments, using a tunable lens, the dioptric power range of such an embodiment of refractor 102 is:
  Tested tunable lens correction range for 1 arc minute feature: −12D and 8D within the specified range of the tunable lens power; and −12D to 10D beyond the specified range by the manufacturer; and
  Tested Light field correction power range: ~0.6D for 1 arcminute feature size, and up to ~2.85D for feature size below 4 arcminutes. This is plotted in FIG. 25D and corresponds to possible cylindrical correction range of 1.2D for 1 arcminute feature size, and up to 5.7 Diopters for feature size below 4 arcminutes.

In some embodiments, the separation between the view zones can be maximized at the expense of the angular pitch spec to minimize/eliminate multiple image projection; for example, refractor 102 may have the specifications in column (b).

Furthermore, in some embodiments, the light field can be optimized to maximize the range of correction by adjusting the beam size on cornea, or alternatively spot size on retina, as will be explained later. For this case, the specs in column (c) can be obtained for a 320 mm form factor.

Other MLA specs can be used based on availability. For instance, an MLA with a hexagonal pattern and 1.98 pitch can be used with a focal length of 46 mm, which allows for greater view zone separation while maintaining an angular pitch smaller than 1 arcminute. For a long-range retinal spot size, the specs in column (d) are obtained, whereas releasing this constraint results in the specs in (e).

Yet, it is still possible to have both positive view zone separation and a retinal spot size that maximizes the light field correction range. For instance, the 1.98 pitch MLA with other focal length values like 32.5 mm and 55 mm result in specs in columns (f) and (g).

View Zone Optimization

As noted above, various design considerations come into play in optimizing the output of a light field device as contemplated herein, notably to reduce or minimize interfering view zone artefacts while increasing or optimizing image perception quality (resolution) and user comfort while maintaining required field of view given prescribed form factor. As outlined below, various optical hardware configurations are proposed, in accordance with different embodiments, to enhance view zone output and perception thereby improving device/system performance. Some of these optical hardware solutions may be used in isolation, or in combination with other solutions, to provide an optimal result.

For example, in some of these embodiments, output optical components are used alone or in combination to optically favour and guide a prescribed view zone in alignment with the user's pupil, while reducing an interfering influence from adjacently produced view zones. For instance, as illustrated schematically in FIG. 29, a desired image rendering perspective may be optimized for consumption via predominant view zone 2902A, which has a defined view zone width and spacing with adjacent view zones. In accordance, with some of the below-described embodiments, output optical components can be disposed, aligned and/or configured to favour direction of this predominant view zone toward the user's pupil while reducing or minimizing interference that may potentially arise from an adjacent view zone (e.g. view zone 2902B). Indeed, this may become more important where other intervening optics, such as a variable lens reel or dynamically adjustable fluid lens is interposed within the optical path of this predominant view zone to extend a dioptric range of the device, and which may adversely interface with adjacent view zones to produce undesirable effects. Likewise, the provision of a binocular device, each light field optical path thereof producing a respective predominant view zone for consumption by a corresponding user pupil, possibly in accordance with respective optical perception adjustment factors, may benefit form respective predominant view zone isolation and/or guidance hardware to provide an improved visual experience, not only in avoiding cross-talk between left and right view zones, but also, or alternatively, in accommodating conflicting dimensions or geometries between light display optics, device form factors and/or average user facial attributes such as IPD, pupil size, etc. Furthermore, the provision of intervening optics to, for example, adjust or increase a dynamic perceptive adjustment (e.g. dioptric) range of the light field device, may further introduce view zone conflicts or artefacts that may be adequately addressed using one or more of the below-described solutions.

View Zone Isolator

In some embodiments, as illustrated schematically in FIG. 25A and with further reference to FIGS. 7A to 7C, a monocular refractor 102 (or each left/right portion of binocular refractor 702) may further comprise a structural non-refractive view zone isolator forming a non-refractive view zone isolating aperture therein (herein shown having circumscribing edges/boundaries 2502) to remove or block visual artefacts caused by adjacent view zones concurrently created by the pixel display 108 and LFSL 106. For example, within the context, and to follow from the above example in respect of FIG. 29, an aperture of this view zone isolator may be positioned along an optical path of predominant view zone 2902A and dimensioned so as to maximize throughput of optical rays participating in the formation of the perceived image for this particular view zone, while minimizing throughput of optical rays participating in the formation of corresponding images perceivable in accordance with adjacent view zones (e.g. view zone 2902B), and that, without imparting any refractive optical impact on the formation or perception of the predominant view zone image at the pupil.

Within the context of FIG. 25, so to minimize further view zone interference or cross talk that may be induced by intervening optics, such as tunable lens 2504, the view zone isolator may be disposed upstream of the tunable lens 2504 thereby predominantly limiting optical throughput toward this tunable lens to light rays corresponding to the predominant view zone of interest. Naturally, similar considerations may apply to an optical setup comprising a dynamic lens reel, as can other intervening optics be considered without departing from the general scope and nature of the present disclosure.

As outlined above, since different optical and software considerations may come into play, in different embodiments, to produce different view zone widths, so can different view zone isolators or isolator locations be considered to maximize its beneficial impact.

Furthermore, respective view zone isolators may be used in a binocular implementation to isolate corresponding view zones for each eye, and further possibly to obstruct left-right monocular view zone interference that could otherwise interfere with the production of a comfortable binocular experience. Indeed, in some embodiments, a singular light field display may be used to produce binocular views, as can respective side-by-side displays, whereby respective predominant view zones are created and directed to a corresponding user eye pupil, but whereby adjacent view zones so produced, unless appropriated isolated out, could cause adverse left-right view zone contamination. Accordingly, binocular view zone isolation may be appropriately implemented to minimize such adverse effects.

Lateral View Zone Output Re-Alignment

In some embodiments, refractor 102 (or each right/left portion of binocular refractor 702) may further include additional optical components or assemblies, as introduced above, to non-refractively guide or realign a predominant view zone toward a device output and corresponding user pupil location/configuration. For example, in some embodiments and as illustrated schematically in FIG. 27A, refractor 102/702 may comprise, for each eye, a corresponding view zone redirecting mirror assembly 2702 configured to act as a periscope-like device for redirecting the light field emitted by the light field display along a redirected optical path, for example, to accommodate a physical mismatch between device performance and/or form factor requirements and average physical characteristics of a user's face (e.g. eye position, IPD, etc.). For example, in some embodiments, two monocular devices joined together such as the one illustrated in FIG. 7C (e.g. refractor 702) may have components that are such that the output from each light field display (or each light field display portion of a common display) is further apart than that imposed or preferred to accommodate a user's (average or input) IPD. This may be a result, for example, of display requirements to achieve a desired output resolution or brightness, for example, whereby displays of a certain minimum width are required that, when disposed side-by-side, result in the non-ideal formation of overly spaced-apart predominant binocular view zones. Accordingly, rather than to accept formation of sub-optimal view zone characteristics or constrain or limit use of or access to available pixels, non-refractive view zone redirection optics may be aptly employed to address such geometrical/dimensional mismatches.

Figure 27A:
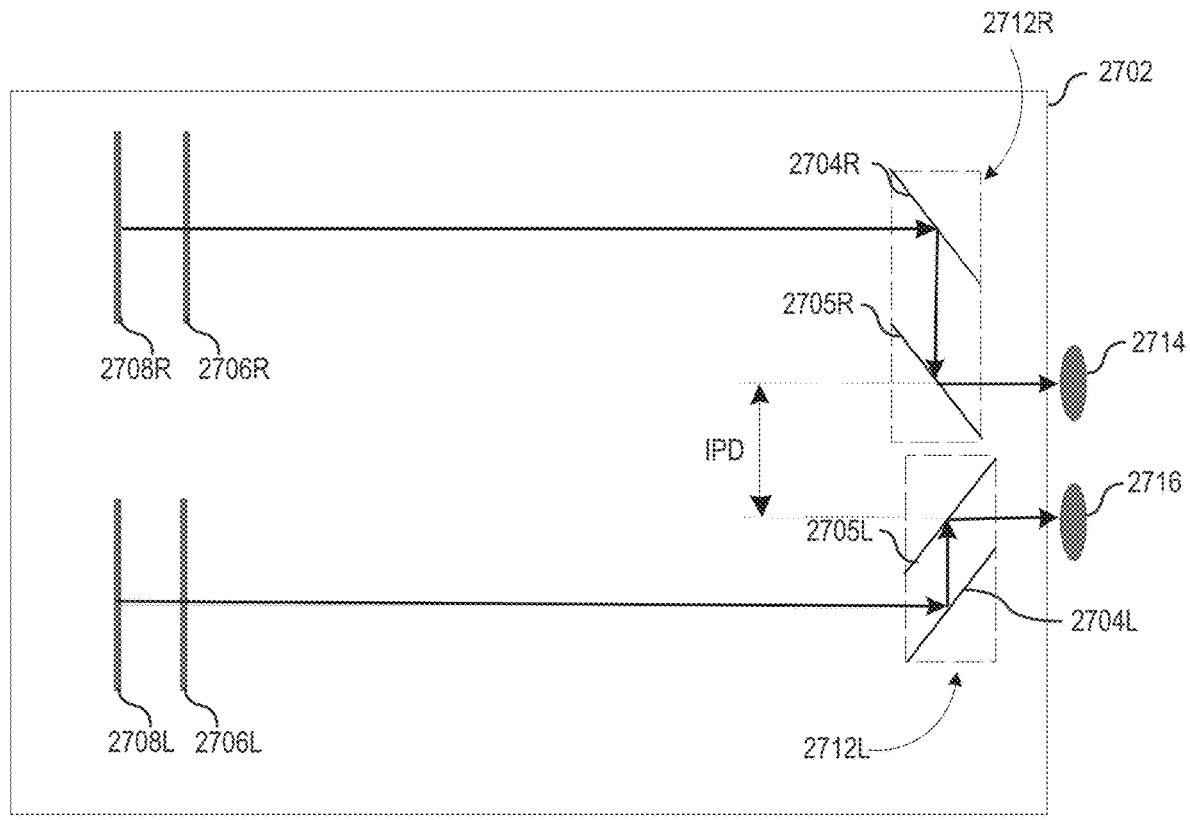
FIGS. 27A and 27B are schematic diagrams of an exemplary binocular refractor device comprising mirror assemblies configured to redirect light field images so that they exit the refractor device in accordance with the user's interpupillary distance, in accordance with one embodiment.

Indeed, in some embodiments, one or more mirror assemblies are used to redirect the light field image from each display (portion) so that the spacing between the light field outputs at the eyes is substantially equal to the IPD. In FIG. 27A, which shows schematically a top-down view of a binocular refractor 2702, two assemblies 2712R and 2712L are shown, each comprising mirror pairs 2704R and 2705R, and 2704L and 2705L, respectively, to move the respective right and left view zones generated by the right and left LFSLs 2706R/L and pixel displays 2708R/L, respectively, to the appropriate location for the right (2714) and left (2716) tunable lens, themselves in line with respective eye outputs according to a fixed or set user IPD, respectively.

In some embodiments, the mirror assemblies 2712R/L may be rotated to allow for better IPD adjustment.

In some embodiments, a position of the mirror assemblies 2712R/L may be dynamically adjustable along with the tunable lenses (2714, 2716), and/or other light field device components such as light field display components, for example via one or more actuators (e.g. electrical motors, etc.). In some embodiments, adjustments may be made via a dial, button or lever located on the casing of refractor.

Figure 27B:
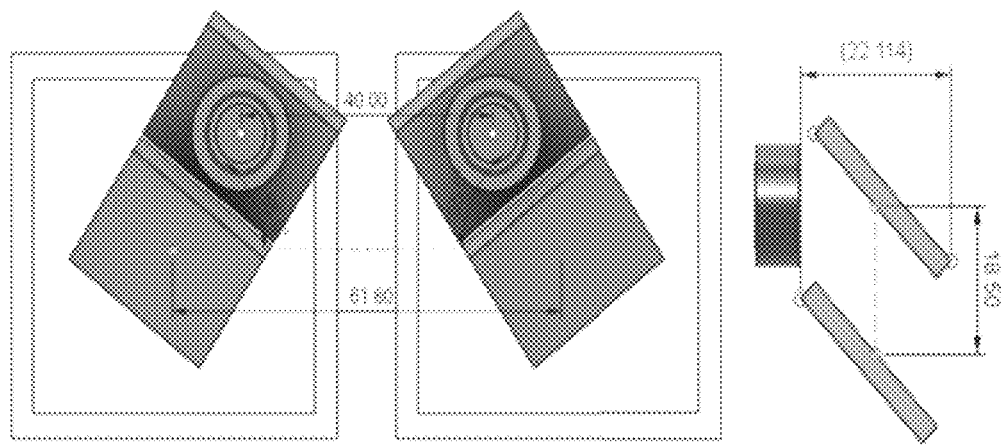

An exemplary embodiment of mirror assemblies is shown in FIG. 27B, constructed to reduce a minimum achievable IPD distance from 61 mm to 40 mm in this example. For this exemplary arrangement the tunable lenses are placed close to the eye at the exit aperture of the assembly. Using square mirrors of 25.4 mm side length and displaced ~18.5 mm apart, the optical path length added of ~40 mm is added to the 320 mm design length in the previous section to a total of ~360 mm optical pathlength. With this displacement rotation of ~55°, the minimum IPD is reduced from 61.8 mm to 40 mm. Here the difference between the 51.84 mm display active area width and the un-adjusted minimum IPD of 61.8 mm is consumed with hardware constraints. The width of the Mirrors is chosen to accommodate the light field/view zone spread. For instance, the maximum spread at the input aperture of the mirror assembly is the maximum for option (b) in the Table 2 below which is ~18 mm. Since the mirrors are mounted at a 45° angle, the maximum light field spread that can be accommodated is ~18 mm as required.

Table 2 below show some exemplary embodiments for specs with the mirror assembly installed:

TABLE 2

|  | (a)-p | (b)-p | (c)-p | (d)-p | (e)-p |
|---|---|---|---|---|---|
| MLA pitch, focal length (mm) | 1, 65 | 1.98, 46 | 1.98, 46 | 1.98, 32.5 | 1.98, 55 |
| Display to MLA distance (mm) | 42 | 74.5 | 38 | 46.5 | 48 |
| Angular pitch (arcminute) | 0.54 | 0.81 | 0.87 | 0.96 | 0.94 |
| Center light-field correction power (diopter) | −2.29 | −6.05 | −1.85 | −4.86 | −1.45 |
| Cutoff spatial resolution (arcminute) | 0.52 | 0.7 | 0.39 | 0.51 | 0.53 |
| View zone spacing (mm) | 8.57 | 9.56 | 18.75 | 15.33 | 14.85 |
| View zone separation from 5 mm pupil (mm) | 0 | 0.92 | 4.43 | 3.28 | 3.12 |
| Minimum software pupil diameter (mm) | 3.68 | 2.72 | 4.9 | 3.77 | 3.62 |

While such design specifications are provided with respect to select exemplary embodiments of light field devices, various others are similarly contemplated within the scope and nature of the disclosure.

Generally, for a given device configuration (e.g. devices (a)-p to (e)-p in Table 2), the range of perceivable depths that may be generated by the device (also referred to herein as a 'corrective range') within application-specific parameter preferences (e.g. a designated content resolution for an eye exam, or the like), may be considered as dependent on the focus spot size of light field beams, which defines a cut-off spatial frequency that may be resolved, and the spatial pitch of focused beams. The corrective range of a device may be maximised in view of both of these considerations, in accordance with various embodiments.

For example, FIGS. 35A to 35I are plots characterising various parameters of exemplary light field display systems, wherein parameters are plotted for a range of MLA pitches (e.g. lenslet diameters) as a function of MLA focal length. In these examples, various calculations are shown for devices comprising a digital display screen with a pixel pitch of 24 μm disposed to provide a display-to-eye distance/optical path length of 365 mm, wherein the pupil diameter is considered to be 5 mm.

Figure 36A:
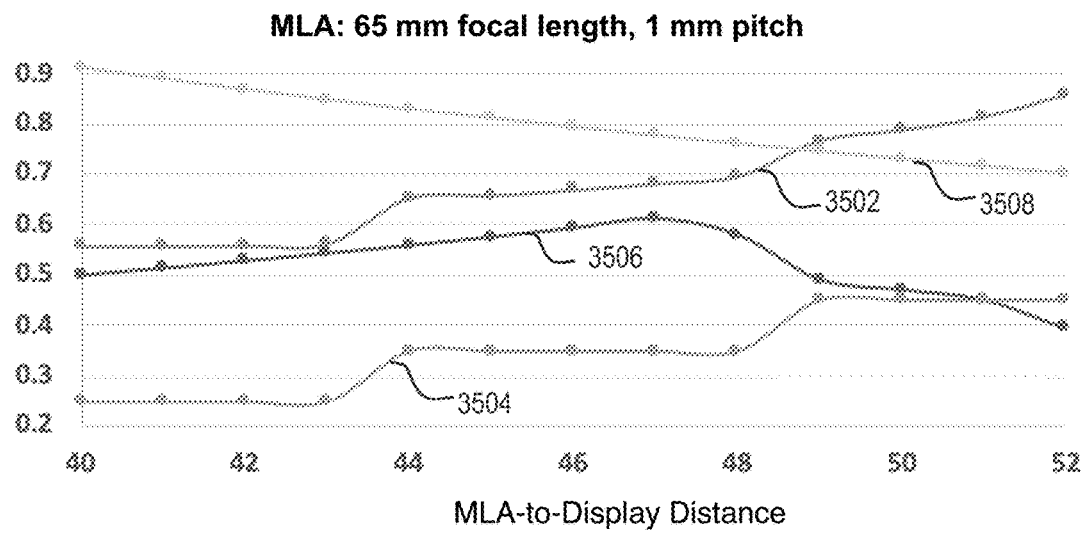
FIGS. 36A and 36B are plots illustrating various device parameters as a function of different exemplary light field device configuration specifications, in accordance with various embodiments.

Such plots may be used to determine various device properties for various component selections and/or placements within a device. For example, for an MLA focal length of 65 mm and pitch of 1 mm, a display-to-MLA distance of 40 mm to 43 mm provides average cut-off angular pitch 3502 of approximately 0.55 arcminutes, as shown in the plot of FIG. 36A. For a desired 1 arcminute resolution for, for instance, an eye exam, the Light Field Correction range (diopter) 3504 of the light field device is approximately 0.25 diopters while maintaining angular pitch specs below 1 arcminute. This range may be increased to approximately 0.45 diopters by extending the display-to-MLA distance to approximately 49 mm to 52 mm. However, this may be at the expense of the cut-off pitch, which, while still less than 1 arcminute, may result in a light field image with lower contrast. However, as the light field power range may be of particular importance for various applications (e.g. for cylindrical power and/or multi-depth correction), this trade-off may be acceptable or preferred, in accordance with some embodiments. FIG. 36A also plots the average pitch (ArcMin) 3506, and the view zone width (cm) 3508, as a function of MLA to display distance.

Figure 36B:
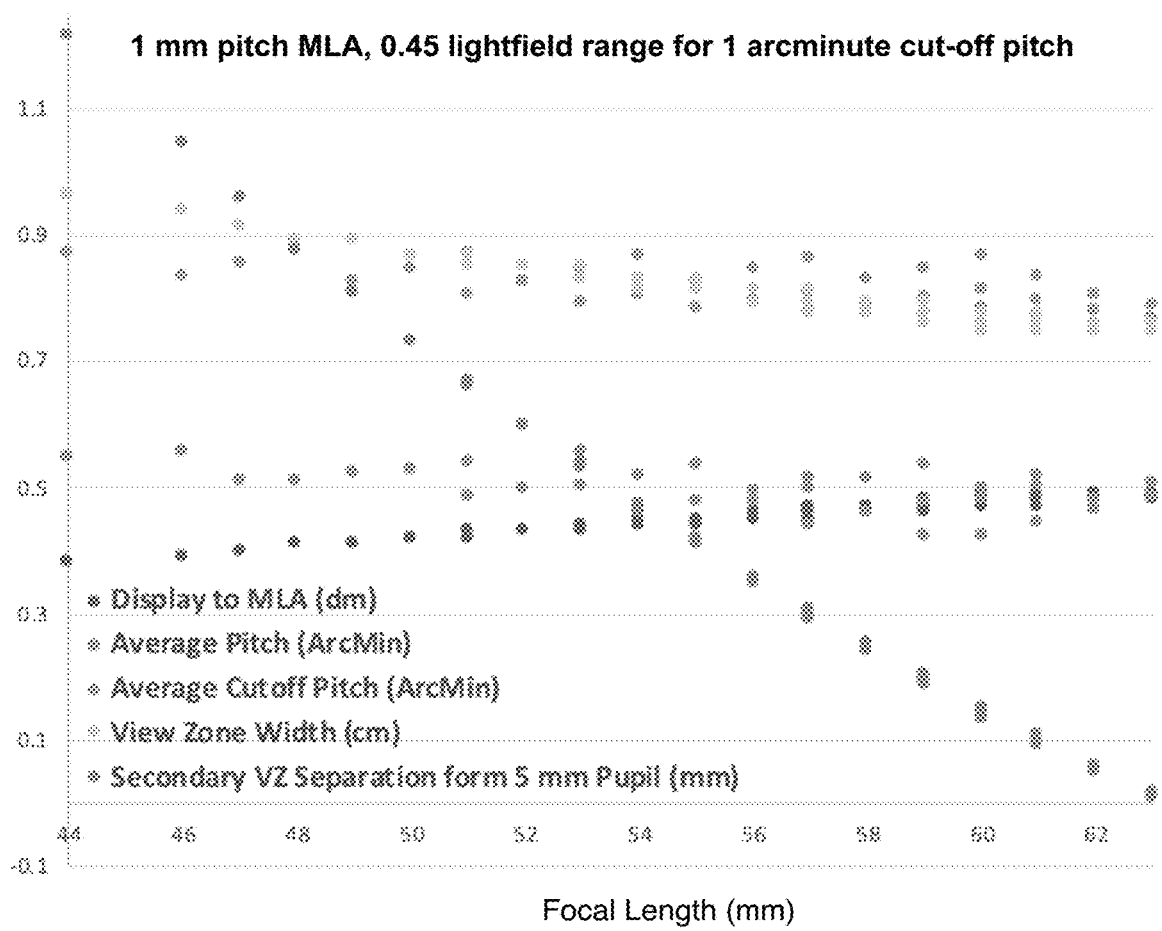

For this latter case, the secondary view zone separation from a 5 mm pupil is approximately zero (not shown in FIG. 36A). This may be undesirable for some applications seeking to minimise the possibility of secondary zone overlap and/or seeking to allow for eye movement. Some alternatives for minimising view zone overlap are presented in the plot of FIG. 36B, in accordance with some embodiments. From FIG. 36B, it is observed that an MLA with a 1 mm pitch and focal length between 47 mm to 53 mm maintains an average pitch of approximately 0.5 arcmin. Within this range, an MLA focal length of between 47 mm and 48 mm maximises view zone separation from the pupil to ~0.9 mm. In embodiments employing tunable lenses (e.g. with clear aperture to 5.8 mm), some of this view zone separation may be sacrificed to achieve an average pitch approaching 0.5 arcminutes, minimising the cut-off angular pitch while maintaining separation between the secondary view zone and the tunable lens aperture. This may be achieved using, for instance, an MLA with a focal length between 52 mm and 53 mm, with a display-to-MLA distance of 43 mm and 44 mm, respectively, for a 365 mm display-to-eye distance.

It will be appreciated that while such examples relate to embodiments differing by 1 mm in MLA focal lengths and display-to-MLA distances, the average angular pitch may be further tuned by displacing the MLA in accordance with smaller increments. For instance, for an MLA of 53 mm focal length, the angular pitch may vary from ~0.5 arcminutes to ~0.56 arcminutes for display-to-MLA distances of 44 mm and 43 mm, respectively, in accordance with some embodiments.

As noted above, in some embodiments, binocular refractor 702 (for example as illustrated in FIG. 7C or 27A), may be used to execute one or more vision tests. While such a binocular device may retain every feature or improvement described above with respect to monocular testing (for example method 800 described above), the ability to generate vision corrected light field images for both eyes simultaneously with the binocular device enables additional features.

Figure 33:
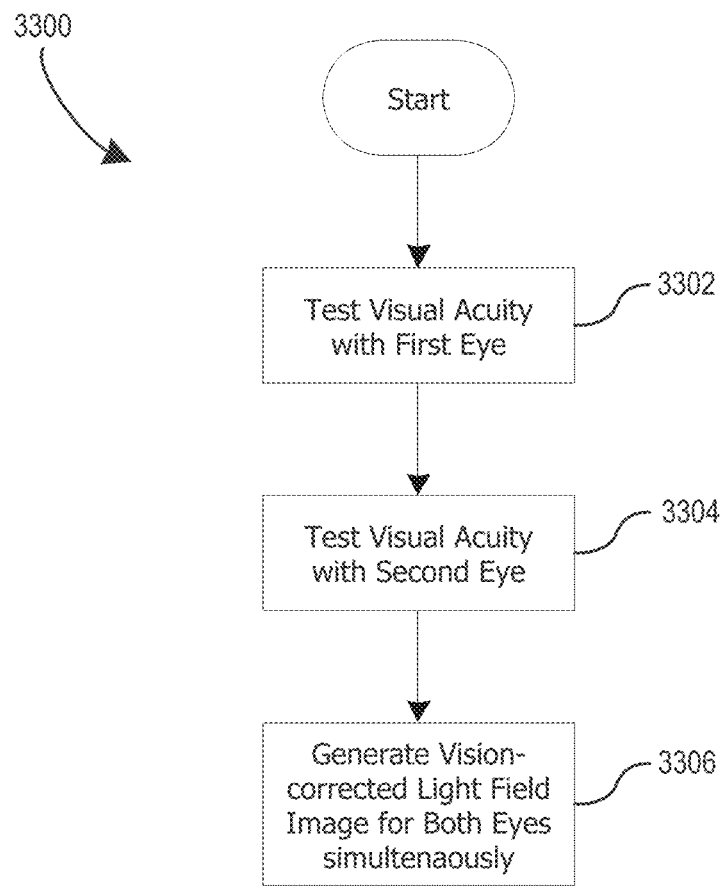
FIG. 33 is a process flow diagram of a vision testing method using a binocular light field refractor, in accordance with one embodiment.

With reference to FIG. 33, and in accordance with one exemplary embodiment, a dynamic subjective vision testing method using a binocular version of vision testing system 100, generally referred to using the numeral 3300, will now be described. Generally, method 3300 seeks to diagnose a patient's reduced visual acuity and produce therefrom, in some embodiments, an eye prescription or similar.

Method 3300, in this exemplary embodiment, starts at steps 3302 and 3304, by doing a monocular vision test on a first eye and a second eye, respectively. This may include, for example, executing method 800 described above for each eye, one after the other, so as to determine the respective visual acuity thereof. When testing one eye on the binocular device, system 100 may communicate to the user to keep the other eye closed, or it may display a black image or block the aperture in front of the other eye so as not to disturb or influence the test. After steps 3302 and 3304 are executed, system 100 will generally have determined the required vision correction parameters of each eye (for example in the form of the spherical dioptric power 1026, and in some cases cylindrical dioptric 1030, cylinder axis angle 1032 or higher order parameters). Then, at step 3306, the binocular version of refractor 102 can show a single vision-corrected image to both eyes simultaneously, wherein the corresponding vision correction parameters have been applied to the light field image presented to each eye. The user will perceive this image as a single image (e.g. as viewing the same image or object with both eyes), not as twice the same image/content being displayed to each eye individually. Below, different means of generating or projecting such light field images or content via two light field displays (e.g. a pair of digital display and MLAs, or respective portions of a shared display and/or MLA) so as to be perceived by each eye as the same object or image, will be discussed. This last step (3306) is meant, in this example, to simulate the effect of wearing the correct prescription glasses, to show the user a preview of the resulting vision acuity improvement.

In some embodiments, the light field rendering methods described above may be slightly modified to account for both eyes viewing the same image/content when rendering these images using binocular light field refractor 702. For example, this may include cases where a same image is shown by both left and right light field displays so as to be perceived as being the same image by both eyes simultaneously.

In some embodiments, the light field generated from each light field display 104 may thus be shifted accordingly for each eye so as to appear centered therebetween. In some embodiments, this may include shifting the general position or location of the light field image so as to be re-centered between the eyes (i.e. shifted horizontally by a value equal to half the interpupillary distance, for example, which distance may be preset as a static average IPD distance, or dynamically adjusted as a function of a corresponding IPD adjustment for respective optical outputs and non-refractory mirror assemblies as noted above).

Figure 34A:
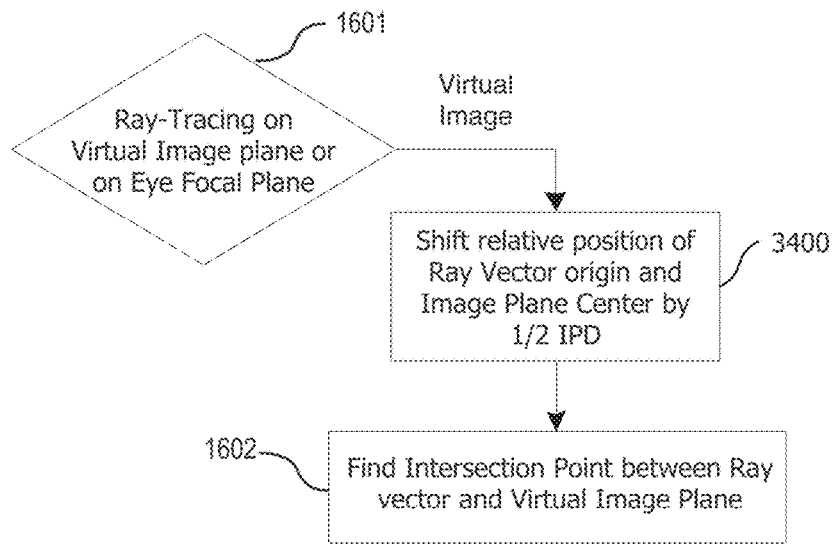
FIGS. 34A and 34B are process flow diagrams illustrating additional steps used to enable stereoscopic vision for method 1100, either when ray-tracing on a virtual image plane (34A) or on an eye focal plane (34B), in accordance with respective embodiments.

In one embodiment, and as illustrated in FIG. 34A with added reference to FIGS. 11, 15 and 16, the virtual image ray-tracing of method 1100 may be modified so that before extending ray 1504 to intersect with the virtual image plane 1502 in sub-step 1602 to identify the image portion, the origin point of ray 1504 on the pupil (e.g. point 1416) may be shifted horizontally by half the interpupillary distance (IPD) (to the right if right eye, or to the left if left eye) in a new step 3400. Then ray 1504 is projected from this new location (but with the same orientation) to intersect with virtual image plane 1502 as discussed above. Inversely, the same result would be achieved by horizontally shifting the location of virtual image plane 1502 instead by the same distance, but in the opposite direction.

Figure 34B:
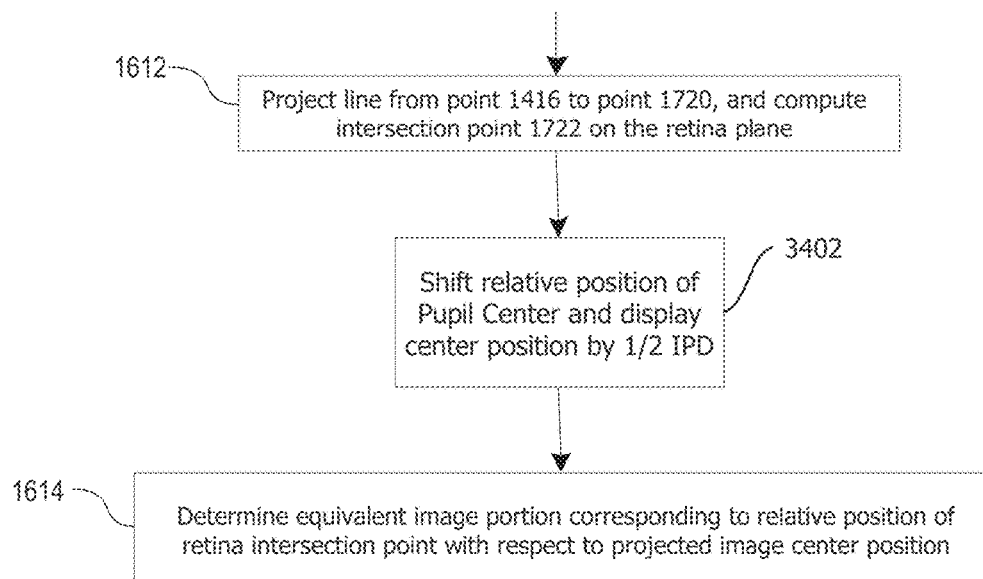
Figure 35A:
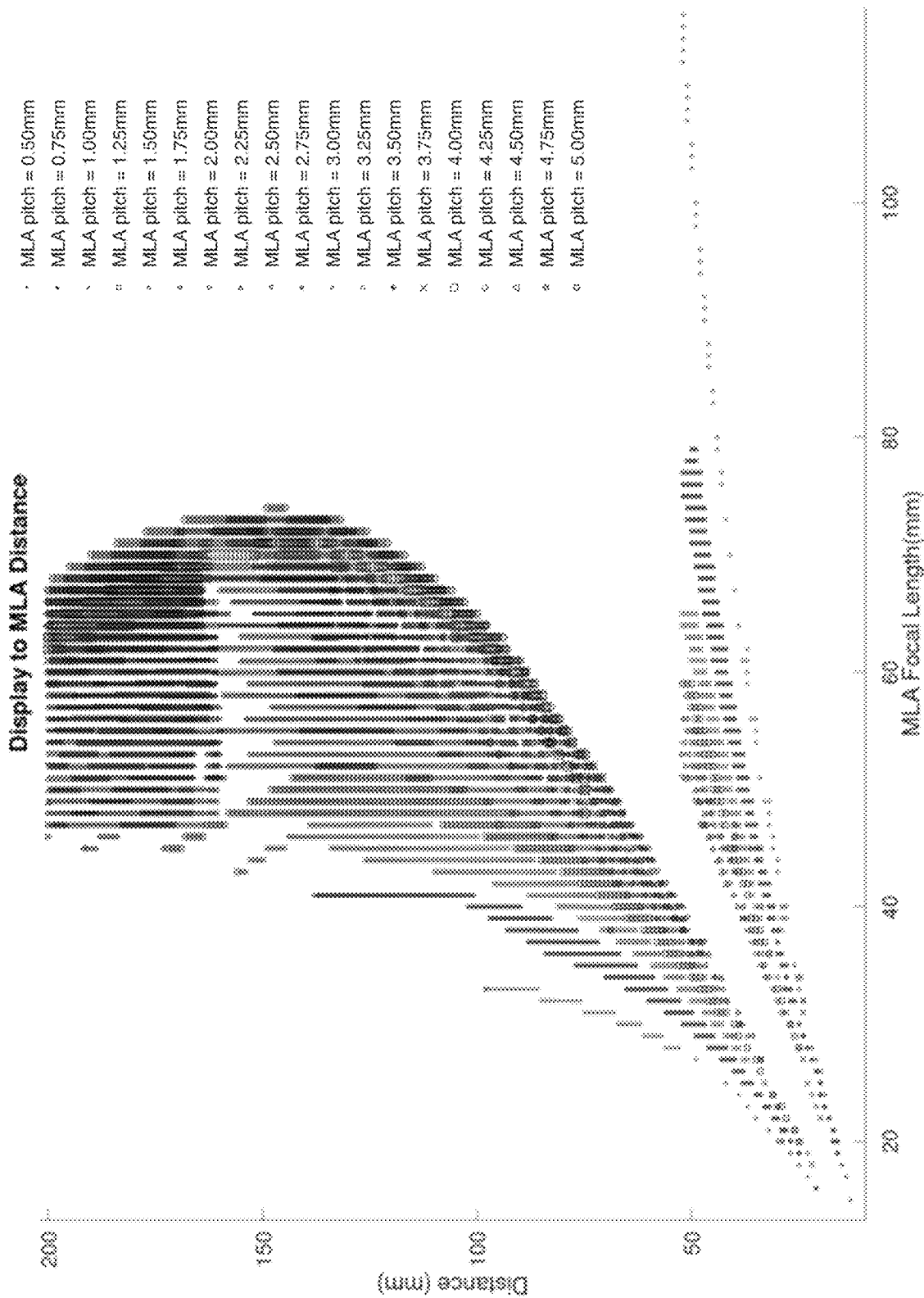
FIGS. 35A to 35I are plots illustrating exemplary parameter spaces with respect to various exemplary light field device configurations, in accordance with various embodiments.
Figure 35B:
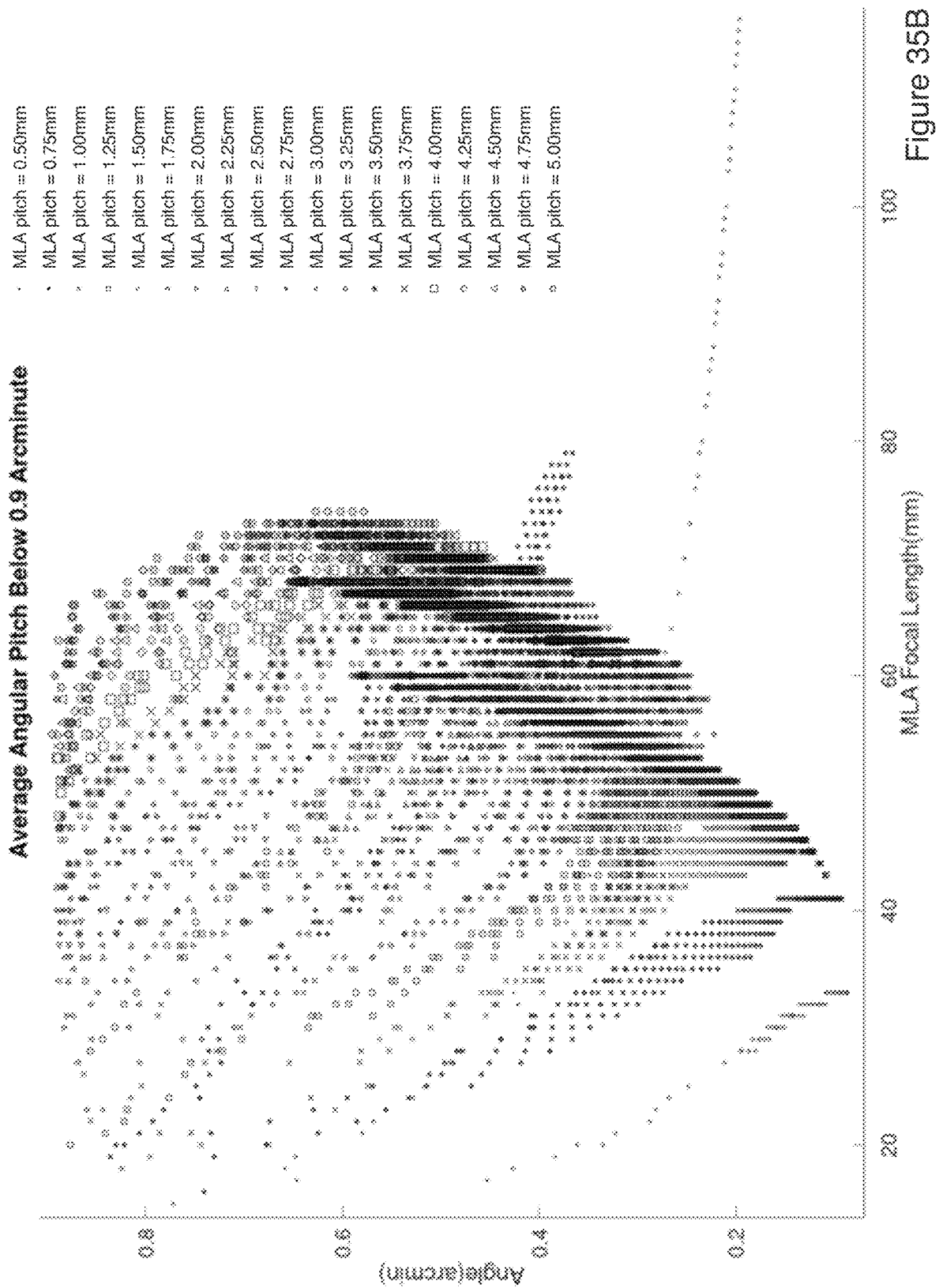
Figure 35C:
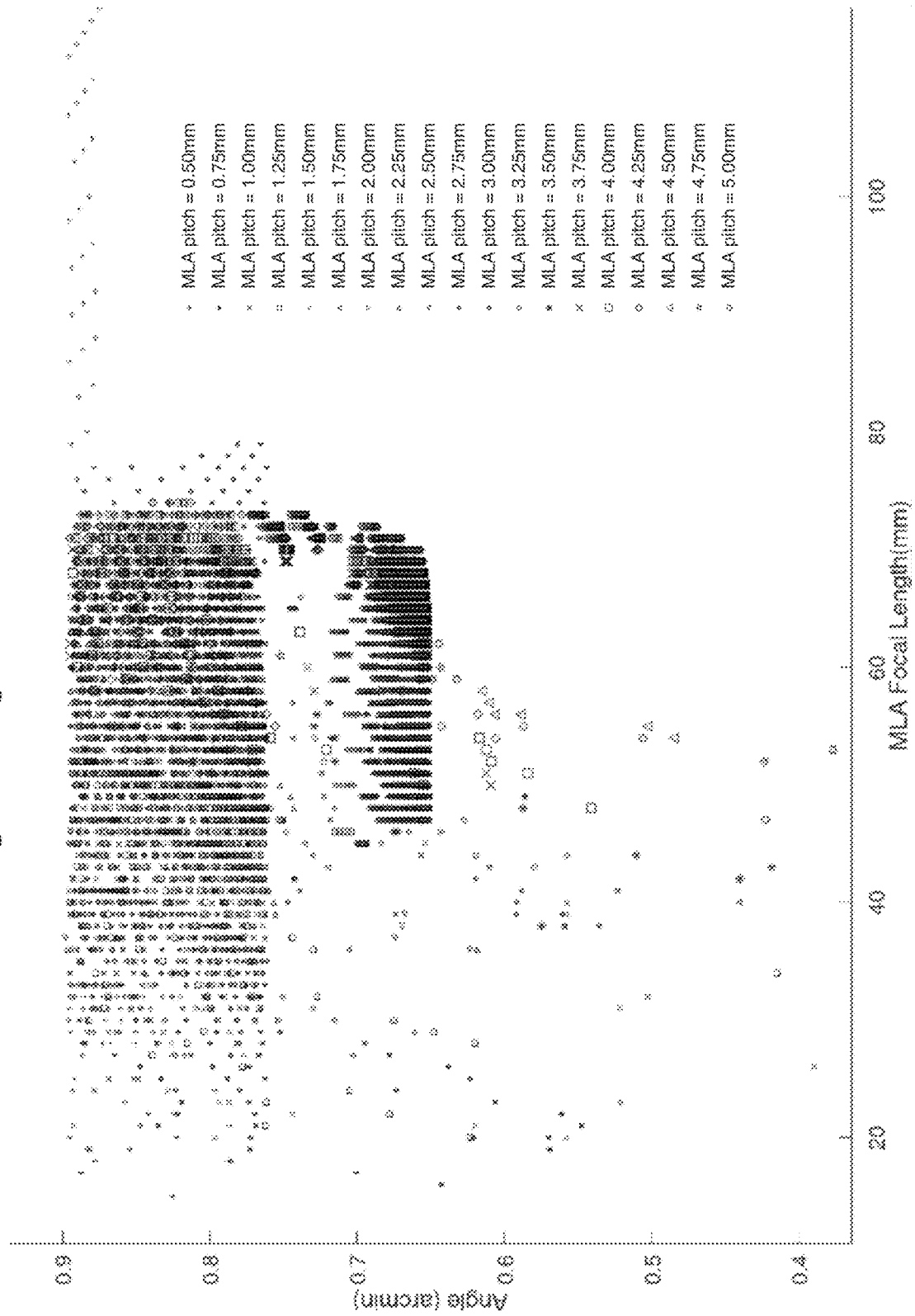
Figure 35D:
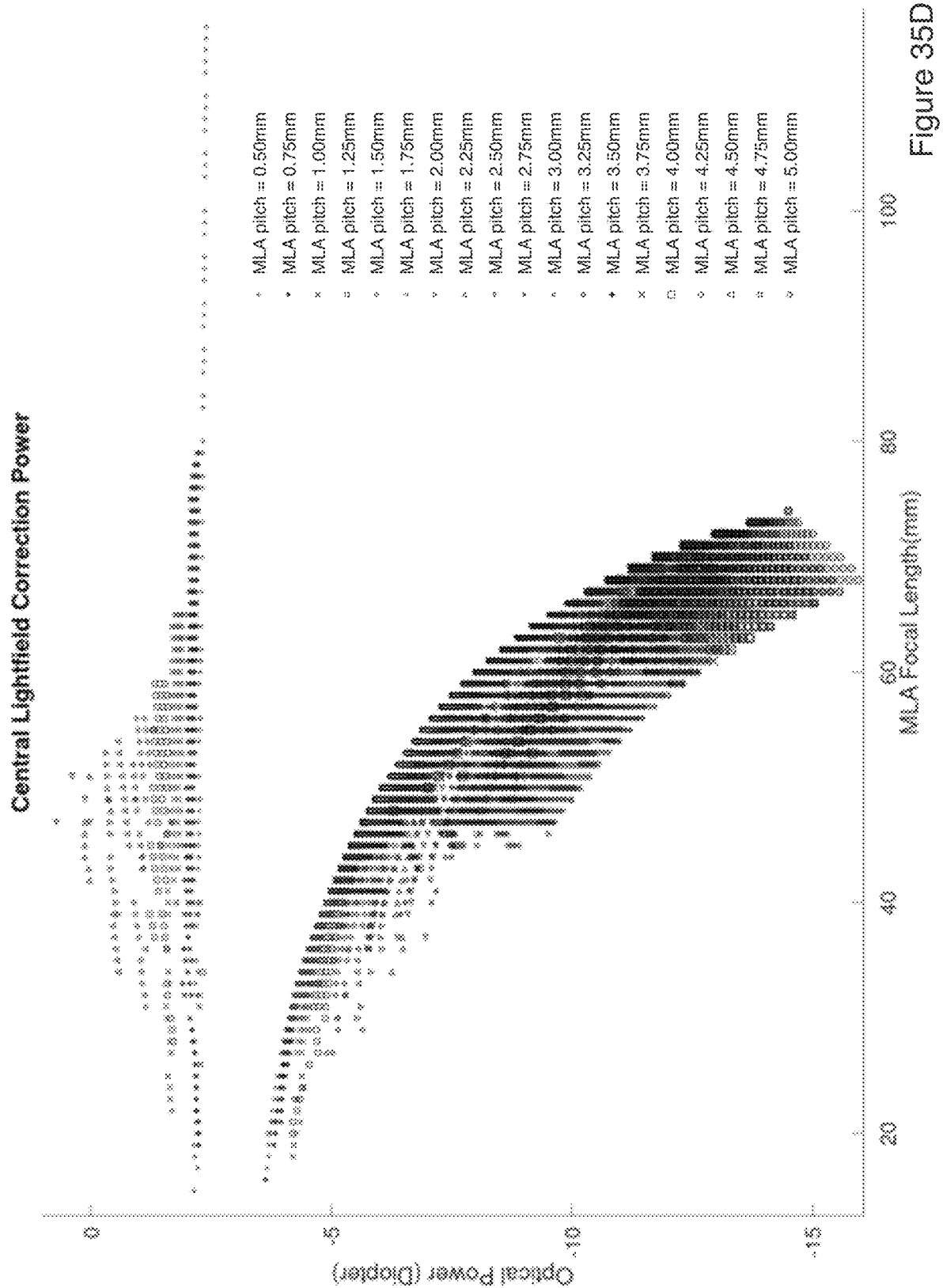
Figure 35E:
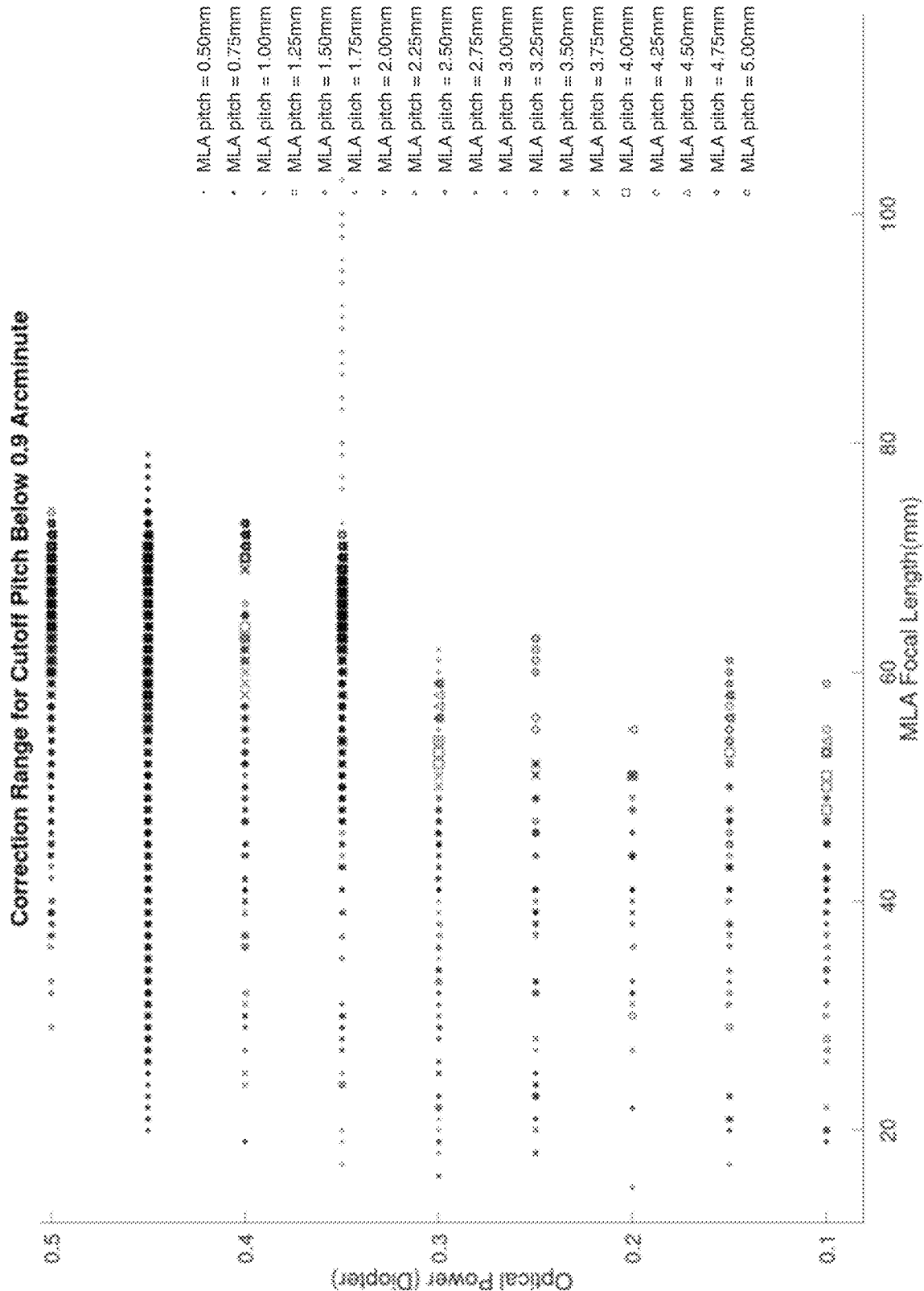
Figure 35F:
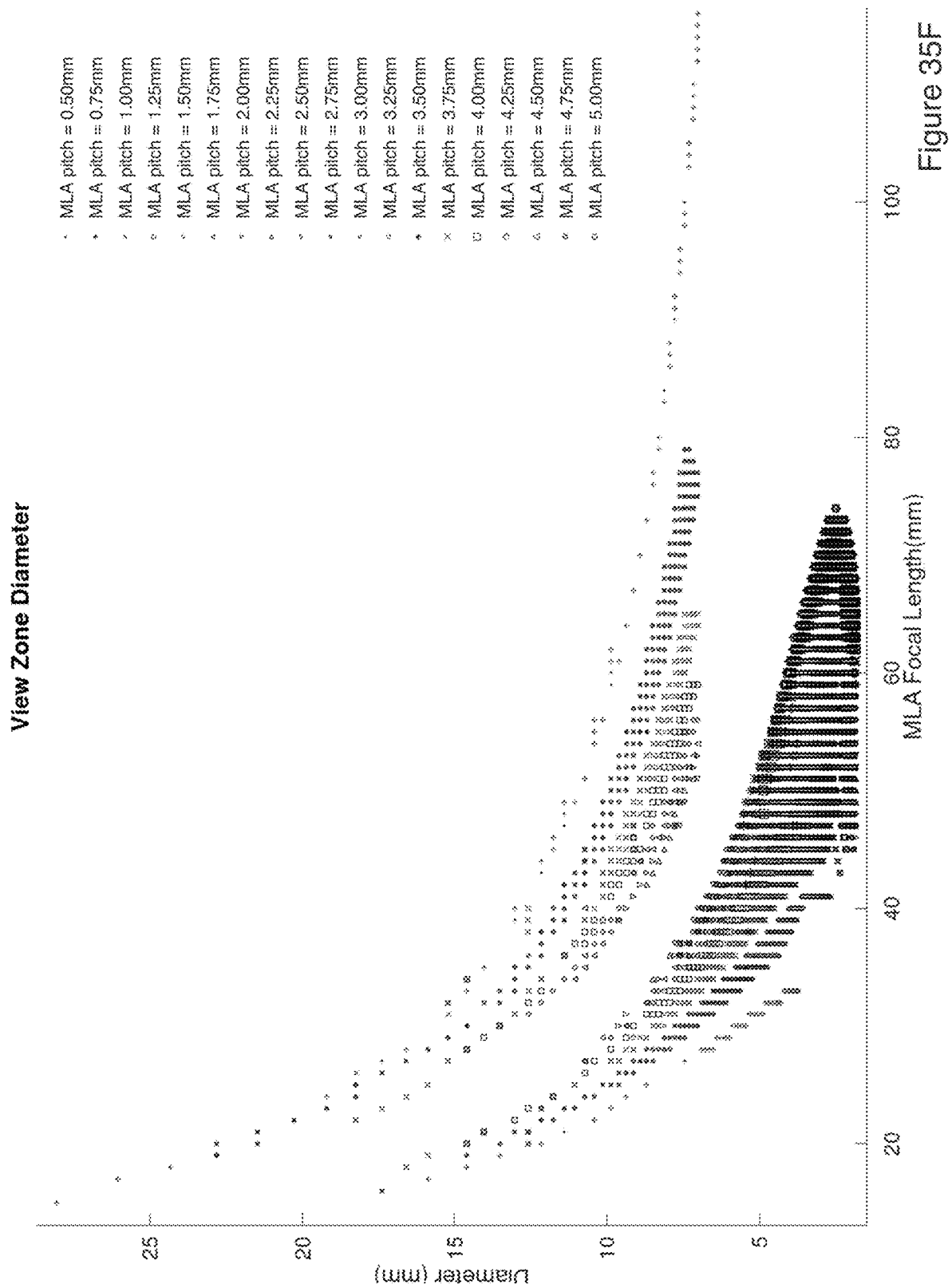
Figure 35G:
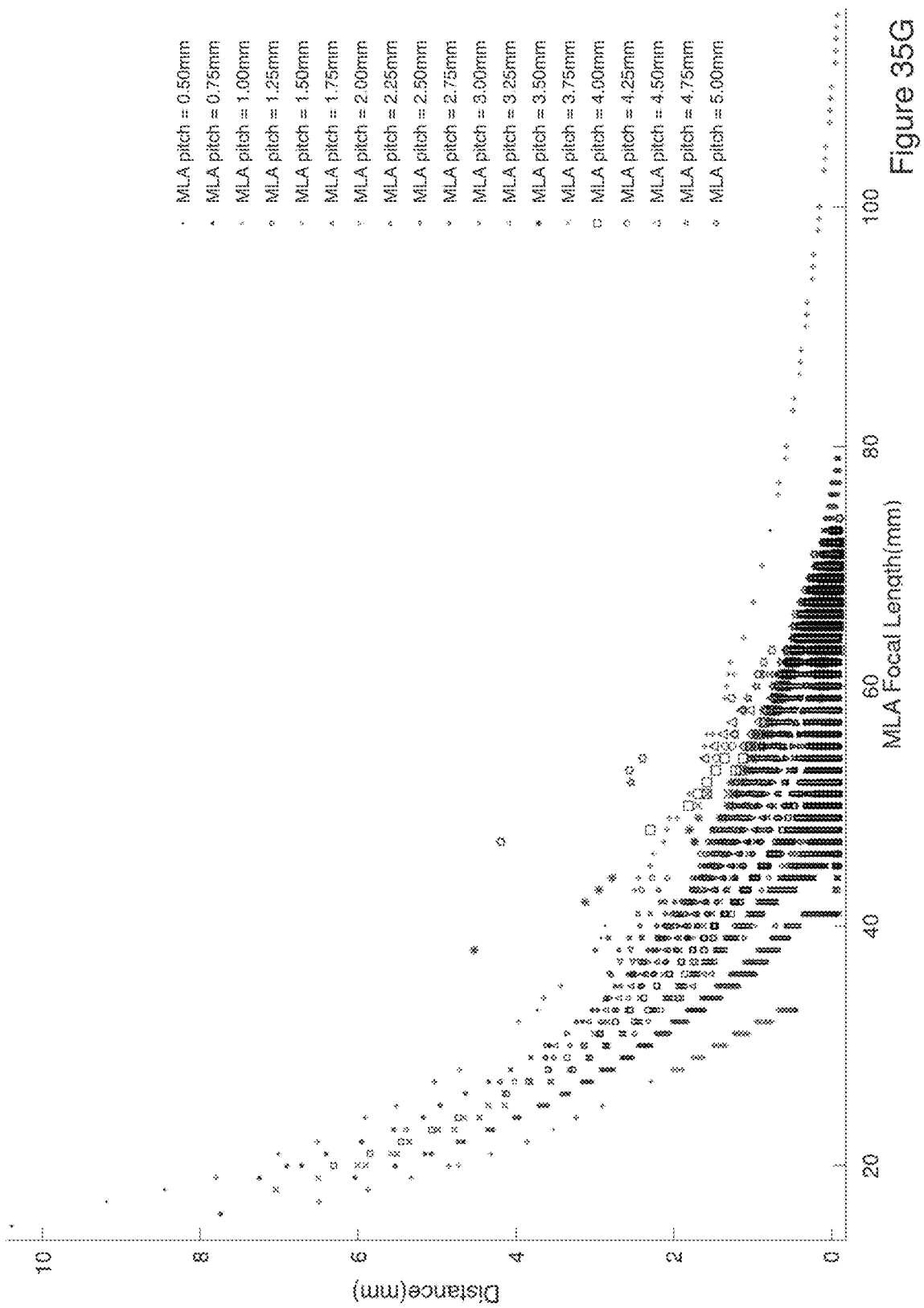
Figure 35H:
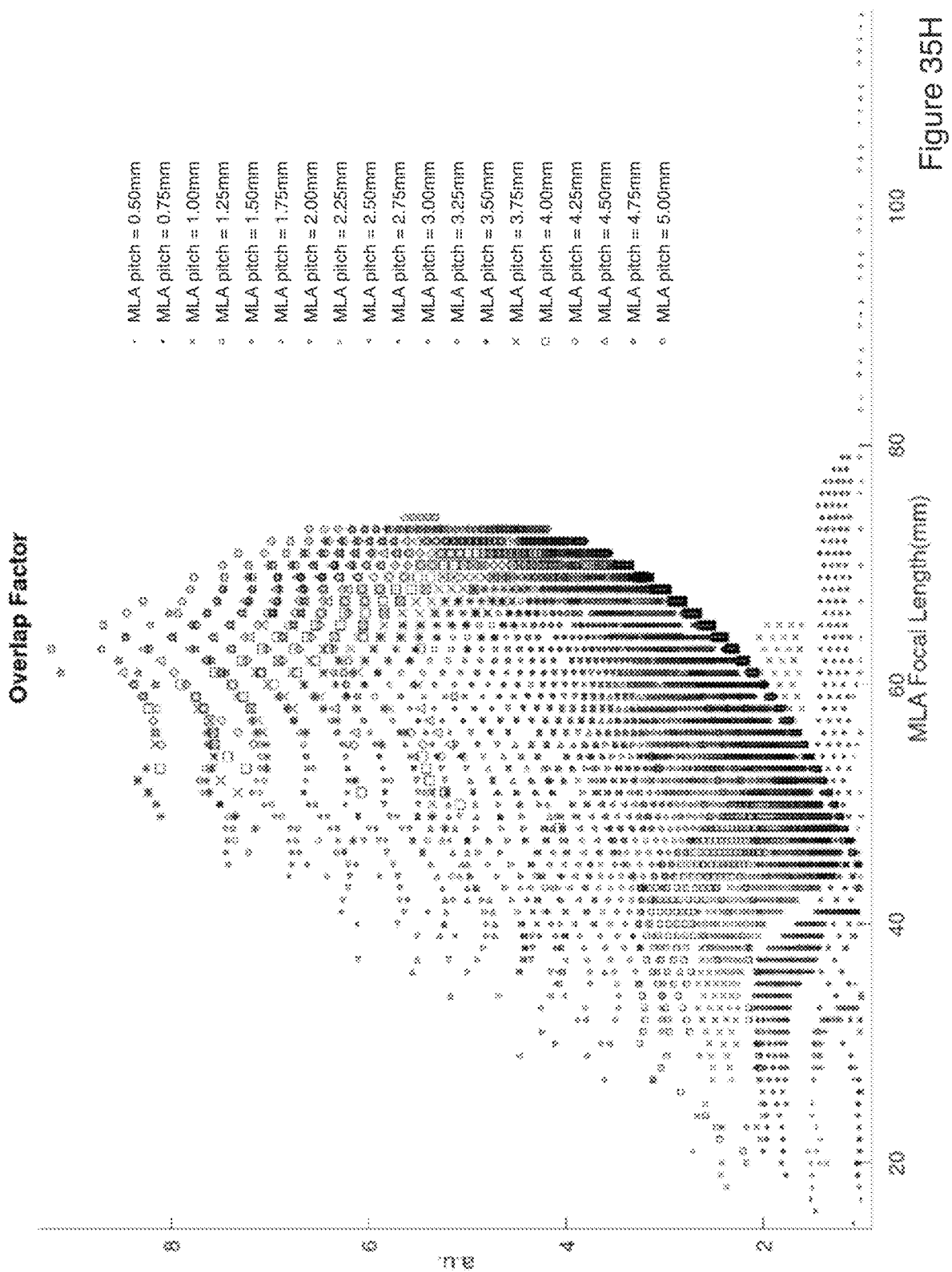
Figure 35I:
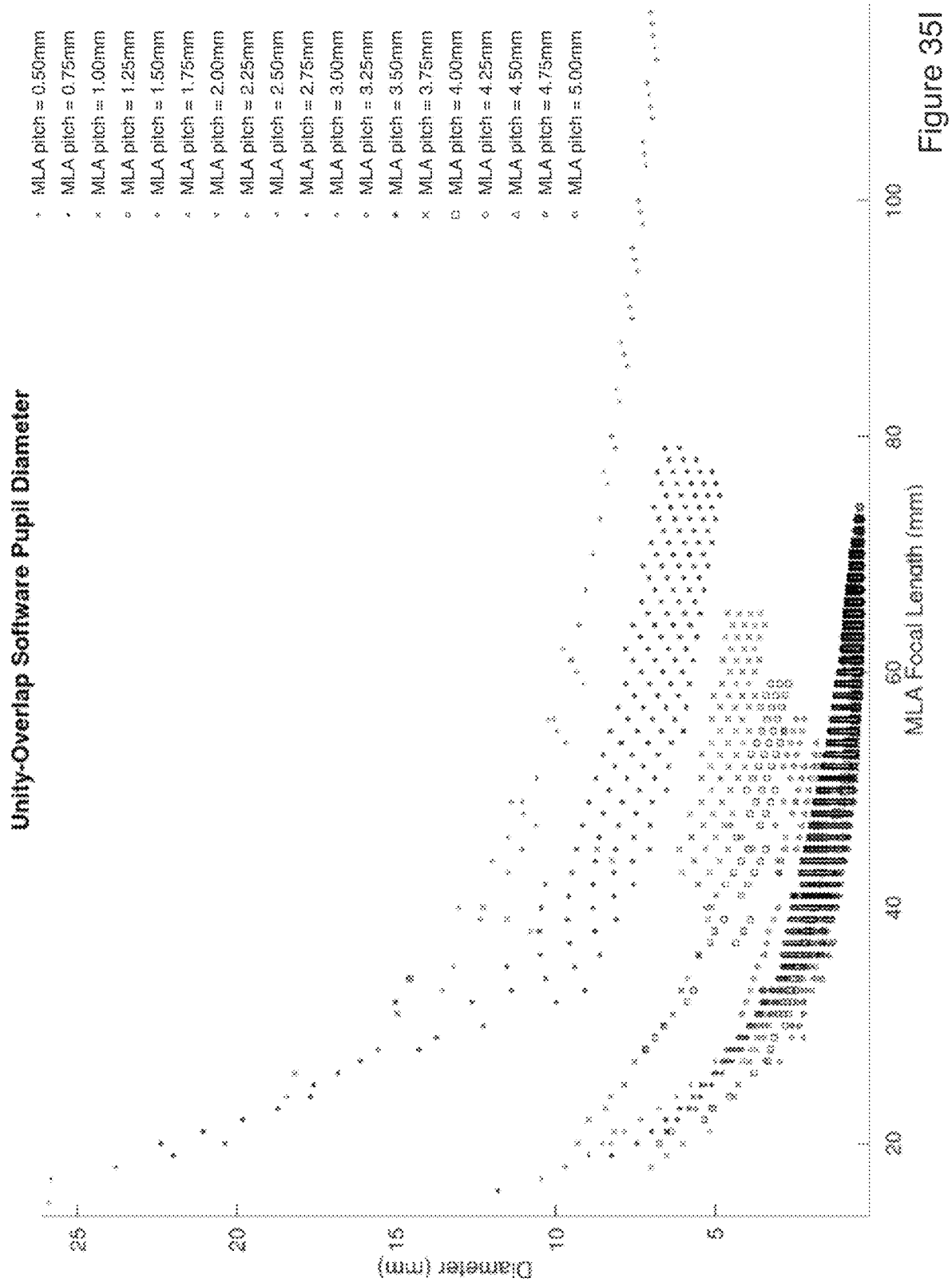

Similarly, ray-tracing on the retina plane (or eye lens focal plane) may be similarly modified to also shift the light filed image so that it is perceived by each eye as originating somewhere therebetween. In this case, as shown in FIG. 34B, a new step 3402 is added in between substeps 1612 and 1614, wherein the center position of the image on the retina (point 1708) is shifted horizontally so as to model the image center location 1726 being equally shifted by half the IPD.

In some embodiments, the IPD may be measured in real-time (via one or more cameras 3017 or a displacement sensor) or a pre-determined value may be used. The predetermined value may be an average value, for example a value corresponding to the patient's demographics, or it may be the patient's IPD that has been measured prior to using the device.

Accordingly, within the context of a subjective vision test, a confirmatory binocular correction may be simulated to validate respective corrections prescribed or applied to each eye based on a conclusion of the vision-based assessment.

In other embodiments, a binocular vision-based test may be implemented whereby both eyes are used concurrently to observe a same light field test content item, for instance, within the context of a cognitive impairment test whereby tracking of eye movements and/or responses may be executed in respect of a singular or same vision-based test content, for example, involving the displacement of and visual response to visual content in 2D and/or 3D. In other vision-based test, observation of certain visual effects like double-vision when rendering should result in the production of a common singular view, may server to screen for certain cognitive and/or visual impairments. These and other similar binocular testing approaches are considered to fall within the general scope and nature of the present disclosure.

Coarse View Zone Adjustment Transfer

In some embodiments, for example making use of a complementary optical system such as a tunable lens to provide coarse dioptric adjustments, to be fined tuned thereafter via the dynamic light field system, additional optical components may be interposed within the optical path to the device output to improve and optical quality of the perceived image, namely, to improve optical conditions for the effective propagation of the predominant view zone so produced, to the user's pupil and retina. For instance, in some of the above-described embodiments, a tunable or selectable lens is interposed along the predominant view zone optical path that, whose adjustable power, when combined with the user's eye lens, allows to shift or extend a dynamic corrective range provided by the light field components. For ideal optical control, the tunable or selectable lens would be located directly adjacent to the eye lens so to effectively combine their dioptric powers in accordance with simple optics calculations. However, this configuration is not readily achievable in most device form factors, thus requiring some distance along the output optical path between the eye and tunable or selectable lens.

In some embodiments, ray tracing computations can be dynamically adjusted to account for this distance in taking the specific optical arrangement and distancing into account. In other embodiments, however, a set of refractive lenses can be used, for example, within a telescope-like assembly, to optically transfer the light field exit plane at the tunable or selectable lens, to the eye-lens plane, thus providing a comparable effect without increasing a complexity of the ray tracing process while still benefiting from a dioptric corrective range extension/shift as provided by the tunable/selectable lens. Using this approach, additional magnification/demagnification can also be applied, resulting in greater image formation versatility, particularly, in providing some further adjustment or degree of freedom in controlling/managing the image viewing/perception parameter space.

In general, for magnification, the light field exit aperture will increase in size while the FoV will decrease proportionally to magnification factor. In addition, the tunable lens compensation power range will decrease quadratically proportional to this factor. Naturally, the opposite will take place for demagnification, the opposite effect happens.

Figure 28A:
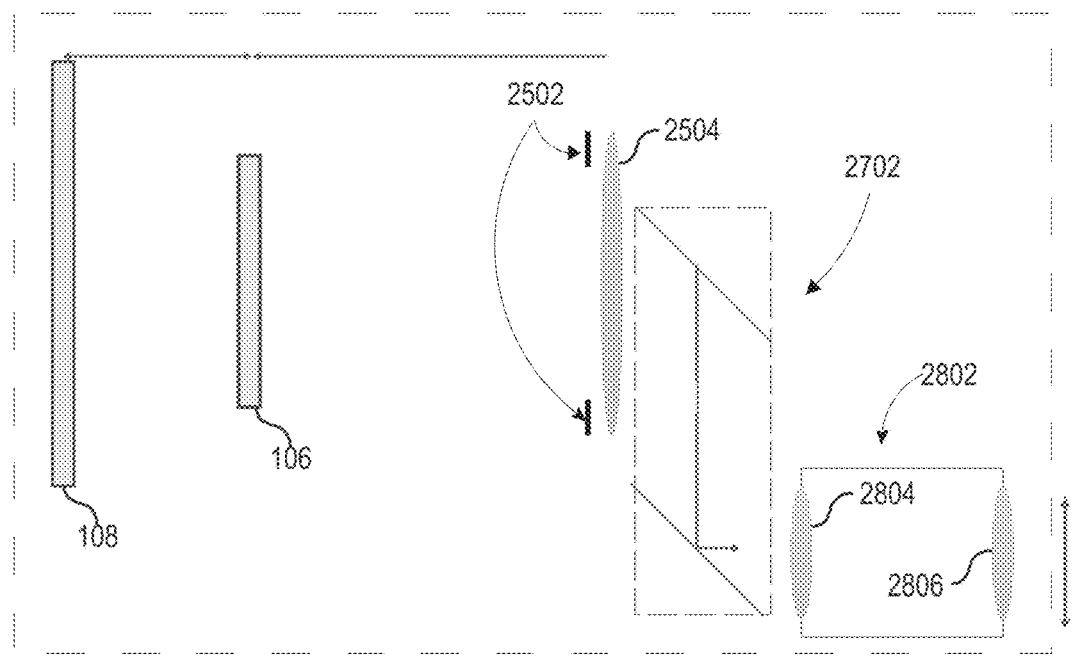
FIGS. 28A, 28B and 28C are schematic diagrams illustrating an exemplary refractor device using, in addition to the mirror assembly of FIG. 27A, a telescope assembly, in accordance with three different embodiments.

In some embodiments, as schematically illustrated in FIG. 28A, a Keplerian telescope assembly 2802 may be used, generally composed of an input lens 2804 of focal length $f_1$ and output lens 2806 of focal length $f_2$ and magnification defined as $M=f_2/f_1$. Using the paraxial approximation, the light field output at tunable lens 2504 is placed at $f_1$ distance from the first lens, and the device output at $f_2$ from the second lens (at the eye), which has an effect on the FoV, the angular and spatial pitch as well as the beam size and beam divergence. In addition, the power of tunable lens 2504 will be affected. This can be understood by realizing the association with the eye focal length error ($f_E$). Assume an input ray with the position and angle of incidence of $y_1$, $\theta_1$ at a focal length distance of the first lens of the telescope (e.g. lens 2804 in the example of FIG. 28A). A geometric optics formulation shows that the output ray of position and angle $y_2$, $\theta_2$ is characterized by:

$$y_2 = -My_1; \text{ and } \theta_2 = \left(\frac{1}{Mf_o} + M\frac{1}{f_E}\right)y_1 - \frac{\theta_1}{M}.$$

The amplitude equation ($y_2$) results in beam and light-field size magnification/demagnification. On the other hand, the telescope causes imbalance in the first term of $\theta_2$. This means that compensation of the eye error is not one to one with tunable lens 2504. For the eye focal error compensation, the following relationship can be satisfied:

$$\frac{1}{f_o} = -M^2 \frac{1}{f_E};$$

which means that for a magnifying telescope, a higher tunable lens power ($1/f_o$) is required to compensate for the eye power error ($1/f_E$), and lower tunable lens power is required using a de-magnifying telescope. The second term for the output angle ($\theta_2$) changes the angular spread of the light-field and divergence of the beams. This means that the light-field retinal spot minimum is shifted and FoV changes proportionally to 1/M. The beams angular and spatial pitch on cornea similarly change which also affect the angular resolution of the light field.

These effects can be incorporated for example via software-based optimization scripts. For unity gain configuration light-field may be transferred as:

$$y_2 = -y_1; \theta_2 = \left(\frac{1}{f_o} + \frac{1}{f_E}\right)y_1 - \theta_1.$$

and the eye power error is corrected when $f_o=-f_E$ as expected. Then the only correction needed is to invert the projected image.

Figure 28B:
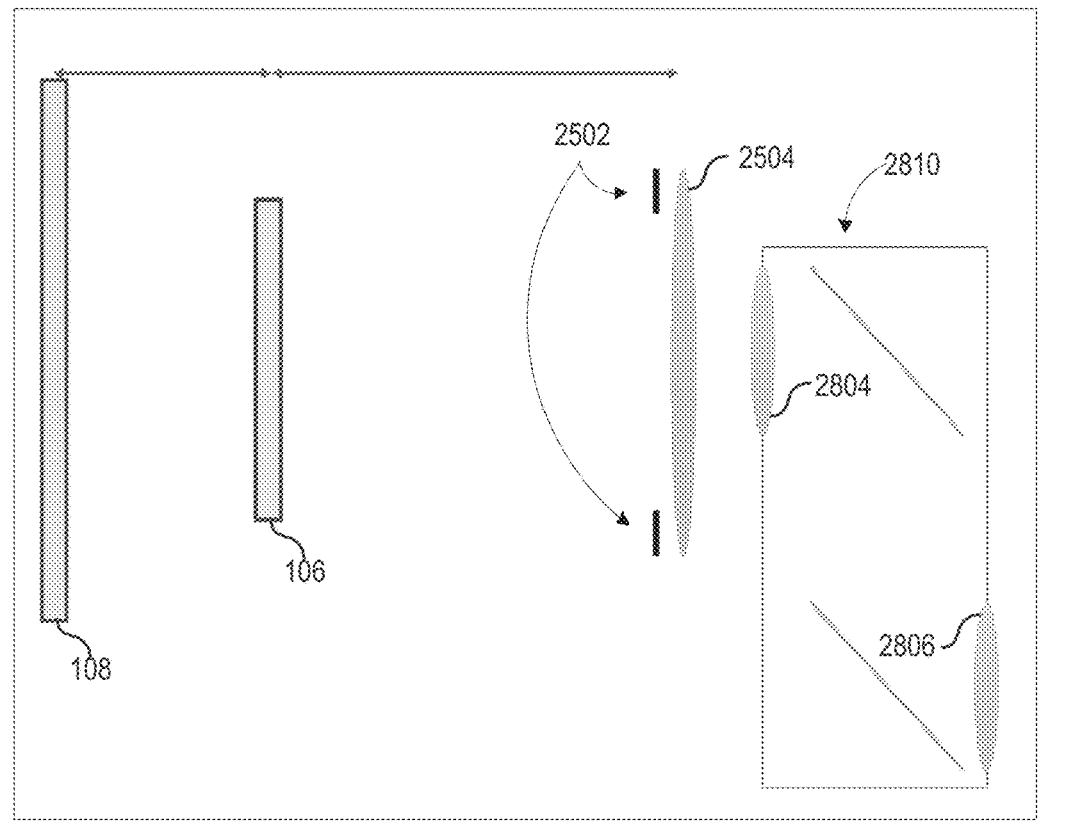

In some embodiments, mirror assembly 2712 and telescope assembly 2802 may be combined into a single assembly 2810, as shown schematically in FIG. 28B.

Figure 28C:
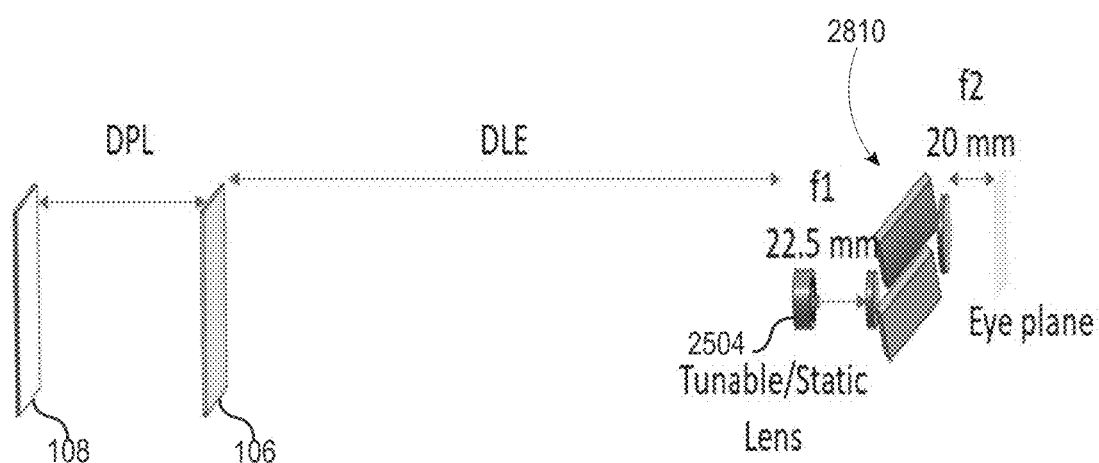

Similarly, FIG. 28C schematically illustrates another exemplary embodiment of a telescope assembly. In FIG. 28C, a set of lenses of focal length $f_1$ of 22.5 mm and $f_2$ of 20 mm are loaded at the input and output aperture of the mirror assembly described above. The power range for the tunable lens of 5.8 mm clear aperture is demagnified to expand the correction range from 15 diopter to ~19 diopter with clear aperture of 5.15 mm. This ensures light field coverage for a large area on the eye pupil to capture aberrations over this area on the pupil. In this embodiment, the tunable lens 2504 used to shift the optical power of the eye is placed between the light field display (composed of a pixel array 118 and a LFSL 116) and the telescope input lens at a focal length distance=22.5 mm from the primary principal plane. The distance between the secondary principal plane of the input telescope lens and primary principal plane of the output telescope lens equals $f_1$=42.5 mm. Then the eye is placed at $f_2$=20 mm distance from the secondary principal plane of the output telescope lens. The values of the lenses focal length were chosen to keep the compactness of the device and to allow for eye placement within reasonable distance to the telescope output lens using an eye cup piece. In some embodiments, implementing the lens assembly to the mirror assembly explained above reduces the effective distance between the pixel array to eye to the distance between the pixel array to the primary principal plane of the tunable lens of ~320–22.5 mm≈297.5 mm assuming thin lens model.

Table 3 below shows examples of specifications corresponding to embodiments using a telescope assembly:

TABLE 3

|  | (a)-t | (b)-t | (c)-t |
| --- | --- | --- | --- |
| MLA pitch, focal length (mm) | 1, 65 | 1.98, 46 | 1.98, 30 |
| Display to MLA distance (mm) | 45 | 44.5 | 43 |
| Angular pitch (arcminute) | 0.76 | 0.88 | 0.67 |
| Center light-field correction power (diopter) | −3.19 | −0.78 | −8.3 |
| Cutoff spatial resolution (arcminute) | 0.79 | 0.92 | 0.70 |
| View zone spacing (mm) | 6.55 | 13.13 | 13.6 |
| View zone separation from tunable lens aperture of 5.8 mm | −1.4 | 1.7 | 1.5 |
| Minimum software pupil diameter (mm) | 4.96 | 2.46 | 1.82 |

The needed aperture for the telescope lenses is calculated by realizing the light field spread (LFS) at each lens plane. This is given by for telescope lens1 and lens 2:

$$LFS1 = \frac{\sqrt{2}\,W_{Disp}f_1}{DPL+DLE} + \frac{W_O(DLE+f_1)}{DLE} - \min(P_O)W_O f_1;$$

and $$LFS2 = \frac{\sqrt{2}\,W_{Disp}f_1}{(DPL+DLE)} + \frac{W_O f_2}{f_1} - \frac{W_O}{DLE}f_1 + \max(P_O)W_O f_1;$$

where $W_{Disp}$ is the display width, DPL is the distance from the display to the LFSL, DLE is the effective distance from the LFSL to the eye, $W_O$ is the tunable lens clear aperture width, $P_O$ is the tunable lens power. In this example, option (a) results in maximum spread at the telescope input lens, with the spread of the light field being around ~13 mm at the input telescope lens, and ~12.1 mm at the telescope output lens.

In some embodiments, other variations may be considered, for example, by placing tunable lens 1804 between the telescope lenses (not shown). For example, placing the tunable lens 1804 at focal distances of both lenses ($f_1$ from lens 2804 and $f_2$ from lens 2806) results in the following equations:

$$y_2 = -My_1 - \frac{Mf_1^2}{f_O}\theta_1;$$

and $$\theta_2 = \frac{M}{f_E}y_1 - \left(\frac{1}{M} + \frac{f_1^2}{f_O}\frac{M}{f_E}\right)\theta_1.$$

where the first term in the angular response equation above shows that the tunable lens power does not compensate for the eye lens power error.

In some embodiments, flipping the placement distances ($f_2$ for lens 2104 and $f_1$ from lens 2106) results in:

$$y_2 = \left(-\frac{Mf_1}{f_O} + M^2\frac{f_1}{f_O} - M\right)y_1 - M\frac{f_1^2}{f_O}\theta_1;$$

$$\theta_2 = \left(-\frac{1}{f_O}\left[\left(1-\frac{1}{M}\right) + \left(1-\frac{Mf_1}{f_E}\right)(1-M)\right] + \frac{M}{f_E}\right)y_1 +$$

$$\left(-\frac{1}{M} + \frac{1}{M}\frac{f_1}{f_O} - \frac{f_1}{f_O} + \frac{Mf_1^2}{f_O f_E}\right)\theta_1;$$

where the terms including $f_1/f_E$ and $f_1/f_O$ can be minimized using small $f_1$ value and realizing that $f_O$ and $f_E$ are generally large.

To compensate for the eye refraction error, we get the following condition:

$$\frac{1}{f_O} = \frac{1}{f_E}\frac{M}{\left[\left(1-\frac{1}{M}\right) + \left(1-\frac{Mf_1}{f_E}\right)(1-M)\right]};$$

$$\cong \frac{1}{f_E}\frac{M}{\left[2 - \frac{1}{M} - M\right]}; Mf_1 \ll f_E.$$

Thus, with a negative magnification, power compensation can be gained. With this, tunable lens 2504 may be placed in front of the (Galilean) telescope.

Other lens stack assemblies may be considered.

Optimized Pupil Shaping

In some embodiments, a software-based pupil reshaping function may be used to reduce or remove unwanted view interference in the perceived light field image, such as one generated from refractor 102. For example, this software-based pupil reshaping function may be used, in some embodiments, at step 1108 of method 1100 described above. Indeed, method 1100 described above, in some embodiments, may, in some cases, have the effect of producing overlapping view zone artefacts where a view zone projection geometry does not adequately align or correspond with the viewer's eye geometry, positioning, alignment and/or response, and/or where intervening optics inadvertently interfere with view zone quality or accuracy. For instance, as illustrated schematically in FIG. 29, a digital display 2902 having a set of LFSEs 2904 disposed at a distance therefrom, will produce spatially recurring images in accordance with periodically recurring view zones 2906A, 2906B, 2906N. The view zone spacing may be prescribed by a spacing of the LSFEs 2904, as for example illustrated as view zone spacing 2908B between view zones 2906A and 2906B, and/or by software in opting to limit pixel use to certain areas thereby possibly imposing greater spacing between generated view zones, as for example illustrated by view zone spacing 2908N between view zones 2906A and 2906N. Correspondingly, a common software-controlled view zone width can be elected to more or less correspond with the user's pupil dimension, with some further consideration. For example, a view zone that is too conservatively narrow will potentially allow multiple view zones to enter the user pupil at once and produce a less stable effect, whereas one that is too broad may have other undesirable effects.

Meanwhile, as will be further detailed below, a geometrical mismatch in the formation of the desired view zones may also result in some perceived artifacts. For example, as illustrated in the photograph of FIG. 30A, an exemplary light field image which is generated with a light field ray-tracing method assuming a perfectly spherical pupil entrance, results in overlaid view zones, which, in some respects, is the result of having a corresponding circular unit cell which cannot be used to fill a polygonal lattice of the LFSL 106 without overlapping.

Therefore, in some embodiments, light field ray-tracing algorithms may include a pupil reshaping function configured to correspond with a geometry of the LFSL lattice, in this example a microlens lattice, meaning the lattice produced by the relative arrangement of the optical units or lenslets of the LFSL (e.g. not the shape of the optical units themselves).

Figure 31A:
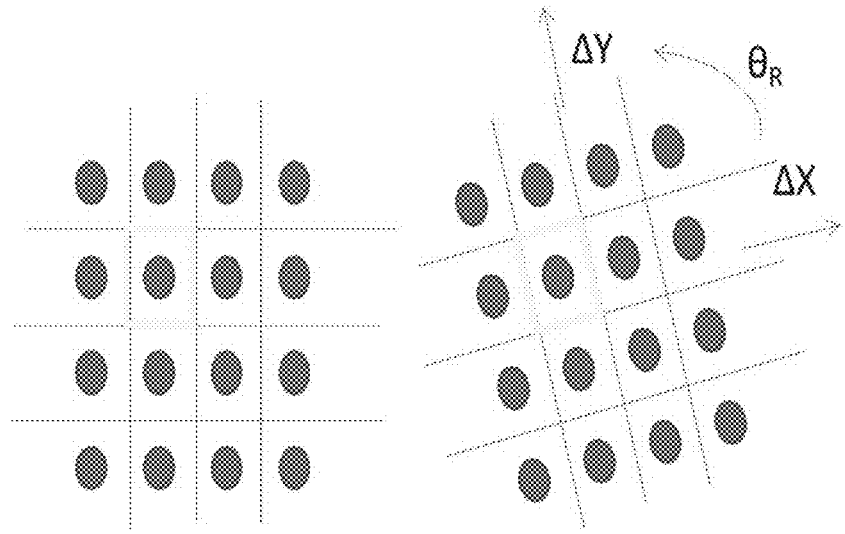
FIGS. 31A and 31B are schematic diagrams illustrating a software pupil reshaping function, in accordance with one embodiment.

In some embodiments, parameters considered by the reshaping function include the number $N_p$ of sides of a reciprocal lattice unit cell (e.g. 6 for hexagonal, 4 for square, etc.), a pupil size diameter of $W_{ppl}^{SW}$ and a LFSL rotation angle $\theta_R$ (e.g. with respect to the pixel display orientation). Thus, the pupil reshaping function may take the form, in some embodiments, of:

$$|\text{diff}| \le \frac{1}{\left|\cos\left(\text{mod}\left(\tan^{-1}\left(\frac{y_h - y_{ppl}}{x_h - x_{ppl}}\right) \pm \theta_R, \frac{2\pi}{N_P}\right)\right)\right|}$$

where |diff| is the distance from the pupil center to the ray hit point on pupil normalized to the software pupil radius $W_{ppl}^{SW}/2$, mod is the modulo function (defined as mod (x,y)=x−y*round(x/y)), $(x_h, y_h)$ are the ray hit coordinates on the pupil and $(x_{ppl}, y_{ppl})$ are the pupil center coordinates and $(x_h, y_h)$ are the coordinates of the light field ray on the pupil. Thus, the function above will exclude rays intersecting with (the pupil plane) that do not respect the inequality (e.g. rays outside of the polygon centered on the pupil center). The ± choice for $\theta_R$ depends on the rotation convention used for the to define the orientation of the LFSL 106 with respect to pixel display 108. FIG. 31A shows schematically an example of the unit cell of a rectangular reciprocal lattice that may be used for the shaping of the pupil.

Figure 31B:
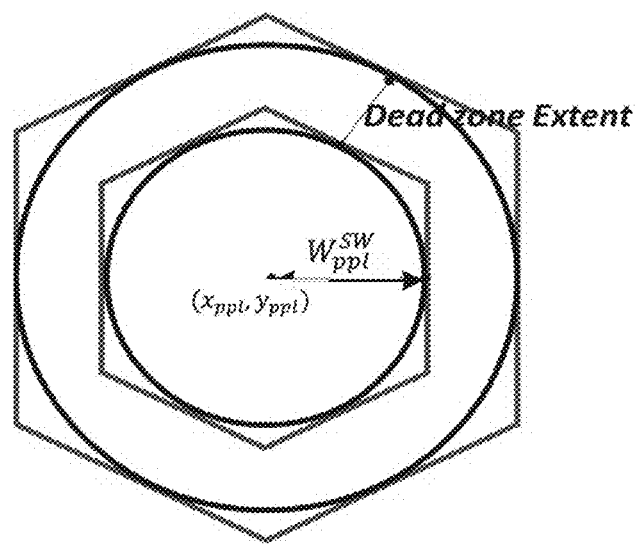

In some embodiments, the function above may be extended to account for a dead-zone region between the retinal bands, so as to better control the brightness uniformity and contrast of the formed image. This modified pupil shaping function allows to control the view zone transition as well, including intensity levels, intensity transition fade rates, blurring and the extent of the dead-zone region. In some embodiments, thus the dead-zone including pupil reshaping function may be defined as:

$$|\text{diff}| < \frac{\text{deadzone\_extent} + 1}{\left|\cos\left(\text{mod}\left(\tan^{-1}\left(\frac{y_h - y_{ppl}}{x_h - x_{ppl}}\right) \pm \theta_R, \frac{2\pi}{N_P}\right)\right)\right|};$$

where deadzone_extent defines a length extending beyond the pupil radius and characterizes the size of the polygonal pupil shape. FIG. 31B shows schematically an exemplary pupil/dead-zone shape defined for a unrotated LFSL 106 for a hexagonal lattice pattern. The result of such as function is shown in FIG. 30B, in which a photograph of a light field image generated in FIG. 30A but now using the pupil shaping function for a hexagonal lattice as described above.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A binocular vision-based testing device for digitally implementing a vision-based test for a user using both their left and right eye simultaneously, the device comprising:
    left and right digital display portions comprising respective pixel arrays;
    corresponding light field shaping layer (LFSL) portions comprising respective light field shaping element (LFSE) arrays disposed at a distance from said respective pixel arrays to shape a respective left and right light field emanating therefrom; and
    a digital data processor operable on pixel data for vision-based test content to output adjusted pixel data to be simultaneously rendered via said respective pixel arrays and LFSE arrays in accordance with a designated user perception adjustment and projected within respective predominant left and right light field view zones formed thereby along respective optical paths to respective left and right optical outputs while concurrently projecting at least some same vision-based test content within adjacent left and right view zones, respectively;
    wherein projection of said adjacent left and right view zones toward said right and left optical outputs is optically obstructed from interfering with user viewing of said predominant right and left light field view zones, respectively.

2. The binocular vision-based testing device of claim 1, wherein a distance between a center of said left and right digital display portions is greater than an interpupillary distance resulting in an initial separation between said respective predominant left and right light field view zones also being greater than said interpupillary distance, wherein said left and right optical outputs are disposed so to substantially correspond with said interpupillary distance, and wherein the device further comprises respective mirror assemblies disposed along said respective left and right optical paths to non-refractively narrow said initial separation substantially in line with said interpupillary distance thereby substantially aligning said left and right light field view zones with said left and right optical outputs.

3. The binocular vision-based testing device of claim 2, wherein said left and right optical outputs and said respective mirror assemblies are adjustable to accommodate different interpupillary distances.

4. The binocular vision-based testing device of claim 2, wherein said mirror assemblies comprise periscope-like assemblies.

5. The binocular vision-based testing device of claim 1, wherein said vision-based test content is to be simultaneously perceived by the left and right eye via said left and right optical outputs to be at a common virtual position relative thereto.

6. The binocular vision-based testing device of claim 5, wherein said common virtual position comprises a virtual depth position relative to said display portions.

7. The binocular vision-based testing device of claim 6, wherein said designated user perception adjustment comprises respective left and right vision correction adjustments.

8. The binocular vision-based testing device of claim 1, wherein said left and right display portions comprise respective displays, and wherein said respective LFSL portions comprise respective microlens arrays.

9. The binocular vision-based testing device of claim 1, wherein said projection of said adjacent left and right view zones is optically obstructed by a physical barrier.

10. The binocular vision-based testing device of claim 1, wherein said digital data processor is operable to adjust rendering of said vision-based test content via said respective LFSL portions so to accommodate for a visual aberration in at least one of a user's left or right eye.

11. The binocular vision-based testing device of claim 10, wherein said visual aberration comprises distinct respective visual aberrations for the left and right eye.

12. The binocular vision-based testing device of claim 11, wherein the vision-based test comprises a visual acuity test to determine an optimal user perception adjustment corresponding with a reduced user visual acuity level in prescribing corrective eyewear or surgery for each of the user's left and right eye.

13. The binocular vision-based testing device of claim 12, wherein the vision-based test is first implemented for each eye separately in identifying a respective optimal user perception adjustment therefor, and wherein both said respective optimal user perception adjustment are then validated concurrently via binocular rendering of said vision-based content according to each said respective optimal user perception adjustment.

14. The binocular vision-based testing device of claim 10, wherein the device is a refractor or a phoropter.

15. The binocular vision-based testing device of claim 1, wherein said vision-based test comprises a cognitive impairment test to determine a physiological user response to a designated set of binocular user perception adjustments.

16. The binocular vision-based testing device of claim 1, wherein the device further comprises respective optical view zone isolators disposed along said respective optical paths between said LFSL portions and said respective left and right optical outputs to at least partially obstruct visual content projected within said adjacent left and right view zones from interfering with visual content projected within said predominant left and right view zones, respectively.

17. The binocular vision-based testing device of claim 16, wherein said each of said optical view zone isolators defines a view zone isolating aperture dimensioned and disposed so to at most substantially correspond with a cross section of said predominant view zones.

18. The binocular vision-based testing device of claim 16, wherein said hardware processor is operable to adjust said adjusted pixel data to adjust said designated user perception adjustment within a designated range, wherein the device further comprises an adjustable refractive optical system interposed between said LFSL portions and said respective optical outputs to shift said designated range in extending an overall range of the device, and wherein said respective view zone isolators are disposed between said LFSL portions and said adjustable refractive optical system so to at least partially obstruct projection of said adjacent view zones through said adjustable refractive optical system.

19. The binocular vision-based testing device of claim 18, wherein said adjustable refractive optical system comprises respective tunable lenses or respective lenses selectable from respective arrays of selectable lenses.

20. The binocular vision-based testing device of claim 16, wherein said hardware processor is operable to adjust said adjusted pixel data to adjust said designated user perception adjustment within a designated range, wherein the device further comprises respective tunable lenses interposed between said LFSL portions and said respective optical outputs to shift said designated range in extending an overall range of the device, and wherein said respective view zone isolators are defined by said respective tunable lenses.

21. The binocular vision-based testing device of claim 1, wherein said hardware processor is operable to adjust said adjusted pixel data to adjust said designated user perception adjustment within a designated range, wherein the device further comprises an adjustable refractive optical element interposed between said LFSL portions and said respective optical outputs to shift said designated range in extending an overall range of the device, and wherein the device further comprises an optical assembly to optically transfer respective exit plane light fields of said adjustable refractive optical element to said respective optical outputs.

22. The binocular vision-based testing device of claim 21, wherein said optical assembly comprises respective left and right telescope-like assemblies.

23. The binocular vision-based testing device of claim 22, wherein said telescope-like assemblies optimize at least one of the following light field parameters at the optical outputs: exit aperture, field of view (FoV), and/or angular resolution.

24. The binocular vision-based testing device of claim 22, wherein said telescope-like assemblies define Keplerian-type assemblies each comprising an input lens disposed along said respective optical path at an input lens focal distance downstream from said adjustable refractive optical element to receive said exit plane light field therefrom, and an output lens disposed along said respective optical path at an output lens focal distance upstream of the respective optical output.

25. The binocular vision-based testing device of claim 22, wherein said telescope-like assemblies define Galilean-type telescope assemblies each comprising an input lens disposed along said respective optical path at an input lens focal distance upstream of said adjustable refractive optical element, and an output lens disposed along said respective optical path at an output lens focal distance downstream of said adjustable refractive optical system.

26. The binocular vision-based testing device of claim 1, wherein said distance is lower than a focal distance of said LFSE array.

* * * * *